(12) United States Patent
Ju et al.

(10) Patent No.: US 11,499,186 B2
(45) Date of Patent: Nov. 15, 2022

(54) DNA SEQUENCING BY SYNTHESIS USING MODIFIED NUCLEOTIDES AND NANOPORE DETECTION

(71) Applicants: Jingyue Ju, Englewood Cliffs, NJ (US); Shiv Kumar, Belle Mead, NJ (US); Zengmin Li, Flushing, NY (US); Chuanjuan Tao, New York, NY (US); Minchen Chien, Tenafly, NJ (US); James J. Russo, New York, NY (US); Sergey Kalachikov, New York, NY (US); Ken Shepard, Ossining, NY (US); Jacob Karl Rosenstein, Providence, RI (US)

(72) Inventors: Jingyue Ju, Englewood Cliffs, NJ (US); Shiv Kumar, Belle Mead, NJ (US); Zengmin Li, Flushing, NY (US); Chuanjuan Tao, New York, NY (US); Minchen Chien, Tenafly, NJ (US); James J. Russo, New York, NY (US); Sergey Kalachikov, New York, NY (US); Ken Shepard, Ossining, NY (US); Jacob Karl Rosenstein, Providence, RI (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 65 days.

(21) Appl. No.: 16/653,278

(22) Filed: Oct. 15, 2019

(65) Prior Publication Data

US 2020/0115745 A1    Apr. 16, 2020

Related U.S. Application Data

(62) Division of application No. 13/994,431, filed as application No. PCT/US2011/065640 on Dec. 16, 2011, now Pat. No. 10,443,096.

(60) Provisional application No. 61/557,558, filed on Nov. 9, 2011, provisional application No. 61/424,480, filed on Dec. 17, 2010.

(51) Int. Cl.
| | |
|---|---|
| C12Q 1/68 | (2018.01) |
| C12Q 1/6869 | (2018.01) |
| C07H 19/10 | (2006.01) |
| C07H 21/00 | (2006.01) |
| G01N 33/487 | (2006.01) |

(52) U.S. Cl.
CPC .......... *C12Q 1/6869* (2013.01); *C07H 19/10* (2013.01); *C07H 21/00* (2013.01); *G01N 33/48721* (2013.01)

(58) Field of Classification Search
CPC ...... C12Q 1/6869; C07H 19/10; C07H 21/00; G01N 33/48721
See application file for complete search history.

(56) References Cited

U.S. PATENT DOCUMENTS

| | | |
|---|---|---|
| 5,756,355 A | 5/1998 | Lang et al. |
| 5,770,367 A | 6/1998 | Southern et al. |
| 5,795,782 A | 8/1998 | Church et al. |
| 5,804,386 A | 9/1998 | Ju et al. |
| 5,814,454 A | 9/1998 | Ju |
| 5,876,936 A | 3/1999 | Ju |
| 5,952,180 A | 9/1999 | Ju et al. |
| 6,015,714 A | 1/2000 | Baldarelli et al. |
| 6,046,005 A | 4/2000 | Ju et al. |
| 6,362,002 B1 | 3/2002 | Denison et al. |
| 6,383,749 B2 | 5/2002 | Bochkariov et al. |
| 6,399,335 B1 | 6/2002 | Kao et al. |
| 6,413,792 B1 | 7/2002 | Sauer et al. |
| 6,485,703 B1 | 11/2002 | Cote et al. |
| 6,616,895 B2 | 9/2003 | Dugas et al. |
| 6,627,748 B1 | 9/2003 | Ju et al. |
| 6,664,079 B2 | 12/2003 | Ju et al. |
| 6,746,594 B2 | 6/2004 | Akeson et al. |
| 6,916,665 B2 | 7/2005 | Bayley et al. |
| 7,074,597 B2 | 7/2006 | Ju et al. |
| 7,189,503 B2 | 3/2007 | Akeson et al. |
| 7,238,485 B2 | 7/2007 | Akeson et al. |
| 7,279,337 B2 | 10/2007 | Zhu |
| 7,345,159 B2 | 3/2008 | Ju et al. |
| 7,622,279 B2 | 11/2009 | Ju et al. |
| 7,622,934 B2 | 11/2009 | Hibbs et al. |
| 7,635,578 B2 | 12/2009 | Ju et al. |
| 7,713,698 B2 | 5/2010 | Ju et al. |
| 7,745,116 B2 | 6/2010 | Williams |

(Continued)

FOREIGN PATENT DOCUMENTS

| | | |
|---|---|---|
| WO | WO 2001/048235 A2 | 7/2001 |
| WO | WO 2001/094609 | 12/2001 |

(Continued)

OTHER PUBLICATIONS

Akeson, M. et al. (1999) "Microsecond time-scale discrimination between polycytidylic acid and polyadenylic acid segments wtihin single RNA molecules" Biophys. J. 77:3227-3233.

Amendment to Notice of Insufficiency, filed Dec. 31, 2015 in connection with U.S. Appl. No. 14/776,461.

Andersen, Sequencing and the single channel. Biophys J. Dec. 1999; 77(6):2899-901.

(Continued)

*Primary Examiner* — Jezia Riley

(74) *Attorney, Agent, or Firm* — Gary J. Gershik

(57) ABSTRACT

This disclosure is related to a method of sequencing a single-stranded DNA using deoxynucleotide polyphosphate analogues and translocation of tags from incorporated deoxynucleotide polyphosphate analogues through a nanopore.

20 Claims, 35 Drawing Sheets

(56) References Cited

U.S. PATENT DOCUMENTS

| | | |
|---|---|---|
| 7,777,505 B2 | 8/2010 | White et al. |
| 7,790,869 B2 | 9/2010 | Ju et al. |
| 7,883,869 B2 | 2/2011 | Ju et al. |
| 7,939,270 B2 | 5/2011 | Holden et al. |
| 7,947,454 B2 | 5/2011 | Akeson et al. |
| 7,982,029 B2 | 7/2011 | Ju et al. |
| 8,058,414 B2 | 11/2011 | Menchen et al. |
| 8,088,575 B2 | 1/2012 | Ju et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,298,792 B2 | 10/2012 | Ju et al. |
| 8,541,849 B2 | 9/2013 | Chen et al. |
| 8,652,779 B2 | 2/2014 | Turner et al. |
| 8,796,432 B2 | 8/2014 | Ju et al. |
| 8,889,348 B2 | 11/2014 | Ju |
| 9,115,163 B2 | 8/2015 | Ju et al. |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 9,297,042 B2 | 3/2016 | Ju et al. |
| 9,528,151 B2 | 12/2016 | Ju et al. |
| 9,605,309 B2 | 3/2017 | Davis et al. |
| 9,624,539 B2 | 4/2017 | Ju et al. |
| 9,670,539 B2 | 6/2017 | Ju et al. |
| 2003/0027140 A1 | 2/2003 | Ju et al. |
| 2003/0054360 A1 | 3/2003 | Gold et al. |
| 2003/0166282 A1 | 9/2003 | Brown et al. |
| 2003/0198982 A1 | 10/2003 | Seela et al. |
| 2005/0032081 A1 | 2/2005 | Ju et al. |
| 2005/0208574 A1 | 9/2005 | Bayley et al. |
| 2005/0239134 A1 | 10/2005 | Gorenstein et al. |
| 2006/0057565 A1 | 3/2006 | Ju et al. |
| 2006/0105461 A1 | 5/2006 | Tom-Moy et al. |
| 2006/0115951 A1 | 6/2006 | Mosley et al. |
| 2006/0252037 A1 | 11/2006 | Ju et al. |
| 2007/0190542 A1 | 8/2007 | Ling et al. |
| 2007/0275387 A1 | 11/2007 | Ju et al. |
| 2008/0101988 A1 | 5/2008 | Kang et al. |
| 2008/0199932 A1 | 8/2008 | Hanzel et al. |
| 2008/0218184 A1 | 9/2008 | White et al. |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0099786 A1 | 4/2009 | Oliver et al. |
| 2009/0136958 A1 | 5/2009 | Gershow et al. |
| 2009/0167288 A1 | 7/2009 | Reid et al. |
| 2009/0240030 A1 | 9/2009 | Ju et al. |
| 2009/0263791 A1 | 10/2009 | Ju et al. |
| 2009/0298072 A1 | 12/2009 | Ju |
| 2009/0325154 A1 | 12/2009 | Ju et al. |
| 2010/0025249 A1 | 2/2010 | Polonsky et al. |
| 2010/0035260 A1 | 2/2010 | Olasagasti et al. |
| 2010/0072080 A1 | 3/2010 | Karhanek et al. |
| 2010/0227414 A1 | 9/2010 | Ervin |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0014611 A1 | 1/2011 | Ju et al. |
| 2011/0039259 A1 | 2/2011 | Ju et al. |
| 2011/0160093 A1 | 6/2011 | Van den Boom et al. |
| 2011/0174625 A1 | 7/2011 | Akeson et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0287414 A1 | 11/2011 | Chen et al. |
| 2012/0052188 A1 | 3/2012 | Chen et al. |
| 2012/0094278 A1 | 4/2012 | Akeson et al. |
| 2012/0115736 A1 | 5/2012 | Bjornson et al. |
| 2012/0142006 A1 | 6/2012 | Ju et al. |
| 2012/0156680 A1 | 6/2012 | Ju et al. |
| 2012/0160681 A1 | 6/2012 | Davis et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0214162 A1 | 8/2012 | Oliver |
| 2012/0261261 A1 | 10/2012 | Huber |
| 2013/0264207 A1 | 10/2013 | Ju et al. |
| 2013/0280700 A1 | 10/2013 | Ju et al. |
| 2014/0034497 A1 | 2/2014 | Davis et al. |
| 2014/0093869 A1 | 4/2014 | Ju et al. |
| 2014/0206553 A1 | 7/2014 | Ju et al. |
| 2014/0309144 A1* | 10/2014 | Turner .............. C12Q 1/6869 506/16 |
| 2014/0315191 A1 | 10/2014 | Ju et al. |
| 2014/0377743 A1 | 12/2014 | Ju et al. |
| 2015/0037788 A1 | 2/2015 | Ju et al. |
| 2015/0080232 A1 | 3/2015 | Ju et al. |
| 2015/0111759 A1 | 4/2015 | Ju et al. |
| 2015/0119259 A1 | 4/2015 | Ju et al. |
| 2015/0197800 A1 | 7/2015 | Ju et al. |
| 2015/0368710 A1 | 12/2015 | Fuller et al. |
| 2016/0024570 A1 | 1/2016 | Ju et al. |
| 2016/0024574 A1 | 1/2016 | Ju et al. |
| 2016/0041179 A1 | 2/2016 | Ju et al. |
| 2016/0208313 A1 | 7/2016 | Ju et al. |
| 2016/0264612 A1 | 9/2016 | Ju et al. |
| 2016/0265048 A1 | 9/2016 | Ju et al. |
| 2016/0312279 A1 | 10/2016 | Ju et al. |
| 2017/0058335 A1 | 3/2017 | Tao et al. |
| 2017/0096704 A1 | 4/2017 | Ju |
| 2017/0101675 A1 | 4/2017 | Ju et al. |

FOREIGN PATENT DOCUMENTS

| | | |
|---|---|---|
| WO | WO 02/22883 A1 | 3/2002 |
| WO | WO 02/29003 | 4/2002 |
| WO | WO 02/79519 A1 | 10/2002 |
| WO | WO 2003/020734 A2 | 3/2003 |
| WO | WO 2004/071155 | 8/2004 |
| WO | WO 2004/071155 A2 | 8/2004 |
| WO | WO 2004/072238 A2 | 8/2004 |
| WO | WO 2007/127327 | 11/2007 |
| WO | WO 2007/146158 A1 | 12/2007 |
| WO | WO 08/69973 A2 | 6/2008 |
| WO | WO 2008/102120 | 8/2008 |
| WO | WO 2008/124107 | 10/2008 |
| WO | WO 2009/007743 | 1/2009 |
| WO | WO 2009/020682 A2 | 2/2009 |
| WO | WO 2009/051807 A1 | 4/2009 |
| WO | WO 2009/054922 | 4/2009 |
| WO | WO 2010/109197 A2 | 9/2010 |
| WO | WO 2010/117470 A2 | 10/2010 |
| WO | WO 2011/038241 A1 | 3/2011 |
| WO | WO 2011/097028 A1 | 8/2011 |
| WO | WO 2011/106459 | 9/2011 |
| WO | WO 2012/009578 | 1/2012 |
| WO | WO 2012/083249 | 6/2012 |
| WO | WO 2012/162429 | 11/2012 |
| WO | WO 2013/016486 A1 | 1/2013 |
| WO | WO 2013/123450 | 8/2013 |
| WO | WO 2013/154999 | 10/2013 |
| WO | WO 2013/188841 | 12/2013 |
| WO | WO 2013/191793 | 12/2013 |
| WO | WO 2014/144883 | 9/2014 |
| WO | WO 2014/144898 | 9/2014 |
| WO | WO 2015/123430 | 8/2015 |
| WO | WO 2015/148402 | 10/2015 |
| WO | WO 2015/179284 | 11/2015 |
| WO | WO 2016/144973 | 9/2016 |
| WO | WO 2016/154215 | 9/2016 |

OTHER PUBLICATIONS

Apr. 13, 2018 Communication Pursuant to Article 94(3) EPC, issued by the European Patent Office in connection with EP 13775787.8, Ju et al.

Apr. 16, 2014 Communication transmitting Supplementary European Search Report and European Search Opinion in connection with European Patent Application No. EP 11848220.

(56) References Cited

OTHER PUBLICATIONS

Apr. 18, 2016 Response to Feb. 3, 2016 Office Action issued in connection with Chinese Patent Application No. 200780028545.1.
Apr. 25, 2017 Amendment in Response to the Oct. 26, 2016 Office Action issued in connection with U.S. Appl. No. 14/391,337, Ju et al.
Apr. 30, 2012 Amendment in Response to Office Action dated Nov. 29, 2011 in connection with U.S. Appl. No. 12/308,091.
Apr. 9, 2013 Third Office Action in connection with Chinese Patent Application No. 200780028545.1.
Ashkenasy et al. Recognizing a single base in an individual DNA strand: a step toward DNA sequencing in nanopores. Angew Chem Int Ed Engl. Feb. 18, 2005; 44(9):1401-4.
Atanasnov et al. Membrane on a chip: a functional tethered lipid bilayer nembrane on silicon oxide surfaces. Biophys J. Sep. 2005; 89(3):1780-8.
Aug. 11, 2014 Response to Mar. 27, 2014 Office Action in connection ith Chinese Patent Application No. 201180063978.7.
Aug. 18, 2017 Amendment in Response to Communication Pursuant to Article 94(3) EPC, issued by the European Patent Office in connection with EP 13775787.8, Ju et al.
Aug. 18, 2017 Amendment in Response to Communication Pursuant to Article 94 (3), dated Feb. 9, 2017 by the European Patent Office in connection ith EP 13807639.3, Ju et al.
Aug. 4, 2015 Applicant Statement in connection with U.S. Appl. No. 14/666,124 regarding Amendments to p. 40 Regarding Tagged Nucleotides.
Aug. 5, 2016 Communication Under Rule 71(3) EPC issued by the European Patent Office in connection with European Patent Application No. EP11848220.7, Ju et al.
Benner, et al. Sequence-specific detection of individual DNA polymerase complexes in real time using a nanopore. Nat Nanotechnol. Nov. 2007; 2(11):718-24. Epub Oct. 28, 2007.
Bezrukov, S.M. et al. (2001) "Neutral Polymers in the nanopores of alamethicin and alpha-hemolysin." Biologicheskie Membrany 18:451-455.
Bokhari, S.H. et al. (2005) "A Parallel Graph Decomposition Algorithm for DNA Sequencing with Nanopores" Bioinformatics 21(7):889-896.
Buchmann, et al. Electrochemical release from gold-thiolate electrodes for controlled insertion of ion channels into bilayer membranes. Bioorg Med Chem. Mar. 15, 2004; 12(6):1315-24.
Butler, et al. Determination of RNA orientation during translocation through a biological nanopore. Biophys J. Jan. 1, 2006; 90(1):190-9. Epub Oct. 7, 2005.
Butler, et al. Ionic current blockades from DNA and RNA molecules in the alpha-hemolysin nanopore. Biophys J. Nov. 1, 2007; 93(9):3229-40. Epub Aug. 3, 2007.
Chandler, E.L et al. (2004) "Membrane Surface Dynamics of DNA-Threaded Nanopores Revealed by Simultaneous Single-Molecule Optical and Ensemble Electrical Recording." Langmuir 20:898-905.
Clarke, et al. "Continuous base identification for single-molecule nanopore DNA sequencing" Nat Nanotechnol. Apr. 2009; 4(4):265-70. Epub Feb. 22, 2009.
Communication Pursuant to Article 94(3), dated Feb. 23, 2018 by the European Patent Office in connection with EP 13807639.3, Ju et al.
Communication Pursuant to Article 94(3), dated Feb. 9, 2017 by the European Patent Office in connection with EP 13807639.3.
Communication pursuant to Rule 164(1) EPC dated Dec. 2, 2015 by the EPO in connection with EP 13807639.3.
Communication pursuant to Rule 164(1) EPC dated Dec. 7, 2015 by the EPO in connection with EP 13775787.8.
Deamer, D.W. et al (2002) "Characterization of nucleic acids by nanopore analysis." Acc. Chem. Res. 35(10):817-825.
Dec. 22, 2014 Second Office Action in connection with Chinese Patent Application No. 201180063978.7.
Dec. 23, 2014 Communication pursuant to Article 94 (3) EPC in connection with European Patent Application No. EP 11848220.7.
Dec. 28, 2012 Amendment In Response To Office Action dated Jun. 28, 1012 in connection with U.S. Appl. No. 12/308,091.
Eid et al. (2008) "Real-Time DNA Sequencing from Single Polymerase Molecules", Science, 23 (5910):133-138 (2008).
Ervin, et al. Simultaneous alternating and direct current readout of protein ion channel blocking events using glass nanopore membranes. Anal Chem. Mar. 15, 2008; 80(6):2069-76. Epub Feb. 23, 2008.
Extended European Search Report dated Mar. 11, 2016 by the EPO in connection with EP 13775787.8.
Extended European Search Report dated Mar. 11, 2016 by the EPO in connection with EP 13807639.3.
Feb. 3, 2016 Office Action issued in connection with Chinese Patent Application No. 200780028545.1.
Feb. 9, 2017 Communication Pursuant to Article 94 (3) EPC, issued by che European Patent Office in connection with EP 13775787.8.
Fologea, D. et al. (2005) "Detecting Single Stranded DNA with a Solid State Nanopore" Nano Letters 5(10):1905-1909.
Fologea, D. et al. (2005) "Slowing DNA Translocation in a Solid State Nanopore" Nano Letters 5(9), 1734-1737.
Fuller et al., "Real-time single-molecule electronic DNA sequencing by synthesis using polymer-tagged nucleotides on a nanopore array", PNAS, vol. 113, No. 19, pp. 5233-5238, published May 10, 2016; doi/10.1073.
Guo et al., "An Integrated System for DNA Seqeuncing by Synthesis Using Novel Nucleotide Analogues", Accounts of Chem. Res. vol. 43, No. 4, Apr. 20, 2010, pp. 551-563, XP55032473, ISSN: 0001-4842, DOI: 10.1021/ar900255c.
Guranowski et al. (2000) "Selective Degradation of 2'-Adenylated Diadenosine Tri- and Tetraphosphates, Ap3A, by Two Specific Human Dinucleoside Polyphosphate Hydrolases", Archives of Biochemistry and Biophysics, 373(1):218-224.
Heng, J.B. et al. (2005) "Stretching DNA Using the Electric Field in a Synthetic Nanopore" Nano Letters 5(9):1734-1737.
Heng, J.B. et al. (2006) "The Electromechanics of DNA in a synthetic nanopore" Biophysical Journal 90:1098-1106.
Henrickson, S.E. et al. (2000) "Driven DNA Transport into an Asymmetric Nanometer-scale Pore" Physical Review Letters 85:3057-3060.
International Preliminary Report on Patentability (Chapter II of the Patent Cooperation Treaty), dated Mar. 6, 2016 in connection with PCT International Application No. PCT/US2015/022063.
International Search Report and Written Opinion of the International Searching Authority issued by the International Searching Authority (ISA/US) dated Oct. 29, 2007 in connection with International Application No. PCT/US2007/013559.
International Search Report and Written Opinion of the International Searching Authority dated Oct. 25, 2013 PCT/US2013/035635.
International Search Report and Written Opinion of the International Searching Authority dated Sep. 24, 2013 in connection with PCT International Application No. PCT/US2013/035630.
International Search Report and Written Opinion of the International Searching Authority dated Jul. 30, 2014 in connection with PCT International Application No. PCT/US2014/029495.
International Search Report and Written Opinion of the International Searching Authority dated Jun. 29, 2015 in connection with PCT International Application No. PCT/US2015/022063.
International Search Report and Written Opinion of the International Searching Authority dated Aug. 25, 2015 in connection with PCT International Application No. PCT/US2015/015647.
Invitation Pursuant to Rule 62a(1) EPC, dated Oct. 7, 2016 in connection with EP14764268.0, Ju et al.
Invitation to Pay Additional Fees mailed by the International Searching Authority dated Aug. 19, 2013 connection with PCT International Application No. PCT/US2013/035635.
Jan. 15, 2016 Communication Pursuant to Article 94(3) EPC in connection ith European Patent Application No. EP 11848220.7.
Jan. 26, 2014 Request for Reexamination filed in connection with Chinese Patent Application No. 200780028545.1.
Jan. 29, 2016 Office Action issued in connection with Chinese Patent Application No. 201180063978.7.

(56) References Cited

OTHER PUBLICATIONS

Jan. 6, 2012 Response to First Office Action filed in connection with hinese Patent Application No. 200780028545.1.
Ju et al. (2006) "Four-color DNA Sequencing by Synthesis using Cleavable Fluorescent Nucleotide Reversible Terminators", PNAS, 103 (52):19635-19640.
Jul. 13, 2015 Third Office Action in connection with Chinese Patent Application No. 201180063978.7 (with English translation of cover page only).
Jul. 15, 2015 Communication pursuant to Article 94(3) EPC in connection with European Patent Application No. EP 11848220.7.
Jul. 17, 2014 Notice of Allowance issued in connection with U.S. Appl. No. 12/308,091.
Jul. 18, 2017 Restriction Requirement issued in connection with U.S. Appl. No. 14/666,124, Fuller et al.
Jul. 19, 2016 Amendment' filed in Response to the May 4, 2016 Office Action issued by the State Intellectual Property Office of the People's Republic of China in connection with Chinese Patent Application No. 201380025837.5.
Jul. 2, 2012 Office Action in connection with Chinese Patent Application No. 200780028545.1.
Jul. 29, 2016 Notice on Grant of Patent Right for Invention, issued in connection with Chinese Patent Application No. 201180063978.7 (English Translation).
Jun. 21, 2013 Response to Third Office Action filed in connection with Chinese Patent Application No. 200780028545.1.
Jun. 22, 2011 Office Action in connection with Chinese Patent Application No. 200780028545.1 (with English translation of cover page only).
Jun. 23, 2011 Restriction Requirement dated Jun. 23, 2011 in connection with U.S. Appl. No. 12/308,091.
Jun. 29, 2016 Office Action issued in connection with Chinese Patent Application No. 200780028545.1.
Jun. 5, 2018 Amendment in Response to the Dec. 6, 2017 Non-Final ffice Action issued by the United States Patent and Trademark Office in connection with U.S. Appl. No. 14/391,320.
Jun. 7, 2018 Amendment in Response to the Nov. 9, 2017 Extended European Search Report issued by the European Patent Office in connection with EP 15768383.0, fuller et al.
Kang et al. A storable encapsulated bilayer chip containing a single protein nanopore. J Am Chem Soc. Apr. 18, 2007; 129(15):4701-5. Epub Mar. 22, 2007.
Kasianowicz, J.J. (2003) "Nanometer-scale pores: potential applications for DNA characterization and analyte detection." Disease Markers 18:185-191.
Kasianowicz, J.J. (2004) "Nanopore. Flossing with DNA" Nature Materials 3:355-356.
Kasianowicz, J.J. et al. (1996) "Characterization of Individual Polynucleotide Molecules Using a Membrane Channel," Proc. Natl. Acad. Sci. USA 93:13770-13773.
Kawano et al. Controllng the translocation of single-stranded DNA through alpha-hemolysin ion channels using viscosity. Langmuir. Jan. 20, 2009; 25(2):1233-7.
Kumar et al. (2005) "Terminal phosphate labeled nucleotides: Synthesis, applications, and linker effect on incorporation by DNA polymerases", Nucleosides, Nucleotides, and Nucleic Acids, 24(5-7):401-108.
Kumar et al. PEG-labeled nucleotides and nanopore detection for single molecule DNA sequencing by synthesis. Sci Rep. 2012; 2:684. Epub Sep. 21, 2012.
Kutik et al. Dissecting membrane insertion of mitochondrial beta-barrel proteins. Cell. Mar. 21, 2008; 132(6):1011-24.
Li. L. et al. (2001) "Ion-beam sculpting at nanometre length scales" Nature 412:166-169.
Lieberman et al. "Processive Replication of Single DNA Molecules in a Nanopore Catalyzed by phi29 DNA Polymerase", Jol. ACS, vol. 132, No. 50, Dec. 22, 2010, pp. 17961-17972.
Madampage, et al. Nanopore detection of antibody prion interactions. Anal Biochem. Jan. 1, 2010; 396(1):36-41. Epub Aug. 21, 2009.

Mar. 16, 2016 Restriction Requirement issued in connection with U.S. Appl. No. 14/391,337.
Mar. 24, 2015 Office Action issued in connection with Chinese Patent Application No. 200780028545.1.
Mar. 27, 2014 Office Action in connection with Chinese Patent Applicatior No. 201180063978.7.
Mar. 31, 2016 Response to the Jan. 29, 2016 Office Action issued in connection with Chinese Patent Application No. 201180063978.7.
Mar. 6, 2015 Response to Dec. 22, 2014 Second Office Action in connection with Chinese Patent Application No. 201180063978.7.
Mar. 7, 2018 Non-Fnal Office Action issued in connection with U.S. Appl. No. 14/666,124, Fuller et al.
Mauer et al. Reconstitution of ion channels in agarose-supported silicon orifices. Biosens Bioelectron. May 15, 2007; 22(11):2577-84. Epub Nov. 13, 2006.
May 12, 2016 Amendment in Response to Communication Pursuant to Article 94(3) in connection with European Patent Application No. EP 11848220.7, Ju et al.
May 4, 2015 Amendment in response to Dec. 23, 2014 Communication pursuant to Article 94 (3) EPC in connection with European Patent Application No. EP 11848220.7.
May 4, 2016 Office Action issued by the Chinese State Intellectual Property Office in connection with Chinese Patent Application No. 201380025837.5.
McNally et al. Optical recognition of converted DNA nucleotides for single-molecule DNA sequencing using nanopore arrays. Nano Lett. Jun. 9, 2010; 10(6):2237-44.
Meller, A. et al. (2000) "Rapid nanopore discrimination between single polynucleotide molecules." Proc. Natl. Acad. Sci. USA 97:1079-1084.
Meller, A. et al. (2002) "Single Molecule Measurements of DNA Transport Through a Nanopore" Electrophoresis 23:2583-2591.
Mohammad et al. Controlling a single protein in a nanopore through electrostatic traps. J Am Chem Soc. Mar. 26, 2008; 130(12):4081-8. Epub Mar. 6, 2008.
Mulder et al. (2005) "Nucleotide modification at the γ-phosphate leads to the improved fidelity of HIV-1 reverse transcriptase", Nucleic Acids, Research, 33(15):4865-4873.
Nakane et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Notice on Grant of Patent Right for Invention dated Oct. 10, 2016 by the Chinese Patent Office in connection with Chinese Patent Application No. 200780028545.1, English translation.
Notification Concerning Transmittal of International Preliminary Report on Patentability, dated Dec. 24, 2008 in connection with International Application No. PCT/US07/13559.
Notification of Transmittal of the International Search Report and the Written Opinion of the International Searching Authority, or the Declaration, including an International Search Report and Written Opinion of the International Searching Authority, dated Feb. 4, 2013 in connection with PCT International Application No. PCT/US2011/065640, filed Dec. 16, 2011.
Nov. 13, 2015 Decision on Reexamination issued in connection with Chinese Patent Application No. 200780028545.1.
Nov. 14, 2014 Response to Apr. 16, 2014 Communication transmitting Supplementary European Search Report and European Search Opinion in connection with European Patent Application No. EP 11848220.7.
Nov. 19, 2012 Response to Second Office Action filed in connection with Chinese Application No. 200780028545.1.
Nov. 20, 2017 Amendment in Response to Restriction Requirement issued in connection with U.S. Appl. No. 14/666,124, Fuller et al.
Nov. 9, 2017 Extended European Search Report issued by the European Patent Office in connection with EP 15768383.0, Fuller et al.
Oct. 10, 2016 Amendment in Response to the Extended European Search Report dated Mar. 11, 2016 by the EPO in connection with EP 13775787.8.
Oct. 10, 2016 Amendment in Response to the Extended European Search Report dated Mar. 11, 2016 by the EPO in connection with EP 13807639.3.

(56) References Cited

OTHER PUBLICATIONS

Oct. 12, 2013 Decision of Rejection issued in connection with Chinese Patent Application No. 200780028545.1.
Oct. 24, 2011 Response to Restriction Requirement dated Jun. 23, 2011 in connection with U.S. Appl. No. 12/308,091.
Office Action dated Jul. 15, 2015 by the Chinese State Intellectual Property Office in connection with Chinese Patent Application No. 201380025837.5.
Office Action dated Jul. 26, 2016 by the Chinese State Intellectual Property Office in connection with CN 201480015937.4.
Office Action dated Jun. 28, 2012 in connection with U.S. Appl. No. 12/308,091.
Office Action dated Nov. 29, 2011 in connection with U.S. Appl. No. 12/308,091.
Office Action dated Oct. 26, 2016 in connection with U.S. Appl. No. 14/391,337, Ju et al.
Park et al. DNA hybridization sensors based on electrochemical impedance spectroscopy as a detection tool. Sensors (Basel). 2009; 9(12):9513-32. Epub Nov. 26, 2009.
Pending claims in U.S. Appl. No. 11/922,385, filed Jul. 29, 2009 by Ju et al. (published as 2009/0325154 A1, Dec. 31, 2009).
Pending claims in U.S. Appl. No. 12/734,229, filed Nov. 3, 2010 by Ju et al. (published as U.S. Patent Application Publication No. 2011/0039259 A1, published Feb. 17, 2011).
Pending claims in U.S. Appl. No. 13/186,353, filed Jul. 19, 2011 by Ju et al (published as 2012/0156680 A1, Jun. 21, 2012).
Perkins, T.T. et al. (1994) "Relaxation of a single DNA molecule observed by optical microscopy" Science 264:822-826.
Pourmand N. et al. (2002) "Multiplex Pyrosequencing" Nucleic Acids Research 30(7):1-5.
Response to Restriction Requirement filed on May 4, 2017 in connection with U.S. Appl. No. 14/391,320, Ju et al.
Response to the Jul. 15, 2015 Office Action, filed Jan. 29, 2016 in connection with Chinese Patent Application No. 201380025837.5.
Restriction Requirement dated Jan. 5, 2017 in connection with U.S. Appl. No. 14/391,320, Ju et al.
Reynolds et al. (2008) "Synthesis and Stability of Novel Terminal Phosphate-labeled Nucleotides", Nucleosides, Nucleotides, and Nucleic Acids, 27(1):18-30.
Rief, M. (1999) "Sequence-dependent mechanics of single DNA molecules" Mat. Struct. Biol. 6:346-349.
Robertson et al., (2007) "Single-Molecule Mass Spectrometry in Solution Ising a Solitary Nanopore" PNAS, 104(20):8207-8211.
Rothberg, J.M. et al. (2011) "An integrated semiconductor device enabling non-optical genome sequencing" *Nature* 475:348-352.
Sanchez-Magraner, et al. Membrane insertion of *Escherichia coli* alpha-hemolysin is independent from membrane lysis. J Biol Chem. Mar. 3, 2006; 281(9):5461-7. Epub Dec. 22, 2005.
Sauer-Budge, A.F. et al. (2003) "Unzipping Kinetics of Double Stranded DNA in a Nanopore" Physical Review Letters 90(23):238101-1-238101-4.
Second Communication Under Rule 71(3) EPC, issued by the European Patent Office in connection with European Patent Application No. EP11848220.7 dated Feb. 7, 2017, Ju et al.
Seo et al., (2004) "Photocleavable Fluorescent Nucleotides for DNA Sequencing on a Chip Constructed by Site-Specific Coupling Chemistry," PNAS 101(15):5488-5493.
Sep. 13, 2016 Amendment in Response to the Jun. 29, 2016 Office Action issued in connection with Chinese Patent Application No. 200780028545.1.
Sep. 16, 2016 Response to the Mar. 16, 2016 Restriction Requirement issued in connection with U.S. Appl. No. 14/391,337.
Sep. 28, 2015 Response to Jul. 13, 2015 Office Action issued in connection with Chinese Patent Application No. 201180063978.7.
Sep. 8, 2015 Response to Mar. 24, 2015 Office Action issued in connection with Chinese Patent Application No. 200780028545.1.
Shim et al., Encapsulating a single G-quadruplex aptamer in a protein nanocavity. J Phys Chem B. Jul. 17, 2008; 112(28):8354-60. Epub Jun. 19, 2008.
Simon et al., Formation and stability of a suspended biomimetic lipid bilayer on silicon submicrometer-sized pores. J Colloid Interface Sci. Apr. 15, 2007; 308(2):337-43. Epub Jan. 31, 2007.
Singer et al. Nanopore Based Sequence Specific Detection of Duplex DNA for Genomic Profiling, Jan. 8, 2010, published Jan. 20, 2010, pp. 738-742.
Smith, S.B. et al. (1996) "Overstretching B-DNA: the elastic response of individual double-stranded and single-stranded DNA molecules." Science 271:795-799.
Sood et al. (2005) "Terminal phosphate-labeled nucleotides with improved substrate properties for homogenous nucleic acid assays", JACS, 127(8):2394-2395.
Stefureac et al. Nanopore analysis of the interaction of metal ions with prion proteins and peptides. Biochem Cell Biol. Apr. 2010; 88(2):347-58.
Sterfureac et al. Transport of alpha-helical peptides through alpha-hemolysin and aerolysin pores. Biochemistry. Aug. 1, 2006; 45(30):9172-9.
Stoddart et al. Nucleobase recognition in ssDNA at the central constriction of the alpha-hemolysin pore. Nano Lett. Sep. 8, 2010; 10(9):3633-7.
Stoddart et al. Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Stranges et al., "Design and characterization of a nanopore-coupled polymerase for single-molecule DNA sequencing by synthesis on an electrode array", Proc Natl Acad Sci USA, Oct. 11, 2016. doi:10/1073/PNAS.1608271113.
Streater M et al., (Novel 3-hydroxy-2 (IH)-pyridinones. Synthesis, iron (III)-chelating properties, and biological activity. J. Medicinal Chem. (1990) 33(6):1749-1755.
Studer et al., Formation of individual protein channels in lipid bilayers suspended in nanopores. Colloids Surf B Biointerfaces., Oct. 15, 2009; 73(2):325-31. Epub Jun. 10, 2009.
Suzuki et al., Highly reproducible method of planar lipid bilayer reconstitution in polymethyl methacrylate microfluidic chip. , Feb. 2006, Langmuir. 22(4):1937-42.
Thomson et al., Preliminary nanopore cheminformatics analysis of aptamer-target binding strength, Nov. 2007, BMC Bioinformatics. 1; 8 Suppl 7:S11.
Vercoutere, W. et al. (2001) "Rapid discrimination among individual DNA hairpin molecules at single-nucleotide resolution using an ion channel." Nat. Biotech 19:248-252.
Viasnoff et al., Probing DNA base pairing energy profiles using a nanopore. Eur Biophys J., Feb. 2009, 38(2):263-9. Epub Oct. 3, 2008.
Voluntary Amendment filed Mar. 17, 2016 in connection with Chinese Patent Application No. CN 2014800159374.
Voluntary Amendment filed May 12, 2016 in connection with EP14764268.0, Ju et al.
Walker et al., "Key Residues for Membrane Binding, Oligomerization, and Pore Forming Activity of Staphylococcal alpha-hemolysin Identified by Cysteine Scanning Mutagenesis and Targeted Chemical Modification", J. Biol. Chem. 1995, doe: 10.1074/jbc.270.39.23065.
Wanunu et al., DNA profiling using solid-state nanopores: detection of DNA-binding molecules. Nano Lett. Oct. 2009; 9(10):3498-502.
Wei et al., "Stochastic sensing of proteins with receptor-modified solid-state nanopores" Nature Nanotechnology, 7(4):257-263 (2012).
Weng et al., Fluid biomembranes supported on nanoporous aerogel/xerogel substrates. Langmuir. Aug. 17, 2004; 20(17):7232-9.
Wilson et al., Feedback control of a DNA molecule tethered in a nanopore to repeatedly probe DNA-binding enzymes. Conf Proc IEEE Eng Med Biol Soc. 2008; 2008:5745-8.
Winters-Hilt et al., Nanopore-based kinetics analysis of individual antibody-channel and antibody-antigen interactions. BMC Bioinformatics. Nov. 1, 2007; 8 Suppl 7:S20.
Wu et al., Single-molecule detection of nitrogen mustards by covalent reaction within a protein nanopore. J Am Chem Soc. May 28, 2008; 130(21):6813-9. Epub Apr. 30, 2008.

(56) References Cited

OTHER PUBLICATIONS

Zeineldin et al., Using bicellar mixtures to form supported and suspended lipid bilayers on silicon chips. Langmuir. Sep. 12, 2006; 22(19):8163-8.
Zwolak, et al. Electronic signature of DNA nucleotides via transverse transport. Nano Lett. Mar. 2005; 5(3):421-4.
First Office Action dated May 29, 2020 by the Chinese State Intellectual Property Office in connection with Chinese Paten Application No. 201610894651.9.
Response to First Office Action filed Jan. 13, 2021 with the Chinese State Intellectual Property Office in connection with Chinese Paten Application No. 201610894651.9.
Second Office Action dated Feb. 19, 2021 by the Chinese State Intellectual Property Office in connection with Chinese Paten Application No. 201610894651.9.
Response to Second Office Action filed Dec. 17, 2021 with the Chinese State Intellectual Property Office in connection with Chinese Paten Application No. 201610894651.9 including English language draft thereof.

\* cited by examiner

BASE= A, C, T, U, G, 7-deaza-A, 7-deaza-G or derivatives thereof
$R_1$ and $R_2$ = H or OH
TAG-OH= detectable moiety in the hydroxy form, such as, aliphatic or aromatic alcohols
TAG-COR= detectable moiety to react with the amino group, such as NHS esters, acid chloride etc BASE= A, C, T, U, G, 7-deaza-A, 7-deaza-G or derivatives thereof
$R_1$ and $R_2$ = H or OH
n=1-100
TAG= detectable moiety, such as, aliphatic or aromatic alcohols, aminoacids, dyes, carbohydrates, oligos etc
TAG-COR= detectable moiety to react with the amino group, such as NHS esters, acid chloride etc BASE= A, C, T, U, G, 7-deaza-A, 7-deaza-G or derivatives thereof
$R_1$ and $R_2$ = H or OH
X = O, NH, S or $CH_2$
TAG = detectable moiety, such as, aliphatic or aromatic alcohols, aminoacids, dyes, carbohydrates, oligos etc
TAG-COR = detectable moiety to react with the amino group, such as NHS esters, acid chloride etc i), N-propargyltrifluoroacetamide, Pd(PPh₃)₄, CuI, Et₃N, DMF, r.t. 10hrs; ii), DMSO, Ac₂O, AcOH, r. t. 48 hrs; iiia), cyclohexene, SO₂Cl₂, CH₂Cl₂ 0°-r. t. 1h; iiib), NaN₃, DNF, r. t. 4hrs, iv), TBAF; v), POCl₃, (MeO)₃PO, (Bu₃NH)₂H₂P₂O₇, TEAB, Bu₃N, NH₄OH;
vi), ClC(O)OCH₂CHN₃CONHCH₂CH₂NHCO-PEG vii), NH₄OH-MeOH Phosphate-tagged nucleotides Base-tagged nucleotides 3'-O-tagged nucleotides 2'-O-tagged nucleotides Coumarin based fluorogenic dyes Resorufin based fluorogenic dyes DDAO based fluorogenic dyes Fluorescein based fluoroogenic dyes Nitrophenyl based chromogenic dyes Indole based chromoogenic dyes Array of Nanopores for Sequencing by Synthesis Released PEG or PEG-phosphates after polymerase incprporation:

n= 15, 23, 36 and 48

Synthesis of first generation PEG tag-nucleotides

Extension Reaction with dG4P-PEG24

Extension Reaction with dG4P -PEG37

Linear PEGs n= 27-33 n=27; dPEG$_{30}$: 30 ethylene glycol units    For T
n=29; dPEG$_{32}$: 32 ethylene glycol units    For G
n=31; dPEG$_{34}$: 34 ethylene glycol units    For C
n=33; dPEG$_{36}$: 36 ethylene glycol units    For A

Branched PEGs

R = NH$_2$, OH, COOH, COOR', CHO, SH, N$_3$

Synthesis of phosphate-tagged nucleoside-5'-triphosphates

Synthesis of phosphate-tagged nucleoside-5'-tetraphosphates

Synthesis of terminal phosphate-tagged nucleoside-5'-pentaphosphates

BASE= A, C, T, U, G, 7-deaza-A, 7-deaza-G or derivatives thereof
$R_1$ and $R_2$ = H or OH
X= O, S, NH; n= 2, 3, 4
TAG-OH/ $NH_2$= detectable moiety, such as, aliphatic or aromatic alcohols or amines
TAG-COR= detectable moiety to react with the amino group, such as NHS esters, acid chloride etc Synthesis of 3'-O-blocked-PEG-nucleotides

DNA SEQUENCING BY SYNTHESIS USING MODIFIED NUCLEOTIDES AND NANOPORE DETECTION

This application is a divisional of U.S. application Ser. No. 13/994,431, filed Oct. 22, 2014, now allowed, which is a § 371 national stage of PCT International Application No. PCT/US2011/065640, filed Dec. 16, 2011, claiming the benefit of U.S. Provisional Application No. 61/424,480, filed Dec. 17, 2010, and U.S. Provisional Application No. 61/557,558, filed Nov. 9, 2011, the content of each of which is hereby incorporated by reference in its entirety.

Throughout this application, certain patents and publications are referenced, the latter by authors and publication year. Full citations for these publications may be found immediately preceding the claims. The disclosures of these patents and publications in their entireties are hereby incorporated by reference into this application in order to describe more fully the state of the art to which this invention relates.

BACKGROUND OF THE INVENTION

DNA sequencing is a fundamental technology for biology. Several analytical methods have been developed to detect DNA or RNA at single molecule level using chemical or physical microscopic technologies [Perkins et al. 1994, Rief et al. 1999, Smith et al. 1996, and Vercoutere et al. 2001].

In the past few years, ion-sensing technologies such as ion channel, which relies on the detection of hydrogen ion ($H^+$) released when a nucleotide is incorporated into a strand of DNA by a polymerase [Rothberg et al. 2011], have been explored to detect individual DNA or RNA strands [Kasianowicz 2003 & 2004, Chandler et al. 2004, Deamer et al. 2002, Berzukov et al. 2001, and Henrickson et al. 2000].

It has been demonstrated that an α-hemolysin channel, an exotoxin secreted by a bacterium, can be used to detect nucleic acids at the single molecule level [Kasianowicz et al. 1996]. An α-hemolysin protein is a monomeric polypeptide which self-assembles in a lipid bilayer membrane to form a heptameric pore, with a 2.6 nm-diameter vestibule and 1.5 nm-diameter limiting aperture (the narrowest point of the pore) [Meller et al. 2000, Akeson et al. 1999, and Deamer et al. 2002]. The limiting aperture of the nanopore allows linear single-stranded but not double-stranded, nucleic acid molecules (diameter ~2.0 nm) to pass through. In an aqueous ionic salt solution such as KCl, when an appropriate voltage is applied across the membrane, the pore formed by an α-hemolysin channel conducts a sufficiently strong and steady ionic current. The polyanionic nucleic acids are driven through the pore by the applied electric field, thus blocking or reducing the ionic current that would be otherwise unimpeded. This process of passage generates an electronic signature (FIG. 1) [Vercoutere et al. 2001 and Deamer et al. 2002]. A particular nucleic acid molecule, when entering and passing through the nanopore generates a characteristic signature that distinguishes it from other nucleic acid molecules. The duration of the blockade is proportional to the length of nucleic acid, and the signal strength is related to the steric and electronic properties of the nucleotides, namely the identity of the four bases (A, C, G and T). Thus a specific event diagram, which is a plot of translocation time versus blockade current, is obtained and used to distinguish the length and the composition of polynucleotides by single-channel recording techniques based on characteristic parameters such as translocation current, translocation duration, and their corresponding dispersion in the diagram [Meller et al. 2000].

It has also been shown that a protein nanopore with a covalently attached adaptor can accurately identify unlabeled nucleoside 5'-monophosphates (dAMP, dGMP, dCMP & dTMP) with high accuracy [Clarke et al. 2009]. For example, aminocyclodextrin adaptor has been covalently attached within the α-hemolysin pore successfully. When a dNMP is captured and driven through the pore in a lipid bilayer membrane, the ionic current through the pore is reduced to one of four levels, each representing one of the four dNMP's (A, G, C, or T). Moreover, Robertson et al. [2007] have recently demonstrated that when a poly(ethylene glycol) (PEG) molecule enters a single α-hemolysin pore, it causes distinct mass-dependent conductance states with characteristic mean residence times. The conductance-based mass spectrum clearly resolves the repeat units of ethylene glycol, and the residence time increases with the mass of the PEG.

Although the current nanopore approach shows promise as a DNA detection method, the more demanding goal of accurate base-to-base sequencing has not yet been achieved.

SUMMARY OF THE INVENTION

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and four deoxyribonucleotide polyphosphate (dNPP) analogues at least one of which can hybridize with each of an A, T, G, or C nucleotide in the DNA being sequenced under conditions permitting the DNA polymerase to catalyze incorporation of one of the dNPP analogues into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein each of the four dNPP analogues has the structure:

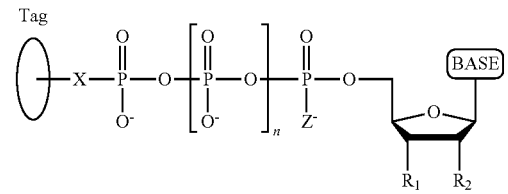

wherein the base is adenine, guanine, cytosine, thymine or uracil, or a derivative of one or more of these bases, wherein $R_1$ is OH, wherein $R_2$ is H, wherein X is O, NH, S or $CH_2$, wherein n is 1, 2, 3, or 4, wherein Z is O, S, or $BH_3$, and with the proviso that (i) the type of base on each dNPP analogue is different from the type of base on each of the other three dNPP analogues, and (ii) either the value of n of each dNPP analogue is different from the value of n of each of the other three dNPP analogues, or the value of n of each of the four dNPP analogues is the same and the type of tag on each dNPP analogue is different from the type of tag on each of the other three dNPP analogues, wherein incorporation of the dNPP analogue results in release of a polyphosphate having the tag attached thereto; and (b) identifying which dNPP analogue has been incorporated into the primer to form a DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, whichever is applicable, thereby permitting identifying the nucleotide residue in the single-stranded DNA complementary to the incorporated dNPP analogue; and (c) repeatedly performing step (b) for each nucleotide residue of the single-stranded DNA being sequenced, wherein in each repetition of step (b) the dNPP analogue is incorporated into the DNA extension product if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, a DNA polymerase and a deoxyribonucleotide polyphosphate (dNPP) analogue under conditions permitting the DNA polymerase to catalyze incorporation of the dNPP analogue into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the dNPP analogue has the structure:

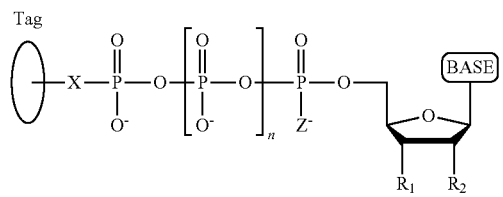

wherein the base is adenine, guanine, cytosine, uracil or thymine, or a derivative of each thereof, wherein $R_1$ is —OH, —O—$CH_2N_3$ or —O-2-nitrobenzyl, wherein $R_2$ is H, wherein X is O, NH, S or $CH_2$, wherein n is 1, 2, 3, or 4, wherein Z is O, S, or $BH_3$, and wherein if the dNPP analogue is not incorporated, iteratively repeating the contacting with a different dNPP analogue until a dNPP analogue is incorporated, with the proviso that (1) the type of base on each dNPP analogue is different from the type of base on each of the other dNPP analogues, and (2) either the value of n of each dNPP analogue is different from the value of n of each of the other three dNPP analogues, or the value of n of each of the four dNPP analogues is the same and the type of tag on each dNPP analogue is different from the type of tag on each of the other three dNPP analogues, wherein incorporation of a dNPP analogue results in release of a polyphosphate having the tag attached thereto;

(b) determining which dNPP analogue has been incorporated into the primer to form a DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, as appropriate, thereby identifying the nucleotide residue in the single-stranded DNA complementary to the incorporated dNPP analogue;

(c) repeatedly performing steps (a) and (b) for each nucleotide residue of the single-stranded DNA being sequenced, wherein in each repetition of step (a) the dNPP analogue is incorporated into the DNA extension product if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and at least four deoxyribonucleotide polyphosphate (dNPP) analogues under conditions permitting the DNA polymerase to catalyze incorporation of one of the dNPP analogues into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein each of the four dNPP analogues has a structure chosen from the following:

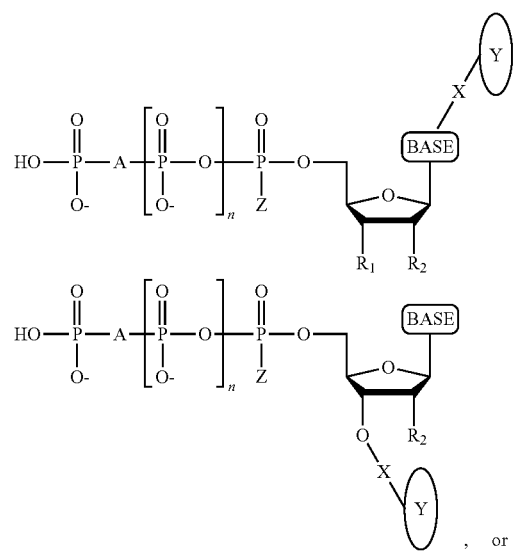

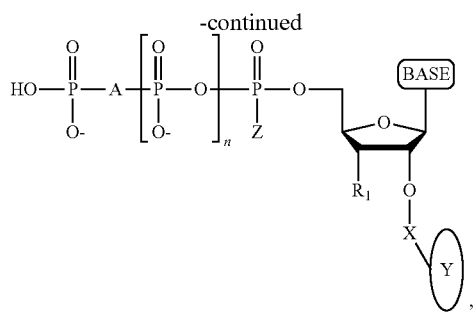

wherein the base is adenine, guanine, cytosine, thymine or uracil, or a derivative of each thereof, wherein Y is a tag, wherein $R_1$, if present, is OH, wherein $R_2$, if present, is H, wherein X is a cleavable linker, wherein Z is O, S or $BH_3$, wherein n is 1, 2, 3, or 4, wherein A is O, S, $CH_2$, CHF, CFF, or NH, and with the proviso that (i) the type of base on each dNPP analogue is different from the type of base on each of the other three dNPP analogues, and (ii) the type of tag on each dNPP analogue is different from the type of tag on each of the other three dNPP analogues;

(b) cleaving the tag from the dNPP analogue incorporated in step (a); and (c) determining which dNPP analogue was incorporated in step (a) by applying a voltage across the membrane and measuring an electronic change across the nanopore resulting from tag cleaved off in step (b) translocating through the nanopore, wherein the electronic change is different for each different type of tag, thereby identifying the nucleotide residue in the single-stranded DNA complementary to the incorporated dNPP analogue; and (d) repeatedly performing steps (a), (b) and (c) for each nucleotide residue of the single-stranded DNA being sequenced, wherein in each repetition of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane, wherein the single-stranded DNA has a primer hybridized to a portion thereof, a DNA polymerase and a deoxyribonucleotide polyphosphate (dNPP) analogue under conditions permitting the DNA polymerase to catalyze incorporation of the dNPP analogue into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the dNPP analogue has the structure:

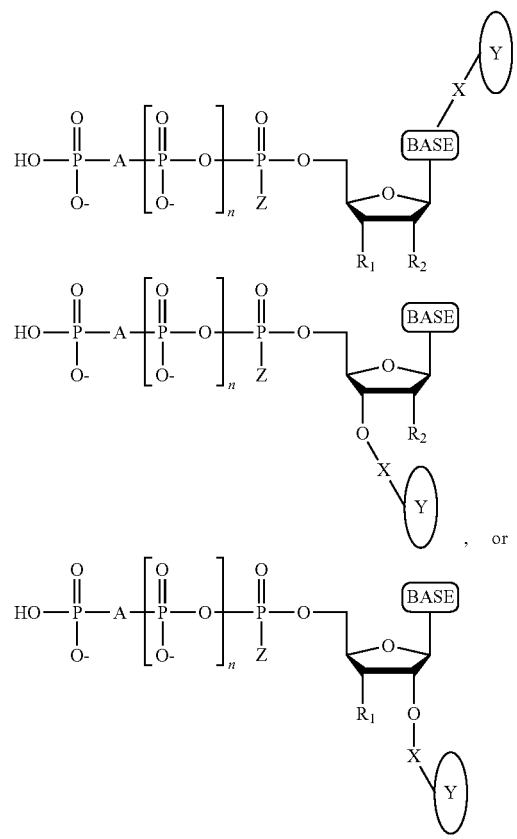

wherein the base is adenine, guanine, cytosine, uracil or thymine, or a derivative of each thereof, wherein Y is a tag, and wherein $R_1$ if present is OH, —$OCH_2N_3$ or —O-2-nitrobenzyl, $R_2$ if present is H, wherein X is a cleavable linker, wherein Z is O, S or $BH_3$, wherein n is 1, 2, 3, or 4, wherein A is O, S, $CH_2$, CHF, CFF, or NH, and if the dNPP analogue is not incorporated, iteratively repeating the contacting with a different dNPP analogue until a dNPP analogue is incorporated, with the proviso that (1) the type of base on each dNPP analogue is different from the type of base on each other dNPP analogue, and (2) the type of tag on each dNPP analogue is different from the type of tag on each other dNPP analogue, wherein incorporation of a dNPP analogue results in release of a polyphosphate having the tag attached thereto;

(b) cleaving the tag from the dNPP analogue incorporated in step (a); and (c) determining which dNPP analogue was incorporated in step (a) to form a DNA extension product by applying a voltage across the membrane and measuring an electronic change across the nanopore resulting from the tag cleaved off in step (b) translocating through the nanopore, wherein the electronic change is different for each type of tag, thereby identifying the nucleotide residue in the single-stranded DNA complementary to the incorporated dNPP analogue;

(d) iteratively performing steps (a) through (c) for each nucleotide residue of the single-stranded DNA being sequenced, wherein in each iteration of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A process for producing a nucleotide triphosphate analogue, wherein the nucleotide triphosphate analogue differs from a nucleotide triphosphate by having a tag attached to the terminal phosphate thereof, comprising:

a) contacting a nucleotide triphosphate with dicyclohexylcarbodiimide/dimethylformamide under conditions permitting production of a cyclic trimetaphosphate;
  b) contacting the product resulting from step a) with a tag having a hydroxyl or amino group attached thereto under conditions permitting nucleophilic opening of the cyclic trimetaphosphate so as to bond the tag to a terminal phosphate thereby forming the nucleotide triphosphate analogue.

A process for producing a nucleotide triphosphate analogue, wherein the nucleotide triphosphate analogue differs from a nucleotide triphosphate by having a tag attached to the terminal phosphate thereof, comprising:

a) contacting a nucleotide triphosphate with dicyclohexylcarbodiimide/dimethylformamide under conditions permitting production of a cyclic trimetaphosphate;
  b) contacting the product resulting from step a) with a nucleophile so as to form an —OH or —NH$_2$ functionalized compound;
  c) reacting the product of step b) with a tag having a —COR group attached thereto under conditions permitting the tag to bond indirectly to a terminal phosphate thereby forming the nucleotide triphosphate analogue.

A process for producing a nucleotide tetraphosphate analogue, wherein the nucleotide tetraphosphate analogue differs from a nucleotide tetraphosphate by having a tag attached to the terminal phosphate thereof, comprising:

a) contacting a nucleotide triphosphate with 1,1'-carbonyldiimidazole/dimethylformamide under conditions permitting formation of the following structure:

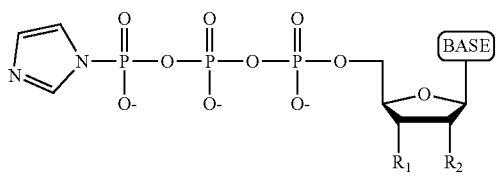

wherein R$_1$ is OH, wherein R$_2$ is H or OH, wherein the base is adenine, guanine, cytosine, thymine, uracil, a 7-deazapurine or a 5-methylpyrimidine;
  b) contacting the product resulting from step a) with a tag having a monophosphate group attached thereto under conditions permitting formation of the nucleotide tetraphosphate analogue.

A process for producing a nucleotide tetraphosphate analogue, wherein the nucleotide tetraphosphate analogue differs from a nucleotide tetraphosphate by having a tag attached to the terminal phosphate thereof, comprising:

a) contacting a nucleotide triphosphate with 1,1'-carbonyldiimidazole/dimethylformamide under conditions permitting formation of the following structure:

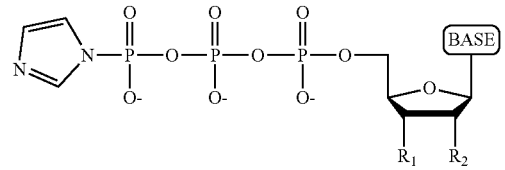

wherein R$_1$ is OH, wherein R$_2$ is H or OH, wherein the base is adenine, guanine, cytosine, thymine, uracil, a 7-deazapurine or a 5-methylpyrimidine;
  b) contacting the product resulting from step a) with phosphoric acid under conditions permitting formation of a nucleotide tetraphosphate;
  c) contacting the nucleotide tetraphosphate with 1) carbonyldiimidazole/dimethylformamide; 2) a nucleophile and then 3) NH$_4$OH so as to form an —OH or —NH$_2$ functionalized compound;
  d) contacting the product of step c) with a tag having a —COR group attached thereto under conditions permitting the tag to bond indirectly to a terminal phosphate thereby forming the nucleotide tetraphosphate analogue.

A process for producing a nucleotide tetraphosphate analogue, wherein the nucleotide tetraphosphate analogue differs from a nucleotide tetraphosphate by having a tag attached to the terminal phosphate thereof, comprising:

a) contacting a nucleotide triphosphate with 1,1'-carbonyldiimidazole/dimethylformamide under conditions permitting formation of the following structure:

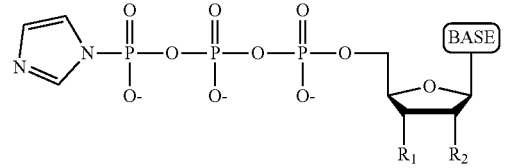

b) contacting the product resulting from step a) with phosphoric acid under conditions permitting formation of a nucleotide tetraphosphate;
  c) contacting the nucleotide tetraphosphate with carbonyldiimidazole/dimethylformamide and a tag having a hydroxyl or amino group attached thereto so as to form a compound having the structure:

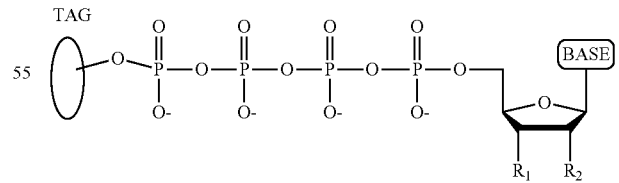

wherein R$_1$ is OH, wherein R$_2$ is H or OH, wherein the base is adenine, guanine, cytosine, thymine, uracil, a 7-deazapurine or a 5-methylpyrimidine.

A process for producing a nucleotide pentaphosphate analogue, wherein the nucleotide pentaphosphate analogue differs from a nucleotide pentaphosphate by having a tag attached to the terminal phosphate thereof, comprising:

a) contacting a nucleotide triphosphate with 1,1'-carbonyldiimidazole/dimethylformamide under conditions permitting formation of the following structure:

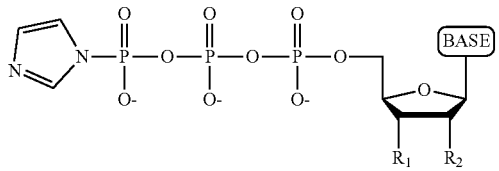

wherein $R_1$ is OH, wherein $R_2$ is H or OH, wherein the base is adenine, guanine, cytosine, thymine, uracil, a 7-deazapurine or a 5-methylpyrimidine;

b) contacting the product resulting from step a) with a tag having a pyrophosphate group attached thereto under conditions permitting formation of the nucleotide pentaphosphate analogue.

A process for producing a nucleotide pentaphosphate analogue, wherein the nucleotide pentaphosphate analogue differs from a nucleotide pentaphosphate by having a tag attached to the terminal phosphate thereof, comprising:

a) contacting a nucleotide triphosphate with 1,1'-carbonyldiimidazole/dimethylformamide under conditions permitting formation of the following structure:

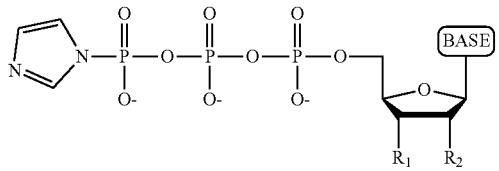

wherein $R_1$ is OH, wherein $R_2$ is H or OH, wherein the base is adenine, guanine, cytosine, thymine, uracil, a 7-deazapurine or a 5-methylpyrimidine;

b) contacting the product resulting from step a) with a pyrophosphate group under conditions permitting formation of a nucleotide pentaphosphate;

c) contacting the nucleotide pentaphosphate with carbonyldiimidazole/dimethylformamide and a tag having a hydroxyl or amino group attached thereto so as to form the nucleotide pentaphosphate analogue.

A process for producing a nucleotide hexaphosphate analogue, wherein the nucleotide hexaphosphate analogue differs from a nucleotide hexaphosphate by having a tag attached to the terminal phosphate thereof, comprising:

a) contacting a nucleotide triphosphate with 1,1'-carbonyldiimidazole/dimethylformamide under conditions permitting formation of the following structure:

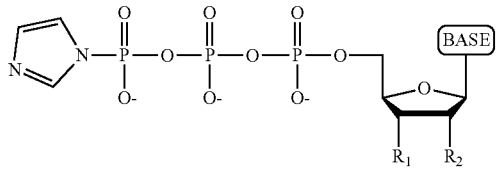

wherein $R_1$ is OH, wherein $R_2$ is H or OH, wherein the base is adenine, guanine, cytosine, thymine, uracil, a 7-deazapurine or a 5-methylpyrimidine;

b) contacting the product resulting from step a) with a tag having a triphosphate group attached thereto under conditions permitting formation of the nucleotide hexaphosphate analogue.

A process for producing a nucleotide hexaphosphate analogue, wherein the nucleotide hexaphosphate analogue differs from a nucleotide hexaphosphate by having a tag attached to the terminal phosphate thereof, comprising:

a) contacting a nucleotide triphosphate with 1,1'-carbonyldiimidazole/dimethylformamide under conditions permitting formation of the following structure:

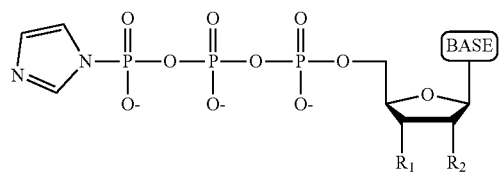

wherein $R_1$ is OH, wherein $R_2$ is H or OH, wherein the base is adenine, guanine, cytosine, thymine, uracil, a 7-deazapurine or a 5-methylpyrimidine;

b) contacting the product resulting from step a) with a triphosphate group under conditions permitting formation of a nucleotide hexaphosphate;

c) contacting the nucleotide hexaphosphate with carbonyldiimidazole/dimethylformamide and a tag having a hydroxyl or amino group attached thereto so as to form the nucleotide hexaphosphate analogue.

A compound having the structure:

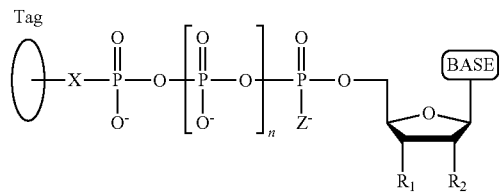

wherein the tag is ethylene glycol, an amino acid, a carbohydrate, a dye, mononucleotide, dinucleotide, trinucleotide, tetranucleotide, pentanucleotide or hexanucleotide, wherein $R_1$ is OH, wherein $R_2$ is H or OH, wherein X is O, NH, S or $CH_2$, wherein Z is O, S, or $BH_3$, wherein the base is adenine, guanine, cytosine, thymine, uracil, a 7-deazapurine or a 5-methylpyrimidine, and wherein n is 1, 2, 3, or 4.

A compound having the structure:
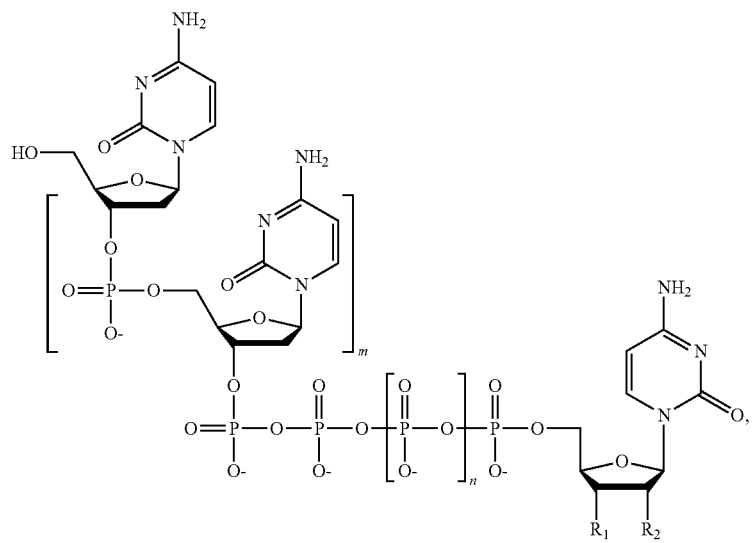
(dCp)$_m$-(PO$_4$)$_n$-dC
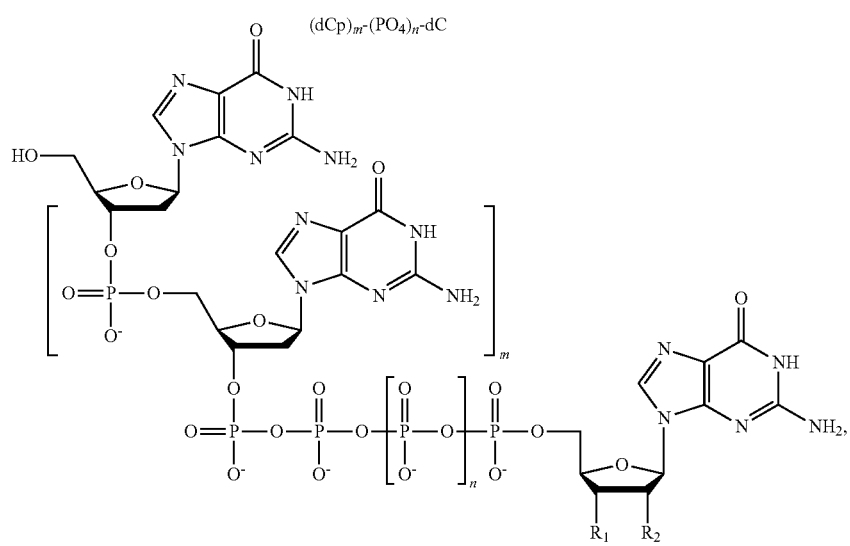
(dGp)$_m$-(PO$_4$)$_n$-dG
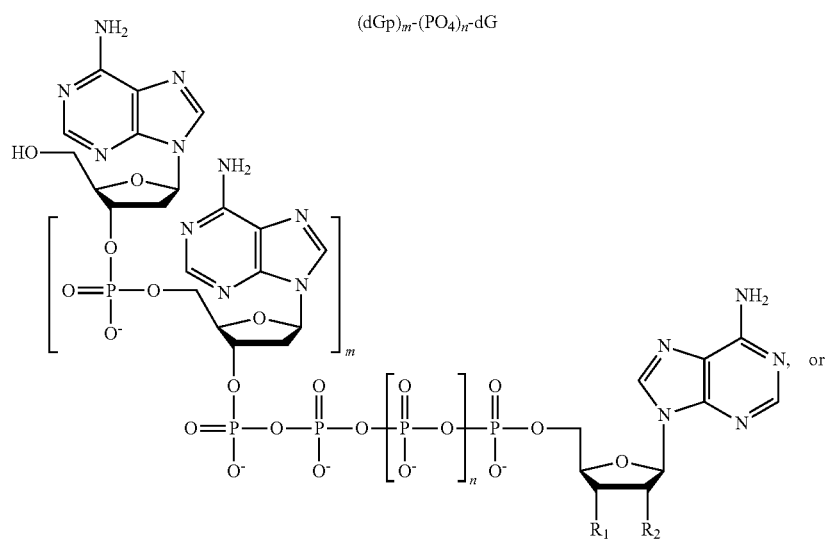
(dAp)$_m$-(PO$_4$)$_n$-dA

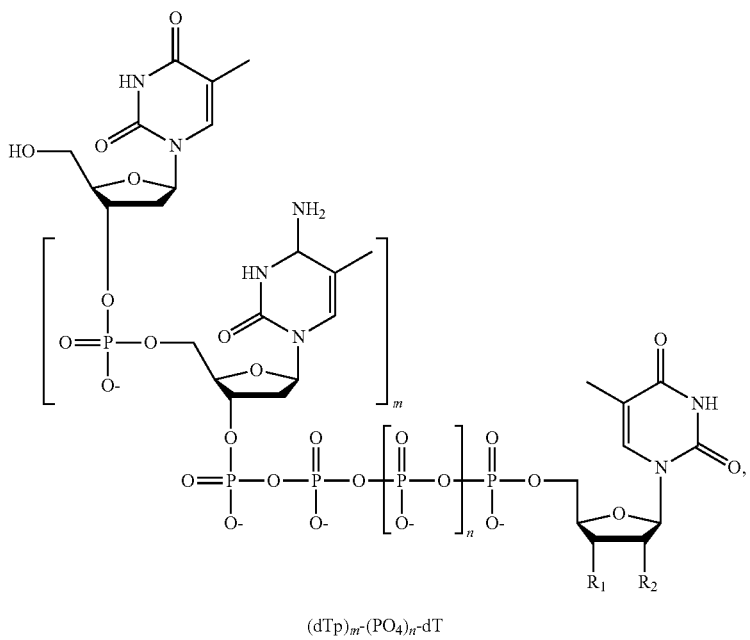

$(dTp)_m\text{-}(PO_4)_n\text{-}dT$ wherein in each structure n is, independently, 1, 2, 3 or 4, and m is, independently, an integer from 0 to 100, and wherein when m is 0 the terminal phosphate of the dNPP is bonded directly to the 3' O atom of the nucleoside shown on the left hand side of the structure, wherein $R_1$ is —OH, or —O—$CH_2N_3$, and $R_2$ is H or OH.

A composition comprising at least four deoxynucleotide polyphosphate (dNPP) analogues, wherein each of the four dNPP analogues comprises a type of base different from the type of base of the other three dNPP analogues.

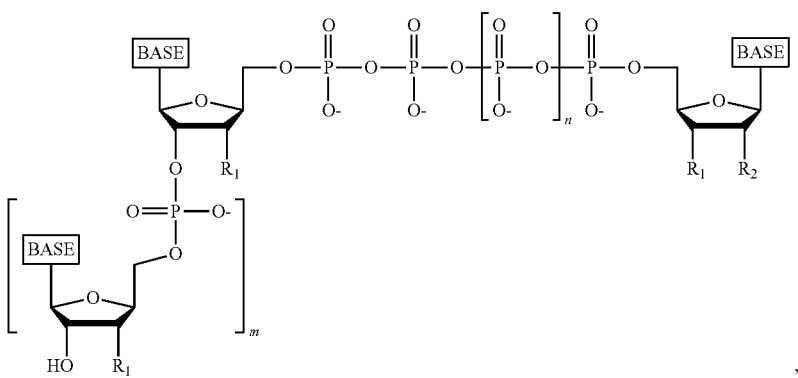

wherein m an integer from 0 to 100, and wherein the compound comprises a single type of base, and wherein the base is adenine, guanine, cytosine, uracil or thymine or a derivative thereof of each.

A compound having the structure:

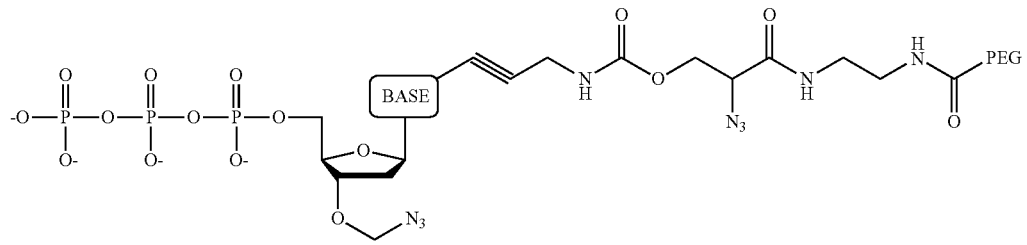

wherein the base is adenine, guanine, cytosine, thymine, uracil, a 7-deazapurine or a 5-methylpyrimidine.

A compound having the structure:

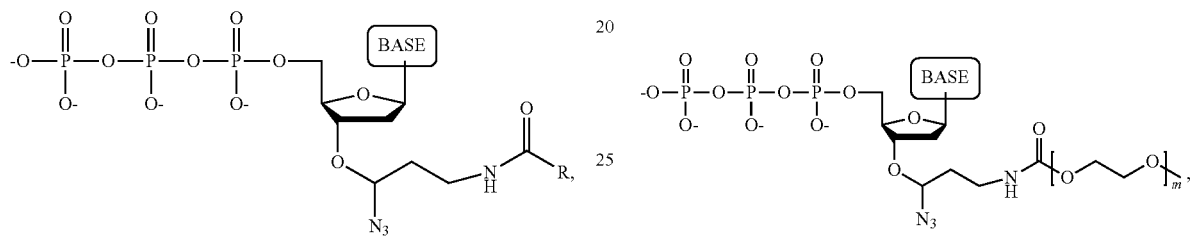

wherein the base is adenine, guanine, cytosine, thymine, uracil, a 7-deazapurine or a 5-methylpyrimidine, and R is a substituted or unsubstituted hydrocarbyl, up to 3000 daltons.

A compound having the structure:

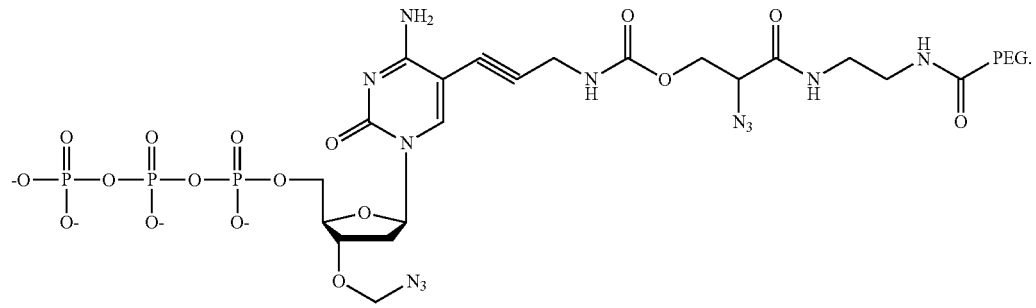

A compound having the structure:

wherein the base is adenine, guanine, cytosine, thymine, uracil, a 7-deazapurine or a 5-methylpyrimidine, and m is an integer from 1-50.

A compound having the structure:

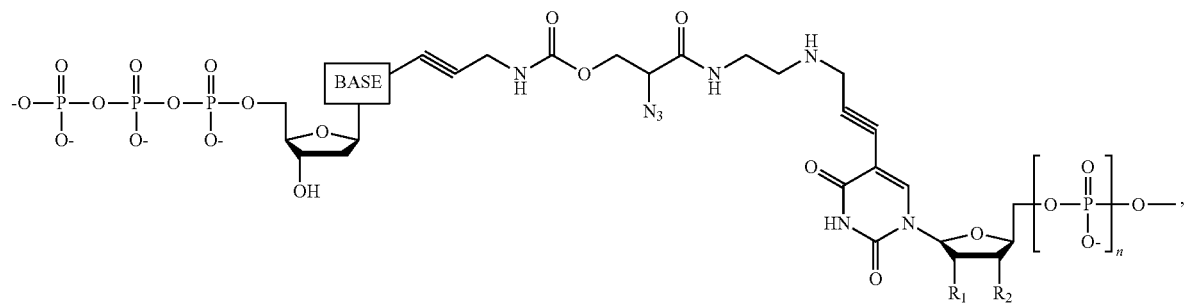

wherein n is 1 or 2 and the base is adenine, guanine, cytosine, thymine, uracil, a 7-deazapurine or a 5-methylpyrimidine.

A compound having the structure:

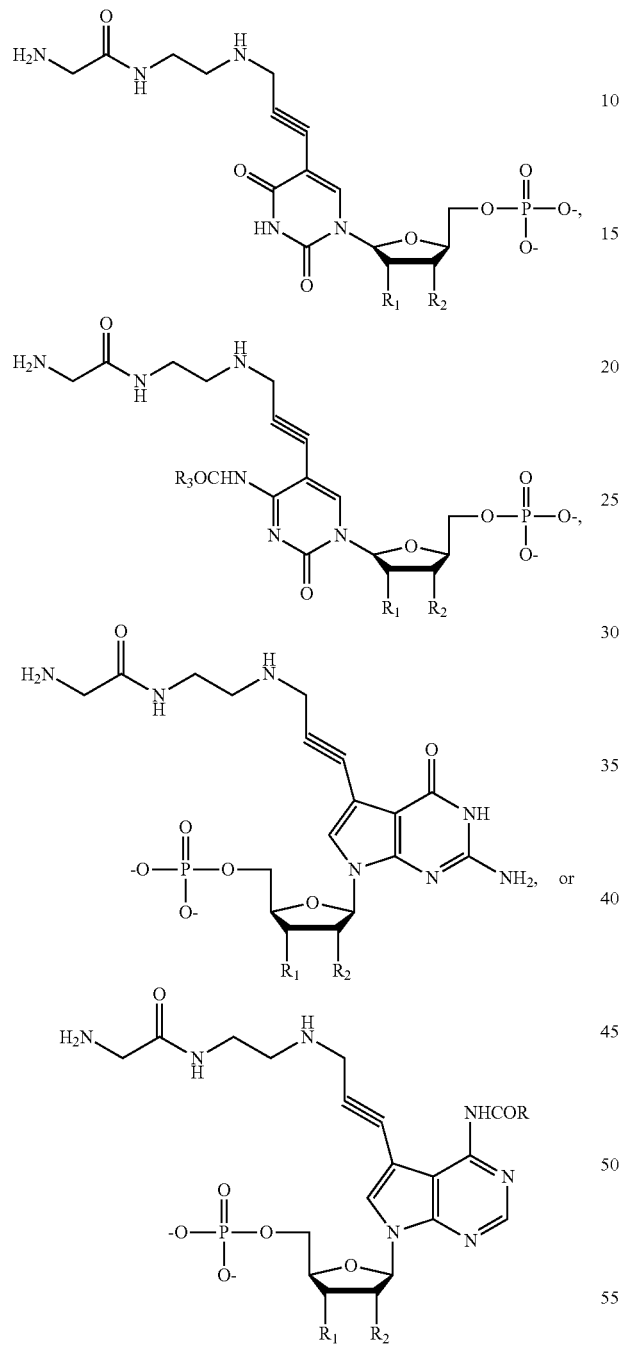

wherein $R_1$ is —OH, or —O—$CH_2N_3$, and $R_2$ is H or OH.

A method for determining the nucleotide sequence of a single-stranded RNA comprising:
(a) contacting the single-stranded RNA, wherein the single-stranded RNA is in an electrolyte solution in contact with a nanopore in a membrane, wherein the single-stranded RNA has a primer hybridized to a portion thereof, with a RNA polymerase and at least four ribonucleotide polyphosphate (rNPP) analogues under conditions permitting the RNA polymerase to catalyze incorporation of one of the rNPP analogues into the primer if it is complementary to the nucleotide residue of the single-stranded RNA which is immediately 5' to a nucleotide residue of the single-stranded RNA hybridized to the 3' terminal nucleotide residue of the primer, so as to form a RNA extension product, wherein each of the four rNPP analogues has the structure:

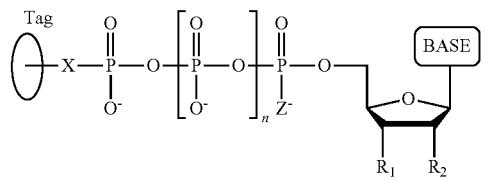

wherein the base is adenine, guanine, cytosine, thymine or uracil, or a derivative thereof of each, wherein $R_1$ is OH, wherein $R_2$ is OH, wherein X is O, NH, S or $CH_2$, wherein n is 1, 2, 3, or 4, wherein Z is O, S, or $BH_3$, and with the proviso that (i) the type of base on each rNPP analogue is different from the type of base on each of the other three rNPP analogues, and (ii) either the value of n of each rNPP analogue is different from the value of n of each of the other three rNPP analogues, or the value of n of each of the four rNPP analogues is the same and the type of tag on each rNPP analogue is different from the type of tag on each of the other three rNPP analogues, wherein incorporation of the rNPP analogue results in release of a polyphosphate having the tag attached thereto; and (b) determining which rNPP analogue has been incorporated into the primer to form a RNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, as appropriate, thereby identifying the nucleotide residue in the single-stranded RNA complementary to the incorporated rNPP analogue; and (c) iteratively performing steps (a) and (b) for each nucleotide residue of the single-stranded RNA being sequenced, wherein in each iteration of step (a) the rNPP analogue is incorporated into the RNA extension product resulting from the previous iteration of step (a) if it is complementary to the nucleotide residue of the single-stranded RNA which is immediately 5' to a nucleotide residue of the single-stranded RNA hybridized to the 3' terminal nucleotide residue of the RNA extension product, thereby determining the nucleotide sequence of the single-stranded RNA.

A method for determining the nucleotide sequence of a single-stranded RNA comprising:
(a) contacting the single-stranded RNA, wherein the single-stranded RNA is in an electrolyte solution in contact with a nanopore in a membrane and wherein the single-stranded RNA has a primer hybridized to a portion thereof, a RNA polymerase and a ribonucleotide polyphosphate (rNPP) analogue under conditions permitting the RNA polymerase to catalyze incorporation of the rNPP analogue into the primer if it is complementary to the nucleotide residue of the single-stranded RNA which is immediately 5' to a nucleotide residue of the single-stranded RNA hybridized to the 3' terminal nucleotide residue of the primer, so as to form a RNA extension product, wherein the rNPP analogue has the structure:

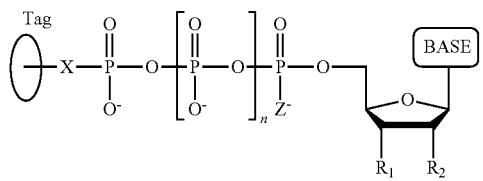

wherein the base is adenine, guanine, cytosine, uracil or thymine, wherein $R_1$ is —OH, —O—CH$_2$N$_3$ or —O-2-nitrobenzyl, wherein $R_2$ is —OH, wherein X is O, NH, S or CH$_2$, wherein n is 1, 2, 3, or 4, wherein Z is O, S, or BH$_3$, and wherein if the rNPP analogue is not incorporated, iteratively repeating the contacting with a different rNPP analogue until a rNPP analogue is incorporated, with the proviso that (1) the type of base on each rNPP analogue is different from the type of base on each of the other rNPP analogues, and (2) either the value of n of each rNPP analogue is different from the value of n of each of the other three rNPP analogues, or the value of n of each of the four rNPP analogues is the same and the type of tag on each rNPP analogue is different from the type of tag on each of the other three rNPP analogues, wherein incorporation of a rNPP analogue results in release of a polyphosphate having the tag attached thereto;

(b) determining which rNPP analogue has been incorporated into the primer to form a RNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or different for each type of tag, as appropriate, thereby identifying the nucleotide residue in the single-stranded RNA complementary to the incorporated dNPP analogue;

(c) iteratively performing steps (a) and (b) for each nucleotide residue of the single-stranded RNA being sequenced, wherein in each iteration of step (a) the rNPP analogue is incorporated into the RNA extension product resulting from the previous iteration of step (a) if it is complementary to the nucleotide residue of the single-stranded RNA which is immediately 5' to a nucleotide residue of the single-stranded RNA hybridized to the 3' terminal nucleotide residue of the RNA extension product, thereby determining the nucleotide sequence of the single-stranded RNA.

$R_1$ and $R_2$=H, OH, F, NH$_2$, N$_3$, or OR';

n=1-5;

A=O, S, CH$_2$, CHF, CFF, NH;

Z=O, S, BH$_3$;

X=Linker which links phosphate or the 2'-O or 3'-O or the base to the detectable moiety and may contain O, N or S, P atoms. (The linker can also be a detectable moiety, directly or indirectly, such as amino acids, peptides, proteins, carbohydrates, PEGs of different length and molecular weights, organic or inorganic dyes, fluorescent and fluorogenic dyes, drugs, oligonucleotides, mass tags, chemiluminescent tags and may contain positive or negative charges.);

Y=tags or detectable moiety, such as aliphatic or organic aromatic compounds with one or more rings, dyes, proteins, carbohydrates, PEGs of different length and molecular weights, drugs, oligonucleotides, mass tags, fluorescent tags, chemiluminescent tags and may contain positive or negative charge.

Figure 16:
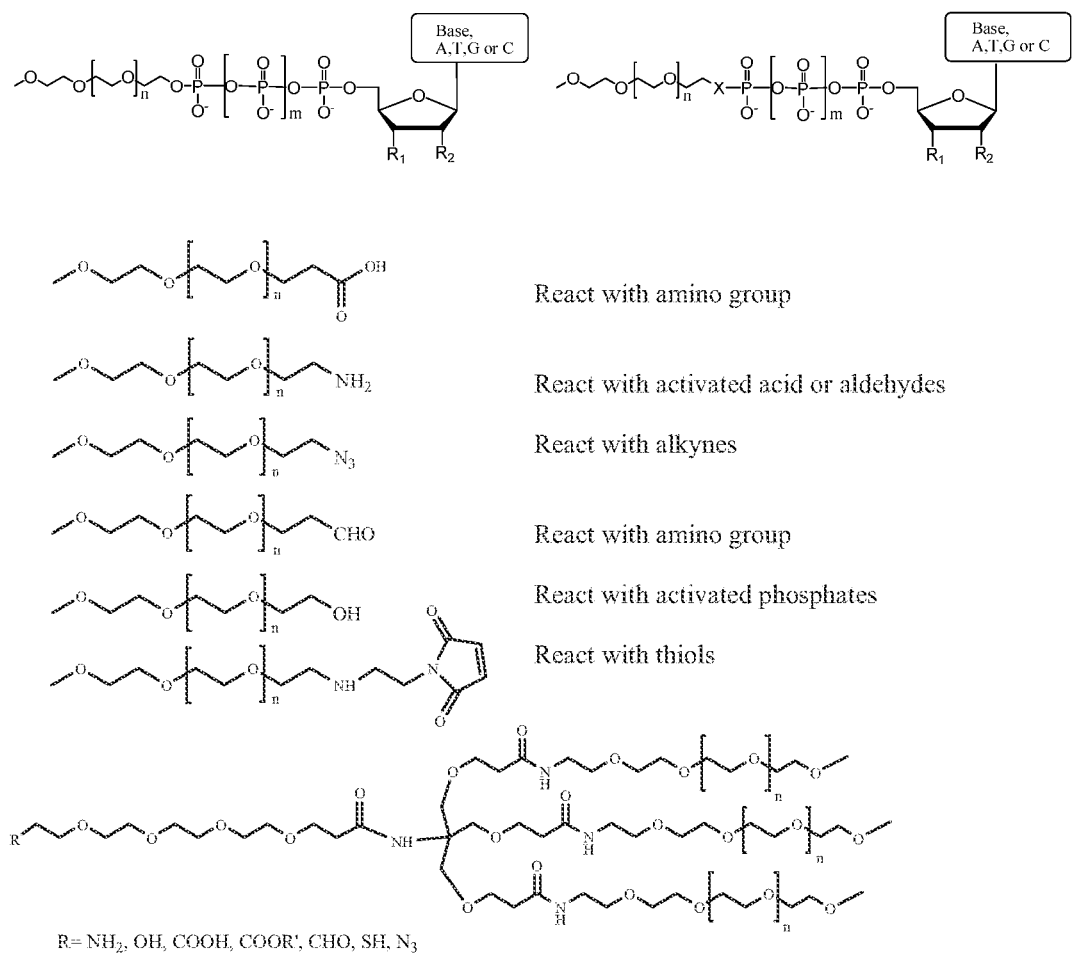

FIG. 16. Structures of PEG-phosphate-labeled nucleotides and examples of possible PEGs with different reactive groups to react with functional groups.

Figure 17:
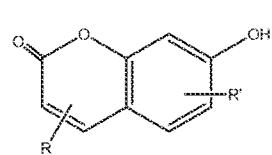
Figure 17:
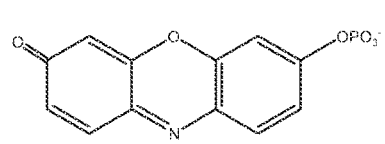
Figure 17:
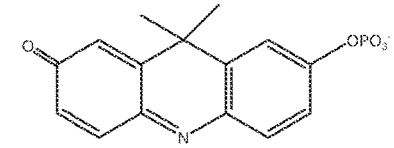
Figure 17:
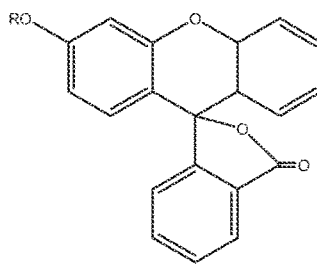
Figure 17:
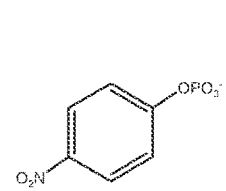
Figure 17:
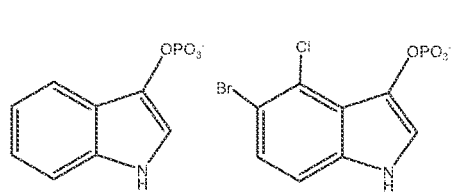

FIG. 17. Non-limiting, specific examples of reactive groups on the terminal phosphates, which can also be attached with appropriate changes to a nucleoside base moiety, and groups with which groups can react to form tags.

Figure 18:
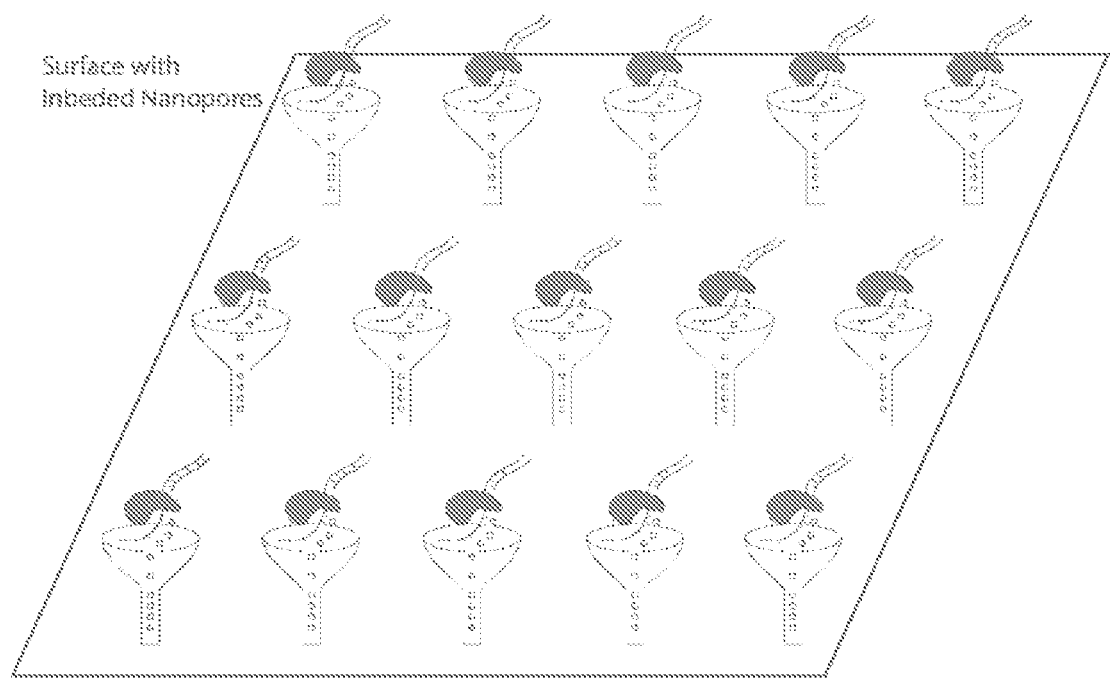

FIG. 18. A schematic of array of nanopores for massive parallel DNA sequencing by synthesis.

Figure 19:
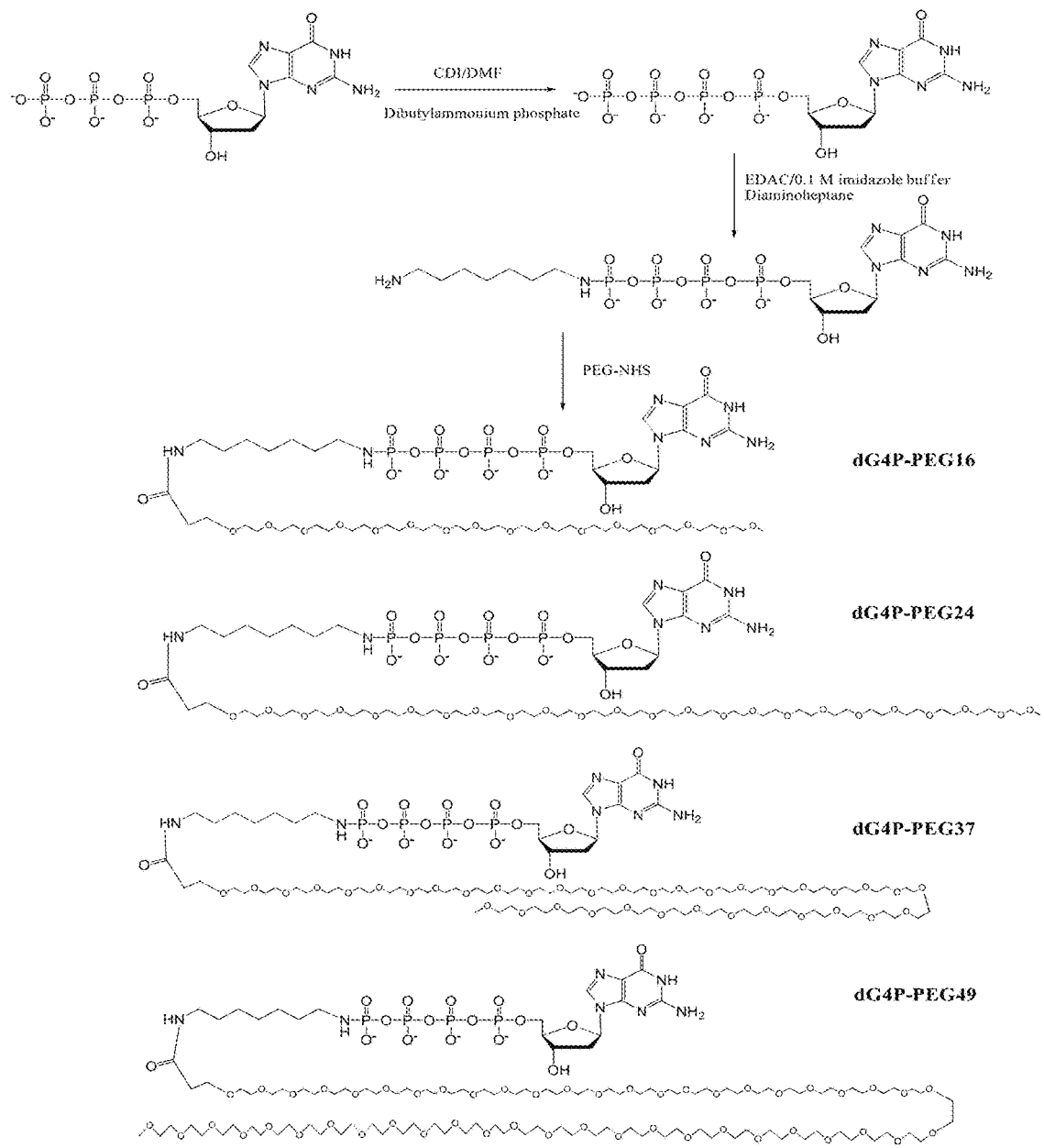
Figure 19:
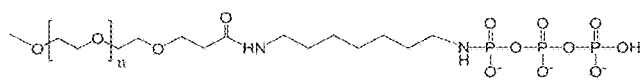

FIG. 19. Synthesis of PEG-phosphate-labeled nucleotides.

Figure 20:
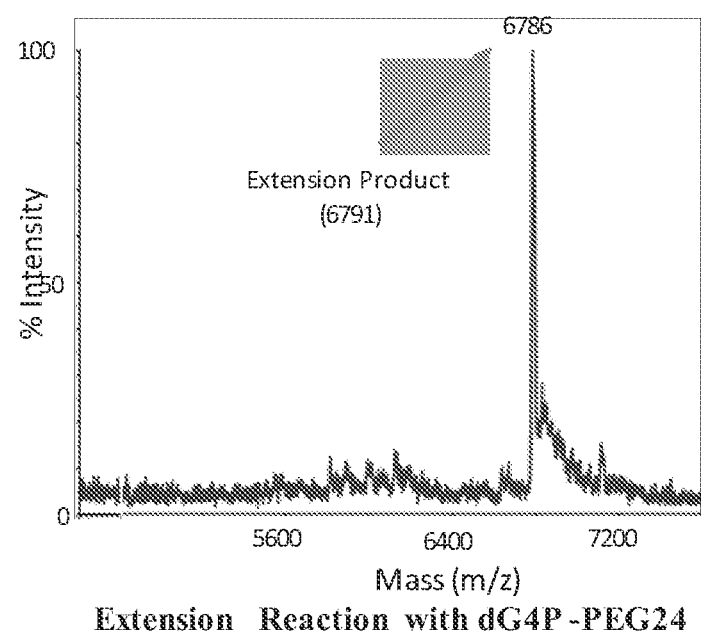
Figure 20:
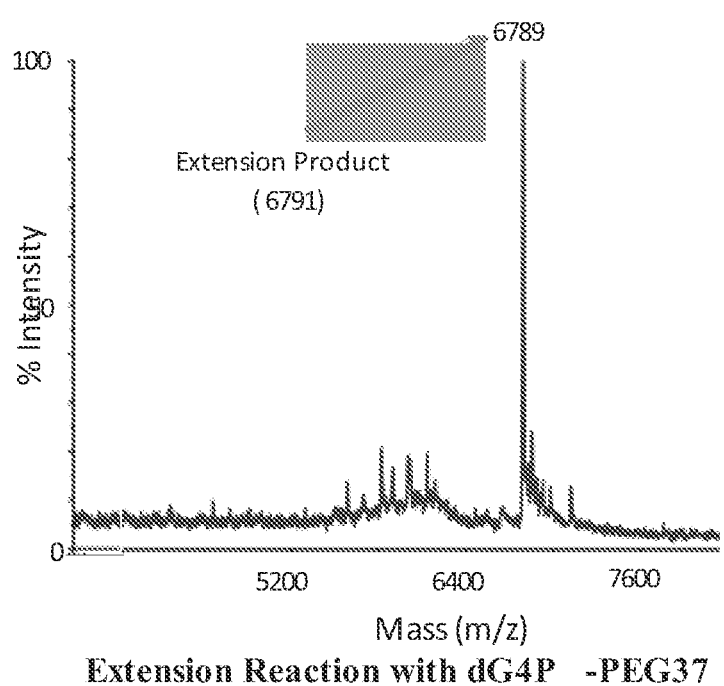

FIG. 20. MALDI-TOF mass spectra of the DNA extension products generated by incorporation of PEG-phosphate-labeled nucleotide analogues (dG4P-PEG). The single products shown in the spectra indicate that the dG4P-PEG24 and dG4P-PEG37 are incorporated at nearly 100% efficiency.

Figure 21:
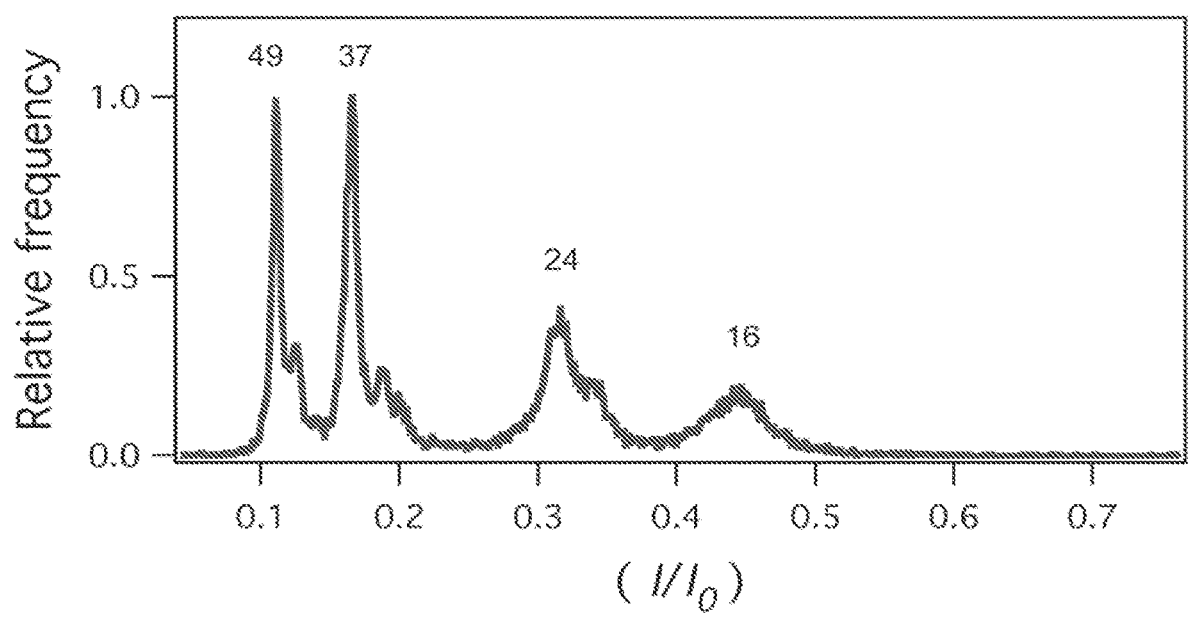

FIG. 21. The relative blockade depth distributions for α-hemolysin nanopore in the presence of PEGs that contain either 49, 37, 24, or 16 ethylene oxide monomers at +40 mV applied potential. The four species are easily identified.

Figure 22:
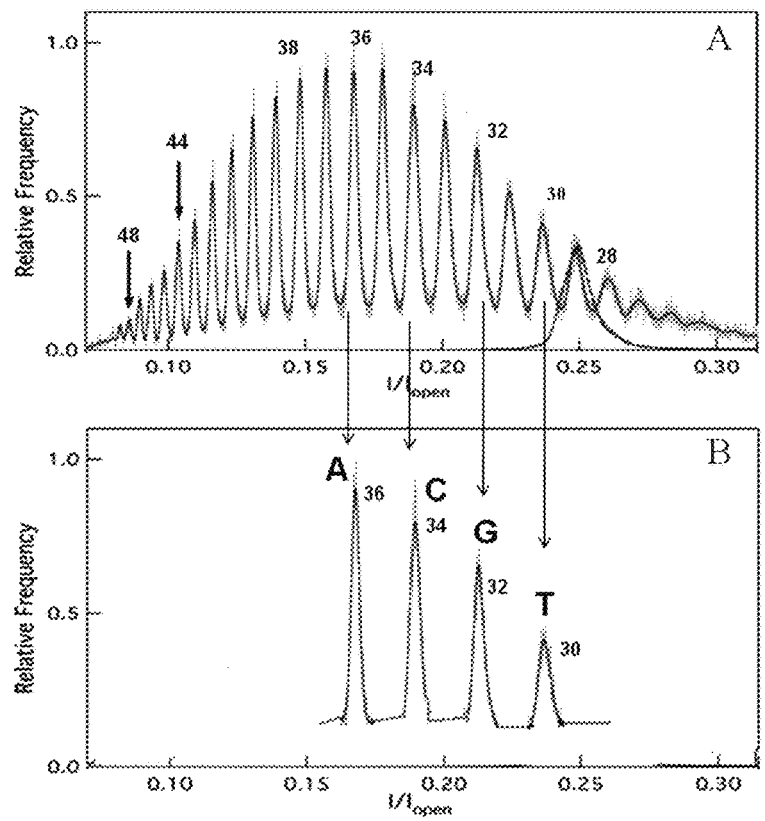
Figure 22:
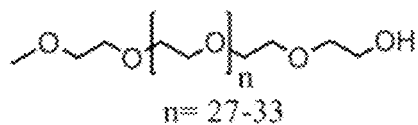
Figure 22:
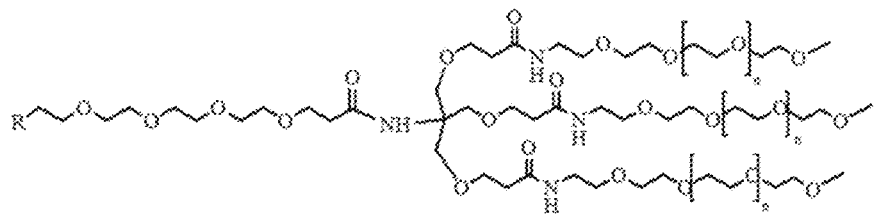

FIG. 22. (A) Separation and mass distribution of mixed poly (ethylene glycol) (PEG) units through a single nanopore; and (B) selection of 4 distinct PEG units with base line separation as tags for the 4 bases, A, C, G, and T. The structures of linear and branched PEGs are also shown.

Figure 23:
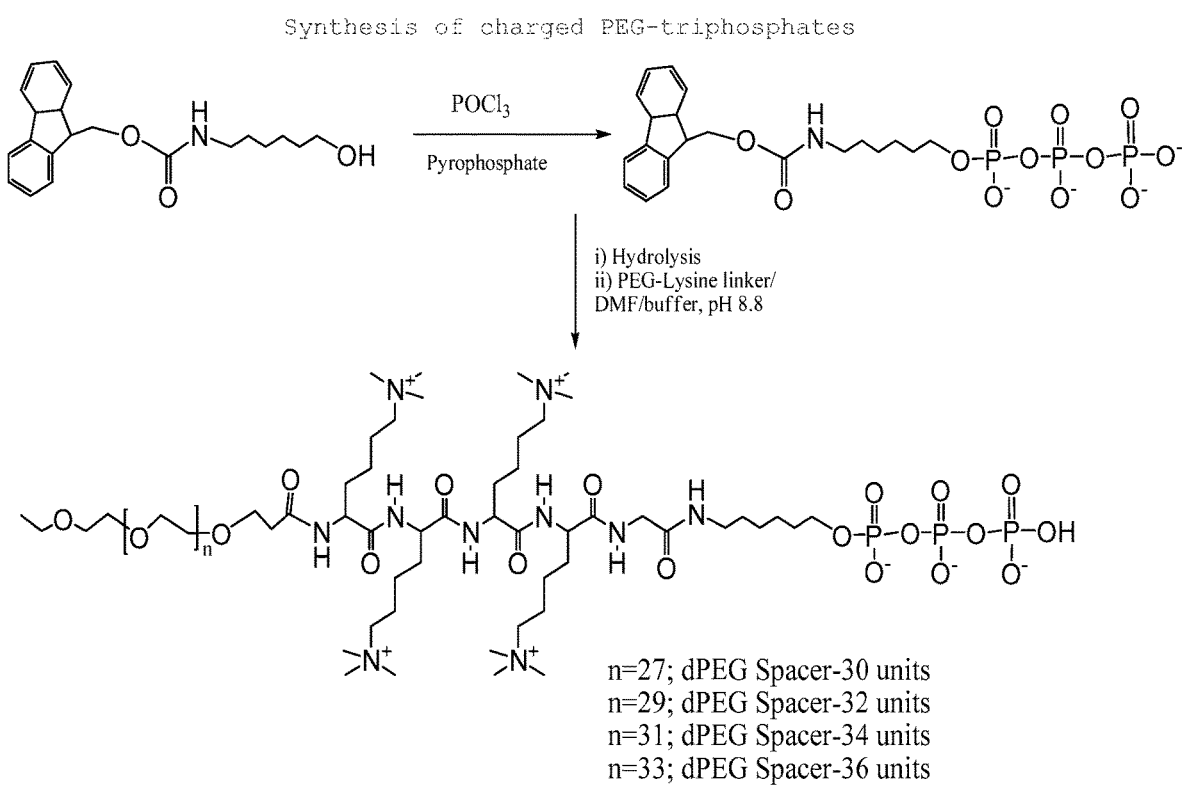

FIG. 23. Synthesis of charged PEG-triphosphates (the charge can be adjusted based on the requirements).

Figure 24:
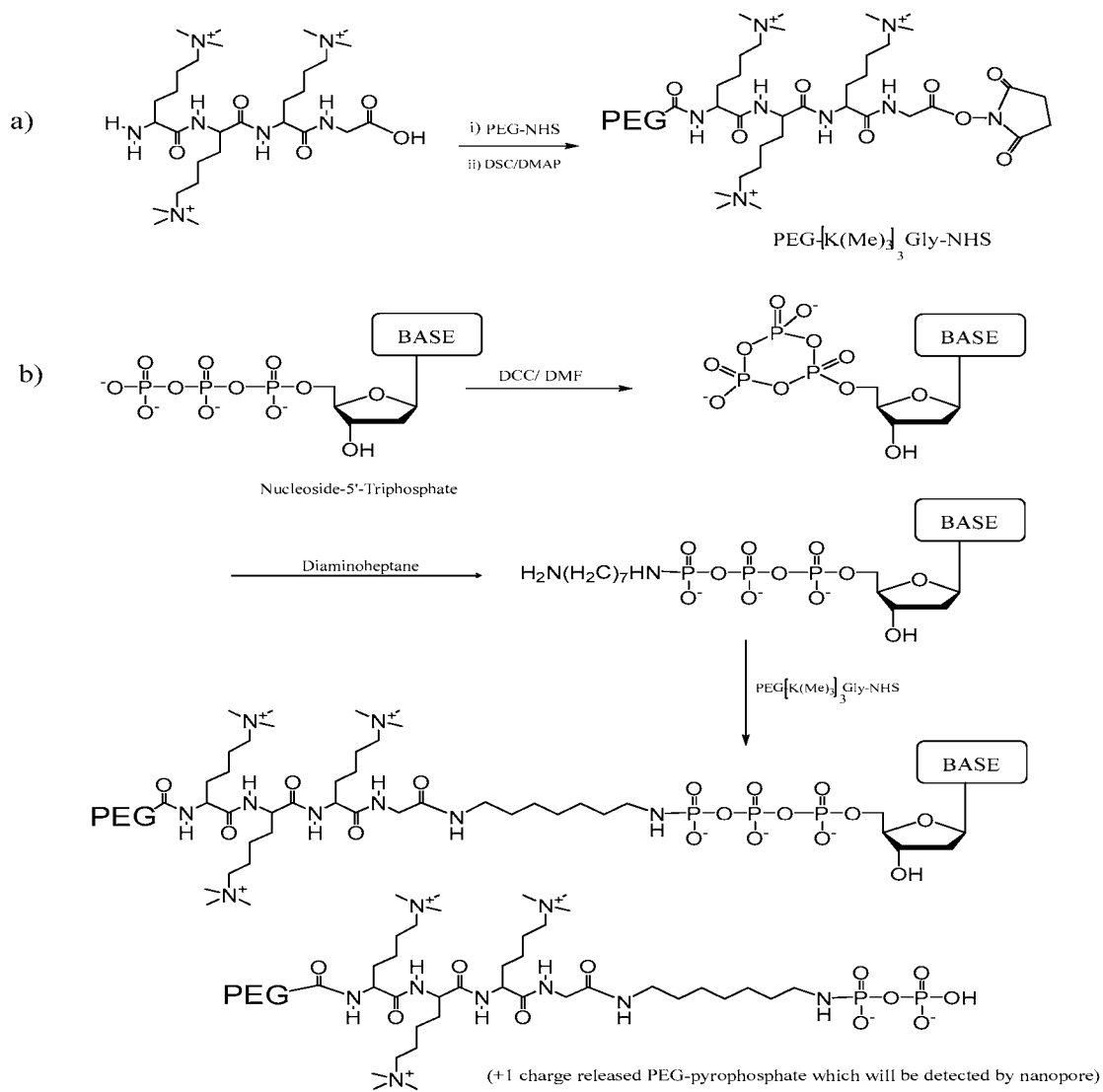

FIG. 24. Synthesis of phosphate-tagged nucleoside-5'-triphosphates.

Figure 25:
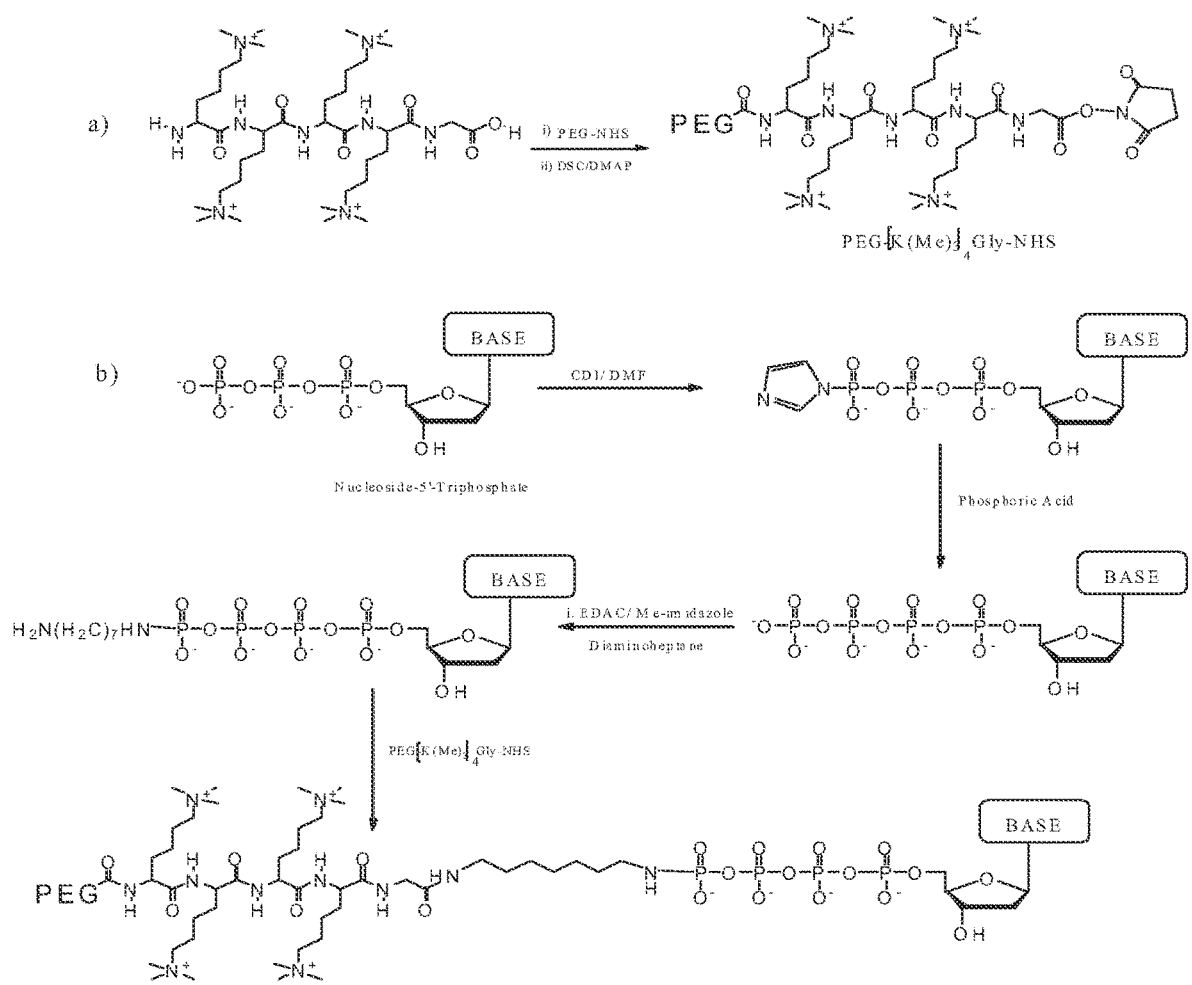

FIG. 25. Synthesis of phosphate-tagged nucleoside-5'-tetraphosphates

Figure 26:
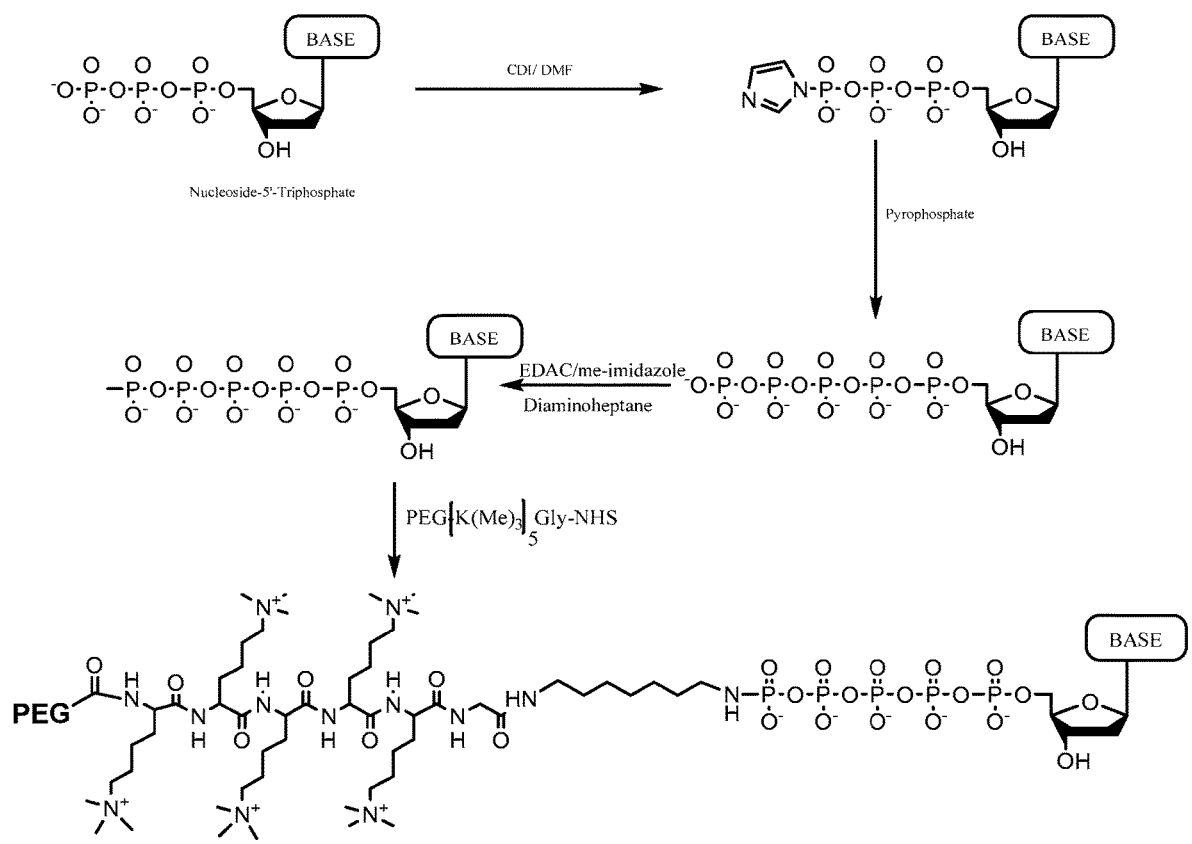

FIG. 26. Synthesis of terminal phosphate-tagged nucleoside-5'-pentaphosphates.

Figure 27:
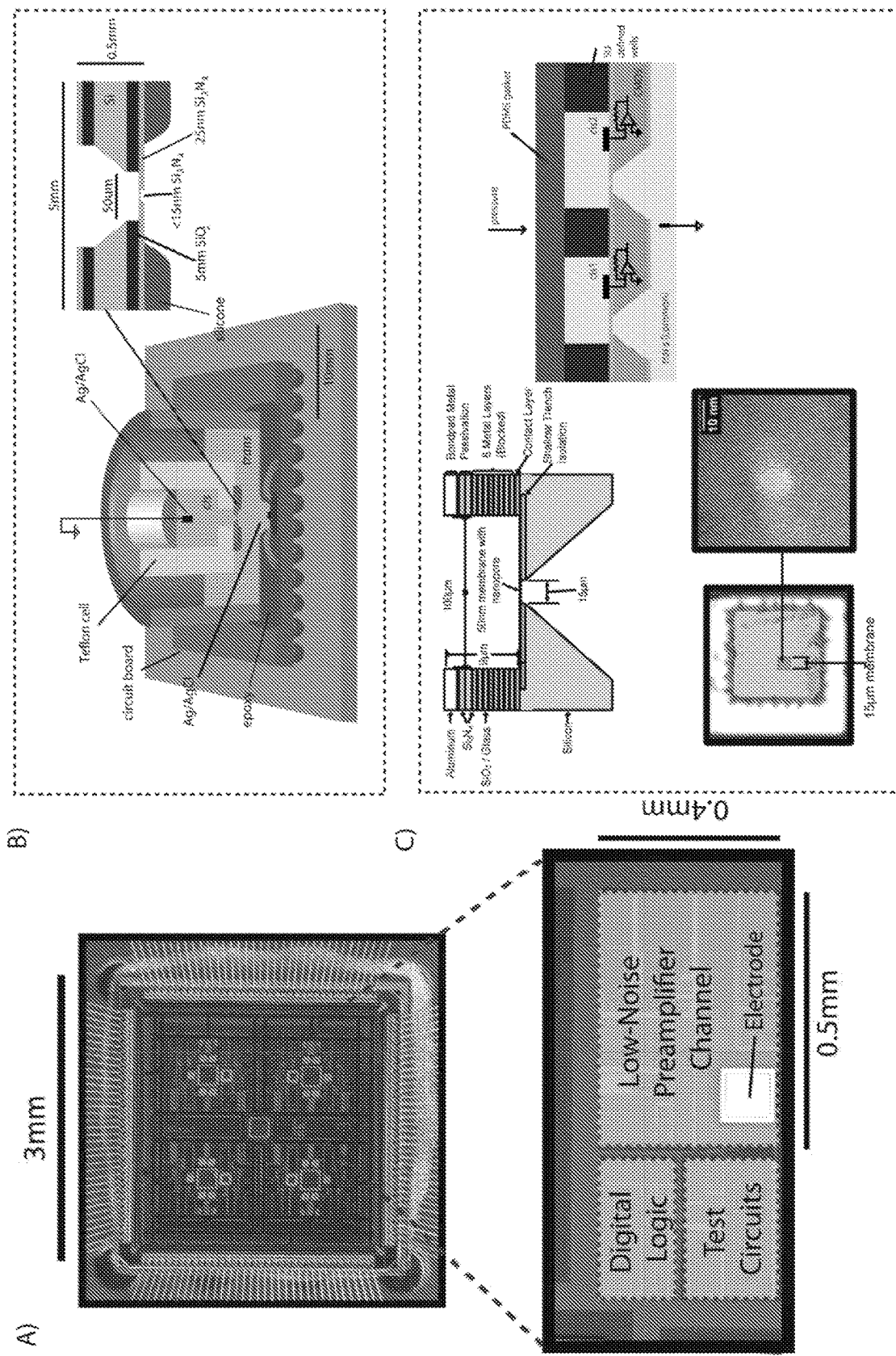

FIG. 27. CMOS-integrated nanopore measurement platform: (A) a micrograph of the eight-channel CMOS preamplifier chip with an image of one amplifier channel with the integrated cis-side electrode; (B) diagram showing the two-chip integration with a solid-state nanopore; (C) diagram showing the cross section of the chip and how the nanopore is etched directly into the chip in the one-chip implementation; packaging occurs with an independent well on the cis side; and a TEM image of a 3.5-nm-diameter nanopore.

Figure 28:
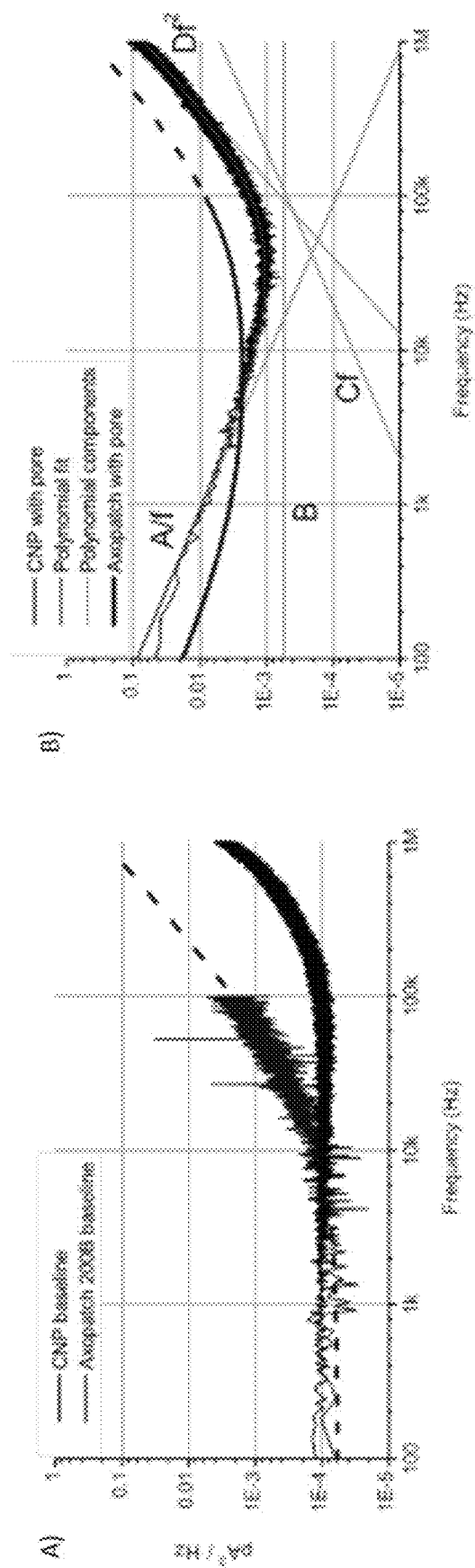

FIG. 28. Electrical performance of the CMOS-integrated nanopore electronics (A) Input-referred baseline current noise spectrum for $C_F$=0.15 pF, 1 MHz 4-pole Bessel filter, $f_s$=4MS/s. Also shown is the measured open-headstage of an Axopatch 200B in whole-cell mode with β=1, 100 kHz 4-pole Bessel filter, $f_s$=250 kS/s. (B) Noise floor of the new amplifier with a nanopore attached compared with the same nanopore measured by the Axopatch 200B.

Figure 29:
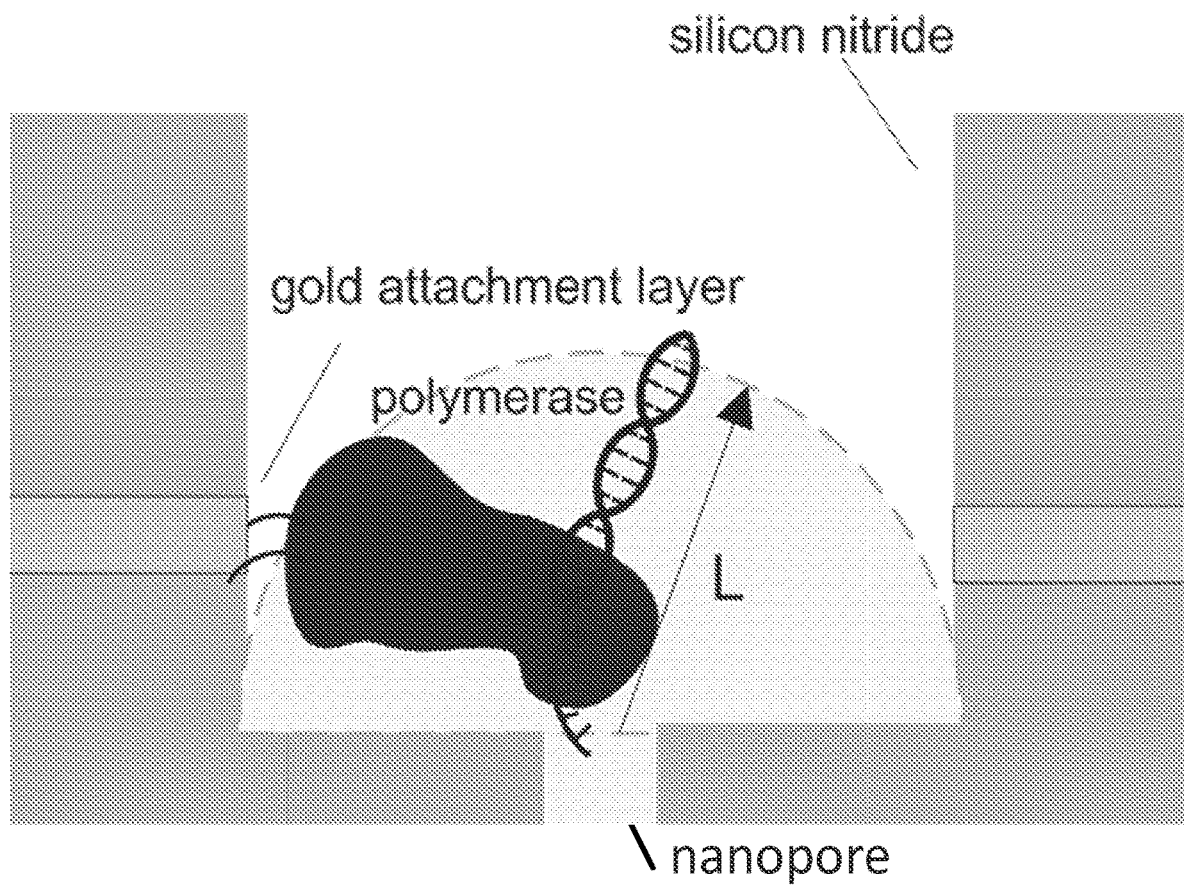

FIG. 29. Tethering of the polymerase in the vicinity of the nanopore. A well helps to restrict diffusion. L denotes the critical distance from the pore opening at which molecular motions due to diffusion and electrophoresis are equal.

Figure 30:
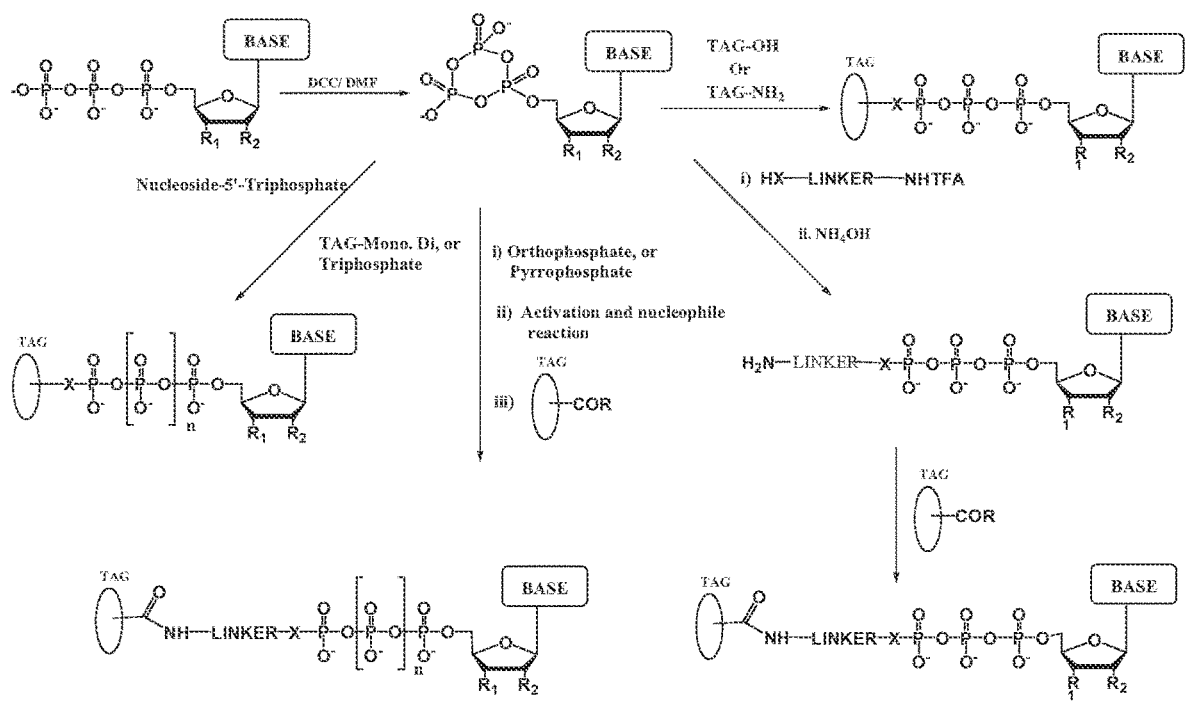

FIG. 30. Synthesis of Tag-labeled-nucleoside-5'-polyphosphates.

Figure 31:
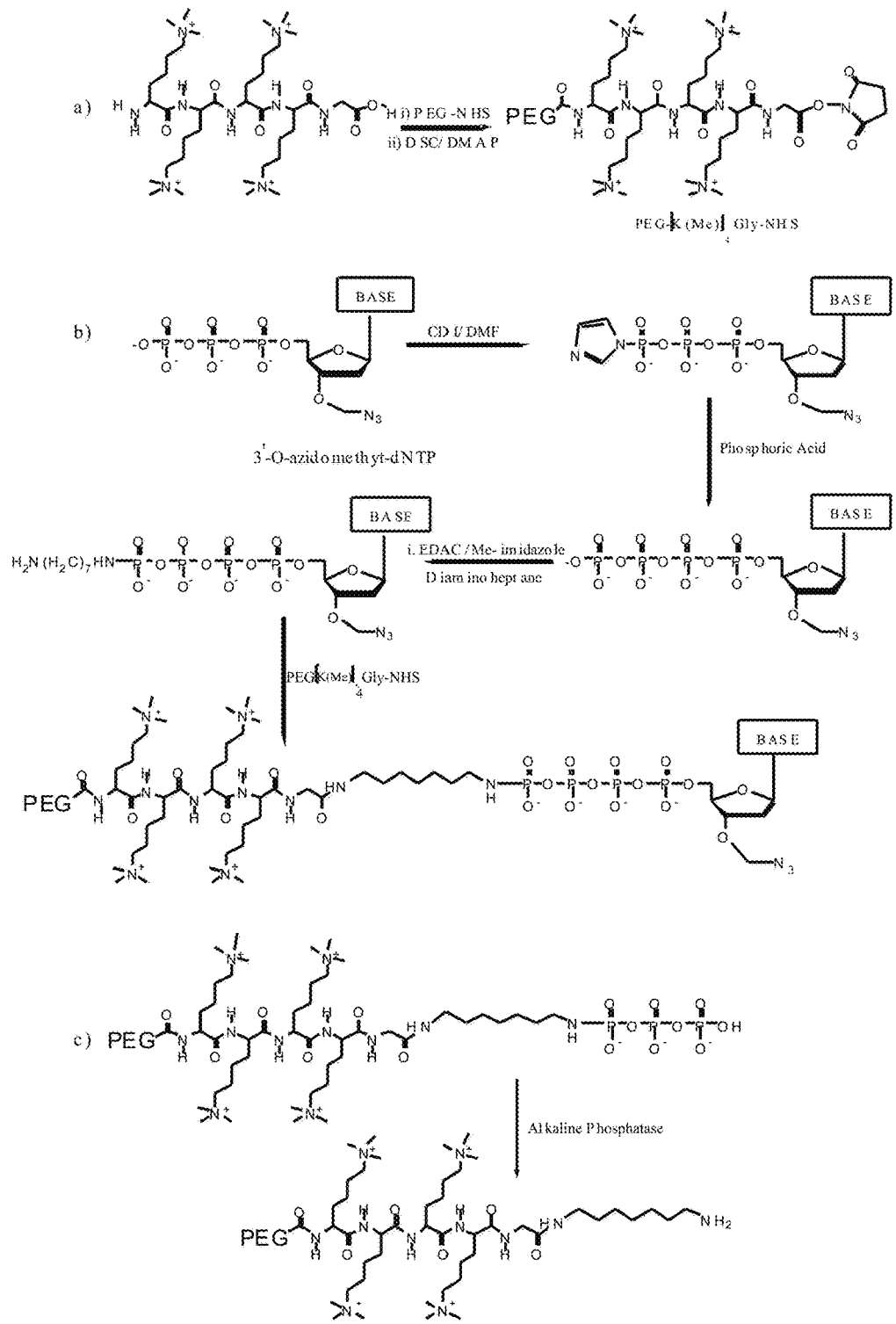

FIG. 31. Synthesis of 3'-O-blocked-PEG-nucleotides.

Figure 32:
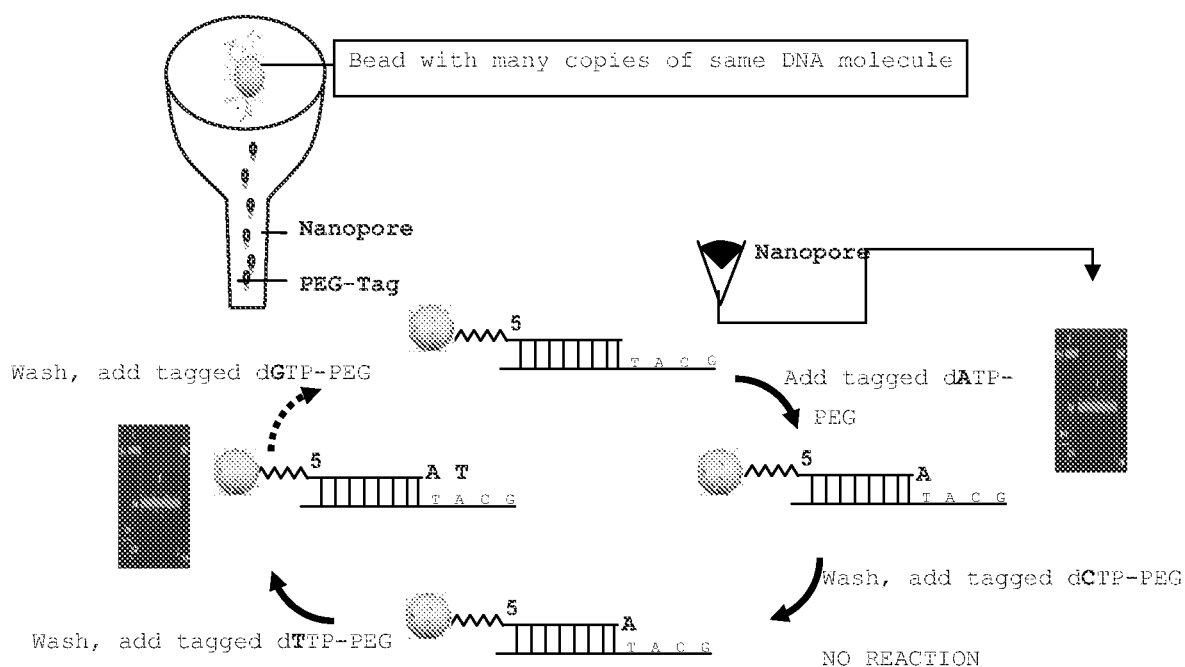

FIG. 32. Sequencing by synthesis with PEG-nucleotides and nanopore detection (many copies of the same DNA molecule immobilized on a bead and addition of one PEG-nucleotide at a time). Use same PEGattached to the all four nucleotides. Add one PEG-nucleotide at a time, reads at least one base per cycle if correct nucleotide is incorporated.

Figure 33:
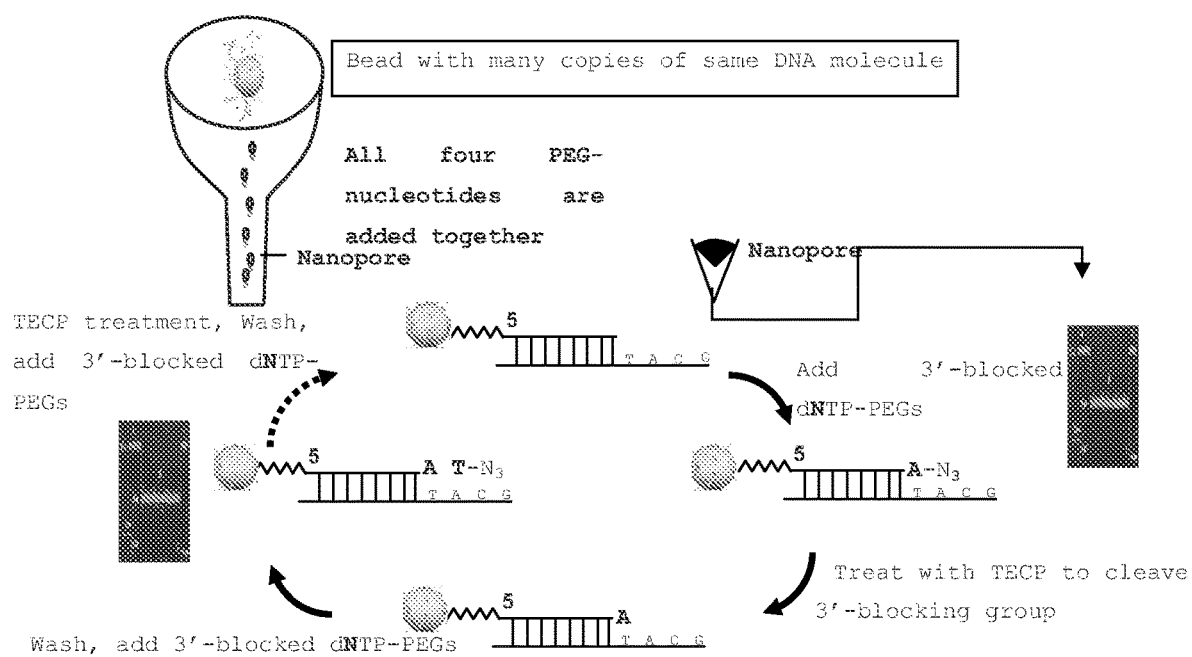

FIG. 33. Sequencing by synthesis with 3'-O-blocked-PEG-nucleotides and nanopore detection (many copies of same DNA molecule immobilized on a bead and addition of all four 3'-O-blocked-PEG-nucleotides). Add all four 3'-blocked, different size PEG attached nucleotides (3'=blocked dNTP-PEGs) together. Detection of the incorporated nucleotide based on the blockade signal of the released PEGs. The 3'-blocking group is removed by TECP treatment and continue cycle for correctly sequence the template including homopolymeric regions.

Figure 34:
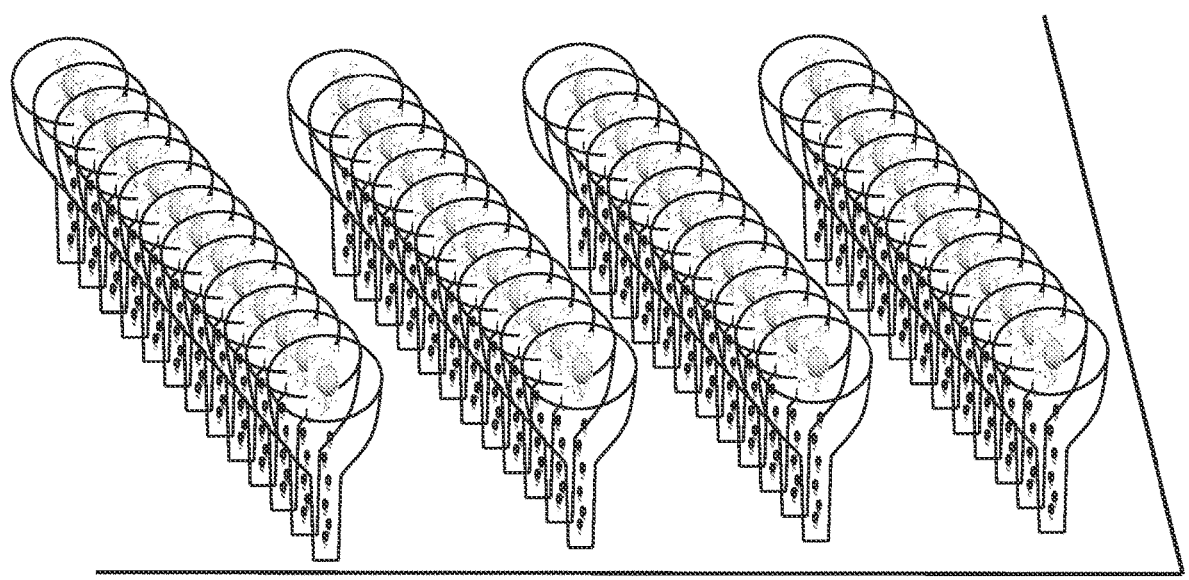

FIG. 34. A schematic for a massive parallel way high density array of micro wells to perform the biochemical process. Each well can hold a different DNA template and nanopore device.

DETAILED DESCRIPTION OF THE INVENTION

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and at least four deoxyribonucleotide polyphosphate (dNPP) analogues under conditions permitting the DNA polymerase to catalyze incorporation of one of the dNPP analogues into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein each of the four dNPP analogues has the structure:

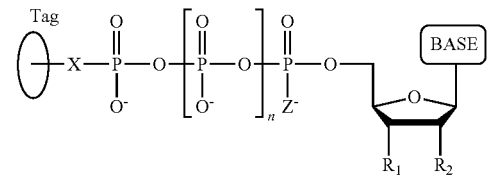

wherein the base is adenine, guanine, cytosine, thymine or uracil, or a derivative of each thereof, wherein $R_1$ is OH, wherein $R_2$ is H, wherein X is O, NH, S or $CH_2$, wherein n is 1, 2, 3, or 4, wherein Z is O, S, or $BH_3$, and with the proviso that (i) the type of base on each dNPP analogue is different from the type of base on each of the other three dNPP analogues, and (ii) either the value of n of each dNPP analogue is different from the value of n of each of the other three dNPP analogues, or the value of n of each of the four dNPP analogues is the same and the type of tag on each dNPP analogue is different from the type of tag on each of the other three dNPP analogues, wherein incorporation of the dNPP analogue results in release of a polyphosphate having the tag attached thereto; and (b) determining which dNPP analogue has been incorporated into the primer to form a DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, as appropriate, thereby identifying the nucleotide residue in the single-stranded DNA complementary to the incorporated dNPP analogue; and (c) iteratively performing steps (a) and (b) for each nucleotide residue of the single-stranded DNA being sequenced, wherein in each iteration of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, a DNA polymerase and a deoxyribonucleotide polyphosphate (dNPP) analogue under conditions permitting the DNA polymerase to catalyze incorporation of the dNPP analogue into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the dNPP analogue has the structure:

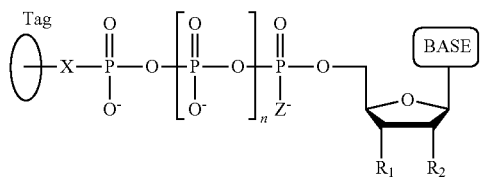

wherein the base is adenine, guanine, cytosine, uracil or thymine, or a derivative of each thereof, wherein $R_1$ is —OH, —O—$CH_2N_3$ or —O-2-nitrobenzyl, wherein $R_2$ is H, wherein X is O, NH, S or $CH_2$, wherein n is 1, 2, 3, or 4, wherein Z is O, S, or $BH_3$, and wherein if the dNPP analogue is not incorporated, iteratively repeating the contacting with a different dNPP analogue until a dNPP analogue is incorporated, with the proviso that (1) the type of base on each dNPP analogue is different from the type of base on each of the other dNPP analogues, and (2) either the value of n of each dNPP analogue is different from the value of n of each of the other three dNPP analogues, or the value of n of each of the four dNPP analogues is the same and the type of tag on each dNPP analogue is different from the type of tag on each of the other three dNPP analogues, wherein incorporation of a dNPP analogue results in release of a polyphosphate having the tag attached thereto;

(b) determining which dNPP analogue has been incorporated into the primer to form a DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, as appropriate, thereby identifying the nucleotide residue in the single-stranded DNA complementary to the incorporated dNPP analogue;

(c) iteratively performing steps (a) and (b) for each nucleotide residue of the single-stranded DNA being sequenced, wherein in each iteration of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and at least four deoxyribonucleotide polyphosphate (dNPP) analogues under conditions permitting the DNA polymerase to catalyze incorporation of one of the dNPP analogues into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein each of the four dNPP analogues has a structure chosen from the following:

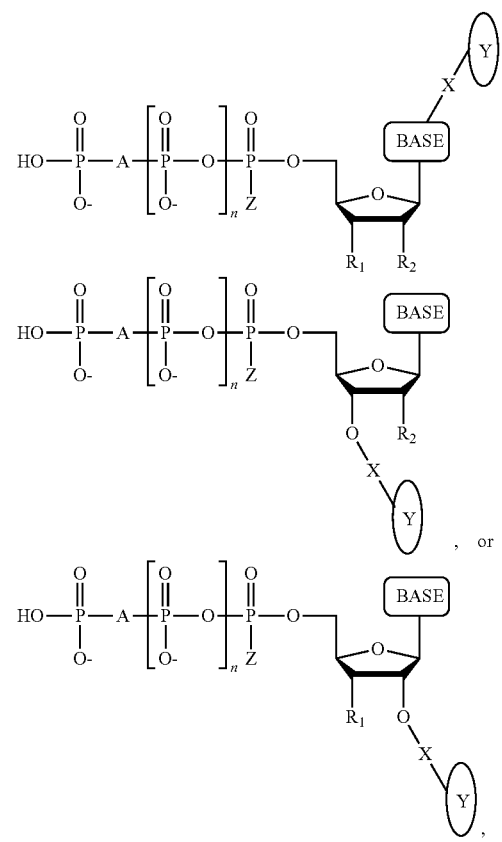

wherein the base is adenine, guanine, cytosine, uracil or thymine, or a derivative of each thereof, wherein Y is a tag, wherein $R_1$, if present, is OH, wherein $R_2$, if present, is H, wherein X is a cleavable linker, wherein Z is O, S or $BH_3$, wherein n is 1, 2, 3, or 4, wherein A is O, S, $CH_2$, CHF, CFF, or NH, and with the proviso that (i) the type of base on each dNPP analogue is different from the type of base on each of the other three dNPP analogues, and (ii) the type of tag on each dNPP analogue is different from the type of tag on each of the other three dNPP analogues;

(b) cleaving the tag from the dNPP analogue incorporated in step (a); and (c) determining which dNPP analogue was incorporated in step (a) by applying a voltage across the membrane and measuring an electronic change across the nanopore resulting from tag cleaved off in step (b) translocating through the nanopore, wherein the electronic change is different for each different type of tag, thereby identifying the nucleotide residue in the single-stranded DNA complementary to the incorporated dNPP analogue; and (d) iteratively performing steps (a), (b) and (c) for each nucleotide residue of the single-stranded DNA being sequenced, wherein in each iteration of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane, wherein the single-stranded DNA has a primer hybridized to a portion thereof, a DNA polymerase and a deoxyribonucleotide polyphosphate (dNPP) analogue under conditions permitting the DNA polymerase to catalyze incorporation of the dNPP analogue into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the dNPP analogue has the structure:

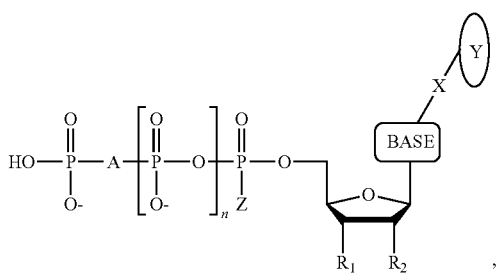

-continued

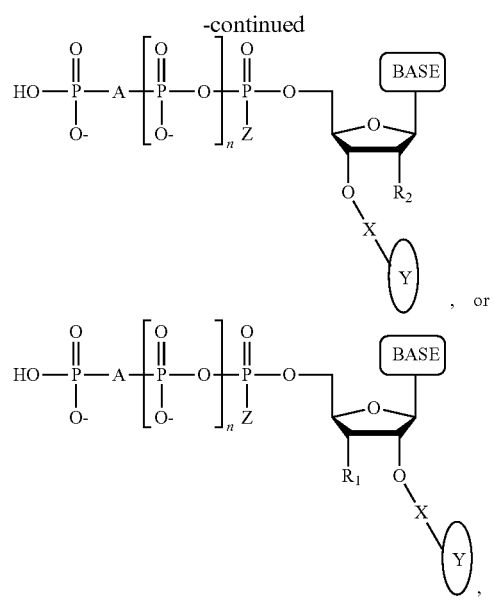

wherein the base is adenine, guanine, cytosine, uracil or thymine, or derivative of each thereof, wherein Y is a tag, and wherein $R_1$ if present is OH, —$OCH_2N_3$ or —O-2-nitrobenzyl, $R_2$ if present is H, wherein X is a cleavable linker, wherein Z is O, S or $BH_3$, wherein n is 1, 2, 3, or 4, wherein A is O, S, $CH_2$, CHF, CFF, or NH, and if the dNPP analogue is not incorporated, iteratively repeating the contacting with a different dNPP analogue until a dNPP analogue is incorporated, with the proviso that (1) the type of base on each dNPP analogue is different from the type of base on each other dNPP analogue, and (2) the type of tag on each dNPP analogue is different from the type of tag on each other dNPP analogue, wherein incorporation of a dNPP analogue results in release of a polyphosphate having the tag attached thereto;

(b) cleaving the tag from the dNPP analogue incorporated in step (a); and (c) determining which dNPP analogue was incorporated in step (a) to form a DNA extension product by applying a voltage across the membrane and measuring an electronic change across the nanopore resulting from the tag cleaved off in step (b) translocating through the nanopore, wherein the electronic change is different for each type of tag, thereby identifying the nucleotide residue in the single-stranded DNA complementary to the incorporated dNPP analogue;

(d) iteratively performing steps (a) through (c) for each nucleotide residue of the single-stranded DNA being sequenced, wherein in each iteration of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

In an embodiment of the methods the tag is ethylene glycol, an amino acid, a carbohydrate, a dye, a mononucleotide, a dinucleotide, a trinucleotide, a tetranucleotide, a pentanucleotide or a hexanucleotide, a fluorescent dyes, a chemiluminescent compound, an amino acid, a peptide, a carbohydrate, a nucleotide monophosphate, a nucleotide diphosphate, an aliphatic acid or an aromatic acid or an alcohol or a thiol with unsubstituted or substituted with one or more halogens, a cyano group, a nitro group, an alkyl group, an alkenyl group, an alkynyl group, an azido group.

In an embodiment of the methods the base is selected from the group consisting of adenine, guanine, cytosine, thymine, 7-deazaguanine, 7-deazaadenine or 5-methylcytosine.

In an embodiment the methods further comprise a washing step after each iteration of step (b) to remove unincorporated dNPP analogues from contact with the single-stranded DNA.

In an embodiment the methods further comprise a washing step after each iteration of step (c) to remove unincorporated dNPP analogues from contact with the single-stranded DNA.

In an embodiment the methods further comprise wherein the single-stranded DNA, electrolyte solution and nanopore in the membrane are located within a single container.

In an embodiment of the methods wherein $R_1$ is —O—CH$_2$N$_3$, the methods optionally further comprise treating the incorporated dNPP analogue so as to remove the —CH$_2$N$_3$ and result in an OH group attached to the 3' position thereby permitting incorporation of a further dNPP analogue.

In an embodiment of the methods wherein $R_1$ is —O-2-nitrobenzyl, the methods optionally further comprise treating the incorporated nucleotide analogue so as to remove the -2-nitrobenzyl and result in an OH group attached to the 3' position thereby permitting incorporation of a further dNPP analogue.

In an embodiment of the methods the dNPP analogues have the following structures:

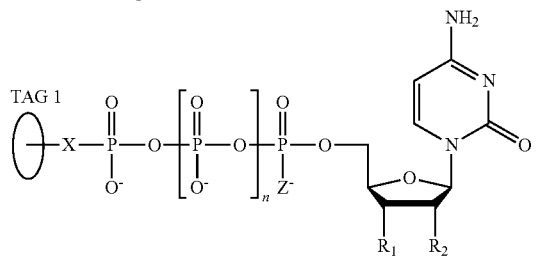

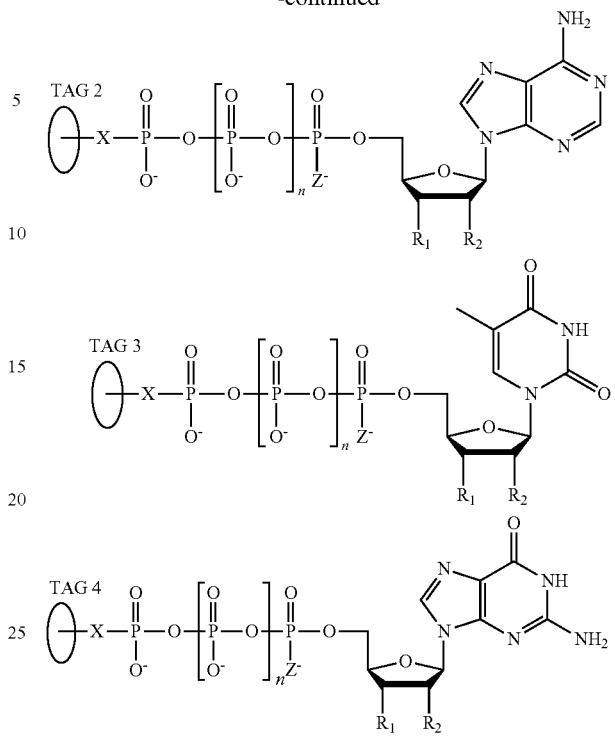

wherein $R_1$ is OH, wherein $R_2$ is H or OH, wherein Z is O, S, or BH$_3$, and wherein the base is adenine, guanine, cytosine, thymine, uracil, a 7-deazapurine or a 5-methylpyrimidine.

In an embodiment of the methods the tag is a mononucleotide, a dinucleotide, a trinucleotide, a tetranucleotide, a pentanucleotide or a hexanucleotide and wherein the base of the mononucleotide, the dinucleotide, the trinucleotide, the tetranucleotide, the pentanucleotide or the hexanucleotide is the same type of base as the base of the dNPP analogue.

In an embodiment of the methods the tag is chosen from the following:

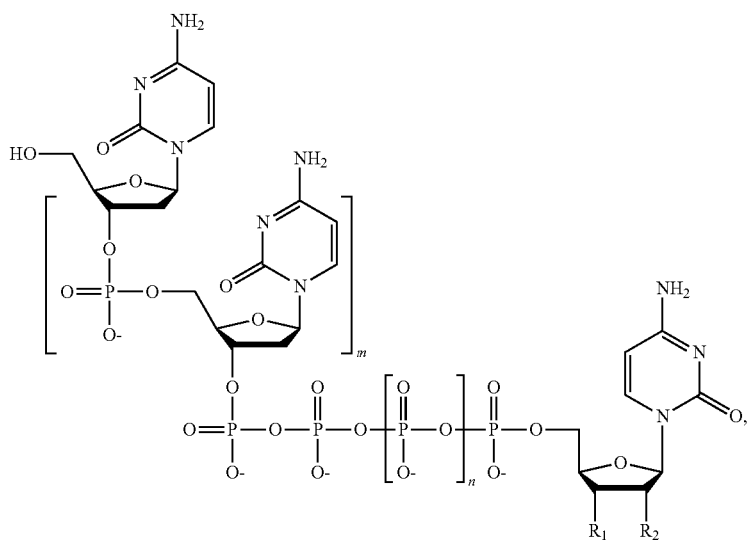

(dCp)$_m$-(PO$_4$)$_n$-dC

-continued
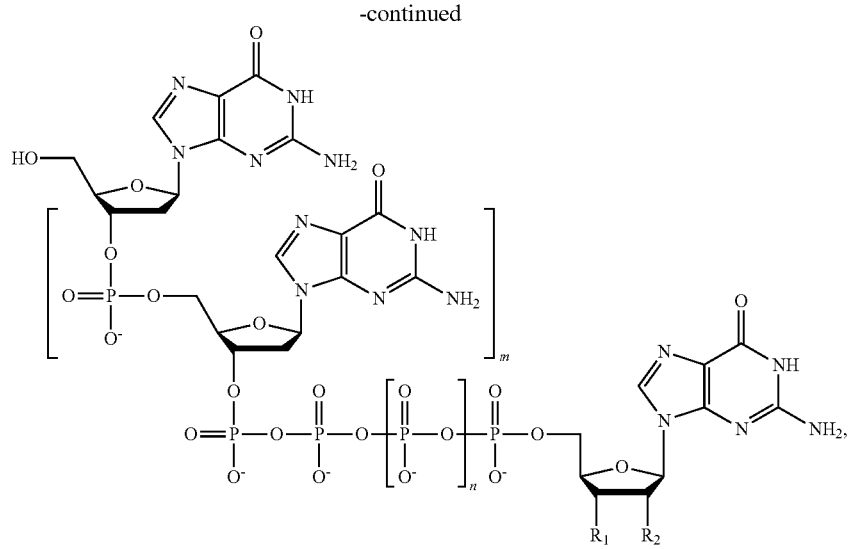
(dGp)$_m$-(PO$_4$)$_n$-dG
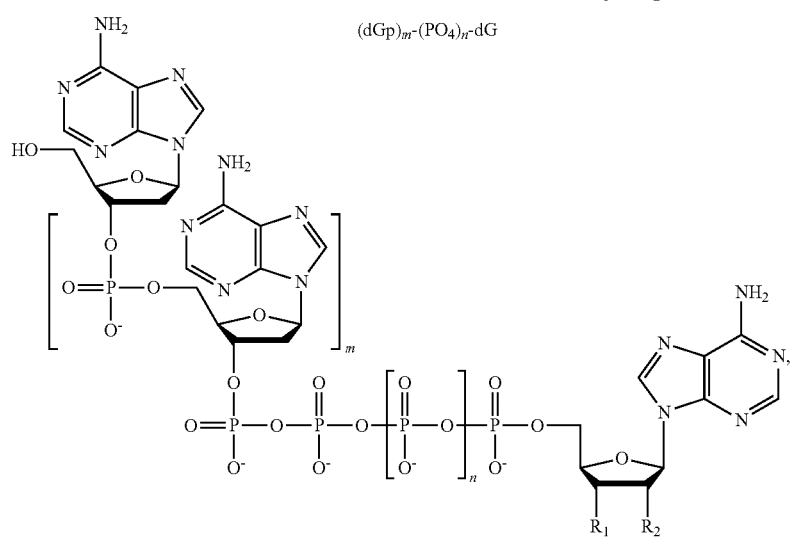
(dAp)$_m$-(PO$_4$)$_n$-dA
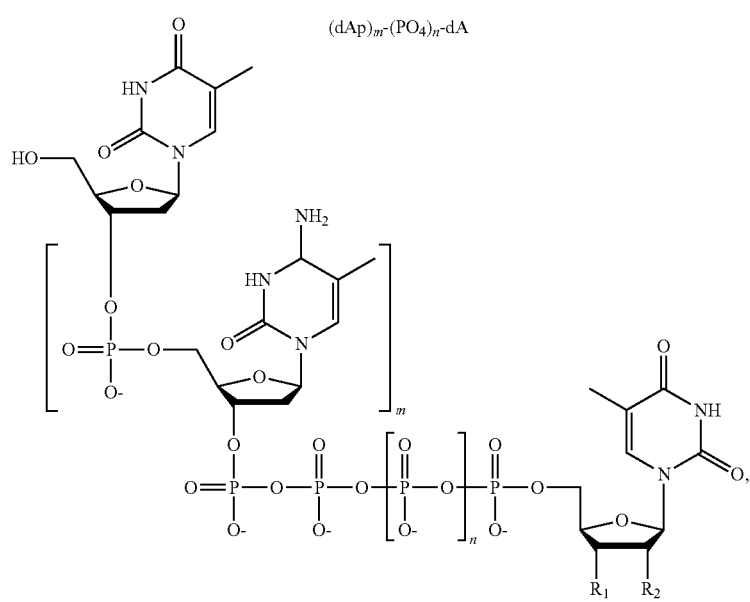
(dTp)$_m$-(PO$_4$)$_n$-dT wherein in each structure n is, independently, 1, 2, 3 or 4, and m is, independently, an integer from 0 to 100, and wherein when m is 0 the terminal phosphate of the dNPP is bonded directly to the 3' O atom of the nucleoside shown on the left hand side of the structure, and wherein the value of n is different for each type of base.

In an embodiment of the methods m is an integer from 0 to 50. In an embodiment of the methods m is an integer from 0 to 10.

In an embodiment of the methods the dNPP analogue has the structure:

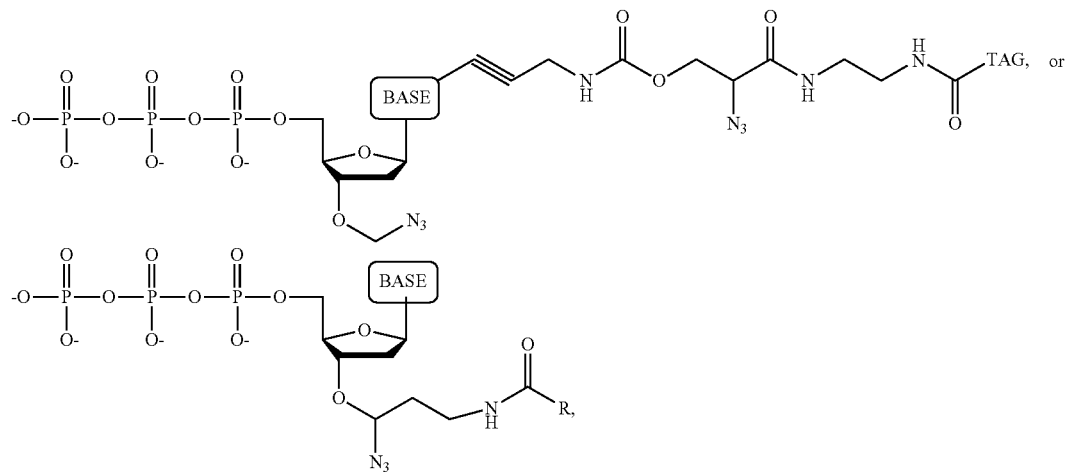

wherein R is a substituted or unsubstituted hydrocarbyl, up to 3000 daltons, and wherein the base is adenine, guanine, cytosine, thymine, uracil, a 7-deazapurine or a 5-methylpyrimidine.

In an embodiment of the methods the dNPP analogue has the structure:

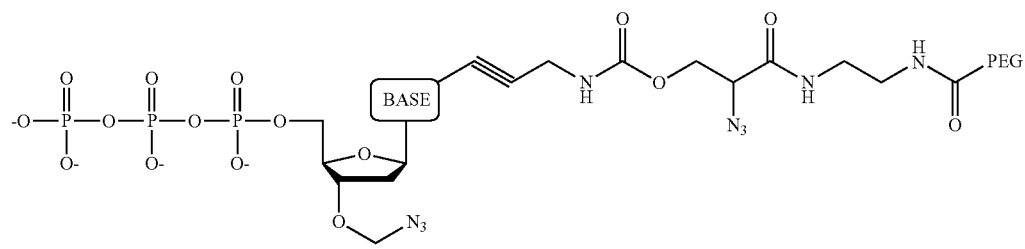

wherein the base is adenine, guanine, cytosine, thymine, uracil, a 7-deazapurine or a 5-methylpyrimidine.

In an embodiment of the methods the dNPP analogue has the structure:

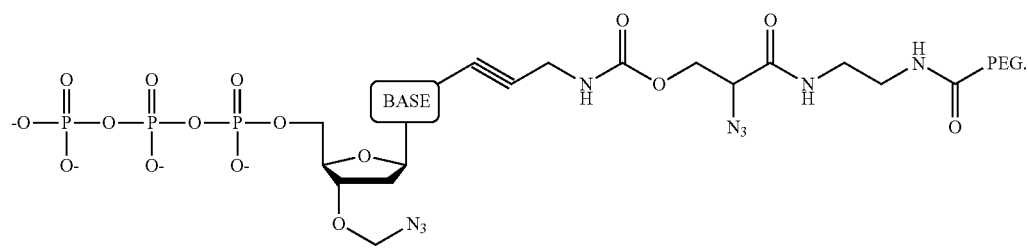

In an embodiment of the methods the dNPP analogue has the structure:

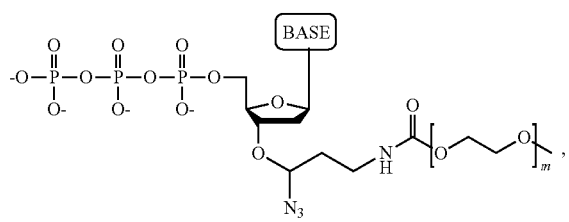

wherein m is an integer from 1-50, and wherein the base is adenine, guanine, cytosine, thymine, uracil, a 7-deazapurine or a 5-methylpyrimidine.

In an embodiment of the methods the electronic change is a change in current amplitude.

In an embodiment of the methods the electronic change is a change in conductance of the nanopore.

In an embodiment of the methods the nanopore is biological. In an embodiment of the methods the nanopore is proteinaceous. In an embodiment of the methods the nanopore comprises alpha hemolysin. In an embodiment of the methods the nanopore is graphene. In an embodiment of the methods the nanopore is a solid-state nanopore. In an embodiment of the methods the nanopore is in a solid-state membrane.

In an embodiment of the methods the single stranded DNA, the primer, or the DNA polymerase is attached to a solid surface.

In another embodiment of the methods the nanopore is part of an array of nanopores.

A process for producing a nucleotide triphosphate analogue, wherein the nucleotide triphosphate analogue differs from a nucleotide triphosphate by having a tag attached to the terminal phosphate thereof, comprising:

a) contacting a nucleotide triphosphate with dicyclohexylcarbodiimide/dimethylformamide under conditions permitting production of a cyclic trimetaphosphate;

b) contacting the product resulting from step a) with a tag having a hydroxyl or amino group attached thereto under conditions permitting nucleophilic opening of the cyclic trimetaphosphate so as to bond the tag to a terminal phosphate thereby forming the nucleotide triphosphate analogue.

A process for producing a nucleotide triphosphate analogue, wherein the nucleotide triphosphate analogue differs from a nucleotide triphosphate by having a tag attached to the terminal phosphate thereof, comprising:

a) contacting a nucleotide triphosphate with dicyclohexylcarbodiimide/dimethylformamide under conditions permitting production of a cyclic trimetaphosphate;

b) contacting the product resulting from step a) with a nucleophile so as to form an —OH or —NH$_2$ functionalized compound;

c) reacting the product of step b) with a tag having a —COR group attached thereto under conditions permitting the tag to bond indirectly to a terminal phosphate thereby forming the nucleotide triphosphate analogue.

In an embodiment of the instant process the nucleophile is H$_2$N—R—OH, H$_2$N—R—NH$_2$, R'S—R—OH, R'S—R—NH$_2$, or

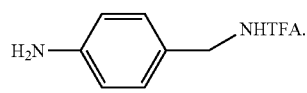

In an embodiment the instant process comprises in step b) contacting the product resulting from step a) with a compound having the structure:

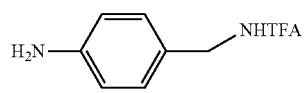

and then NH$_4$OH so as to form a compound having the structure:

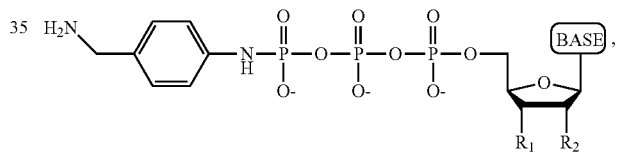

and reacting the product of step b) with a tag having a —COR group attached thereto under conditions permitting the tag to bond indirectly to a terminal phosphate thereby forming the nucleotide triphosphate analogue having the structure:

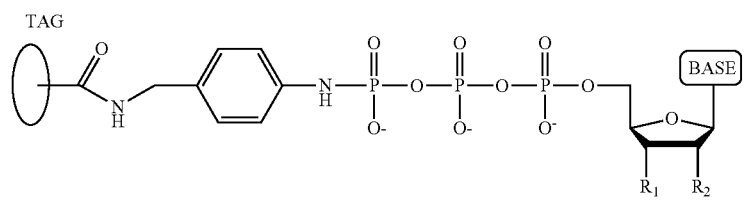

wherein $R_1$ is OH, wherein $R_2$ is H or OH, wherein the base is adenine, guanine, cytosine, thymine, uracil, a 7-deazapurine or a 5-methylpyrimidine.

A process for producing a nucleotide tetraphosphate analogue, wherein the nucleotide tetraphosphate analogue differs from a nucleotide tetraphosphate by having a tag attached to the terminal phosphate thereof, comprising:

a) contacting a nucleotide triphosphate with 1,1'-carbonyldiimidazole/dimethylformamide under conditions permitting formation of the following structure:

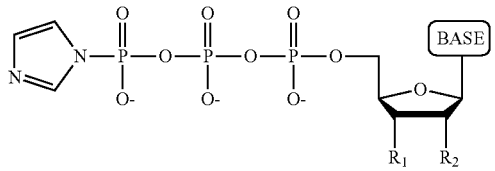

wherein $R_1$ is OH, wherein $R_2$ is H or OH, wherein the base is adenine, guanine, cytosine, thymine, uracil, a 7-deazapurine or a 5-methylpyrimidine;
b) contacting the product resulting from step a) with a tag having a monophosphate group attached thereto under conditions permitting formation of the nucleotide tetraphosphate analogue.

A process for producing a nucleotide tetraphosphate analogue, wherein the nucleotide tetraphosphate analogue differs from a nucleotide tetraphosphate by having a tag attached to the terminal phosphate thereof, comprising:
a) contacting a nucleotide triphosphate with 1,1'-carbonyldiimidazole/dimethylformamide under conditions permitting formation of the following structure:

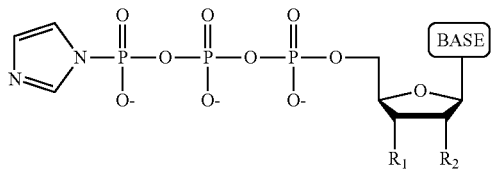

wherein $R_1$ is OH, wherein $R_2$ is H or OH, wherein the base is adenine, guanine, cytosine, thymine, uracil, a 7-deazapurine or a 5-methylpyrimidine;
b) contacting the product resulting from step a) with phosphoric acid under conditions permitting formation of a nucleotide tetraphosphate;
c) contacting the nucleotide tetraphosphate with 1) carbonyldiimidazole/dimethylformamide; 2) a nucleophile and then 3) $NH_4OH$ so as to form an —OH or —$NH_2$ functionalized compound;
d) contacting the product of step c) with a tag having a —COR group attached thereto under conditions permitting the tag to bond indirectly to a terminal phosphate thereby forming the nucleotide tetraphosphate analogue.

In an embodiment of the instant process the nucleophile is $H_2N$—R—OH, $H_2N$—R—$NH_2$, R'S—R—OH, R'S—R—$NH_2$, or

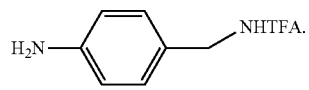

In an embodiment the instant process comprises in step b) contacting the nucleotide tetraphosphate with 1) carbonyldiimidazole/dimethylformamide; 2) a compound having the structure:

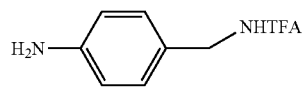

and then 3) $NH_4OH$ so as to form a compound having the structure:

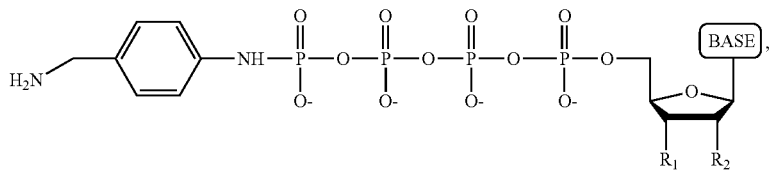

and contacting the product of step b) with a tag having a —COR group attached thereto under conditions permitting the tag to bond indirectly to a terminal phosphate thereby forming the nucleotide triphosphate analogue having the structure:

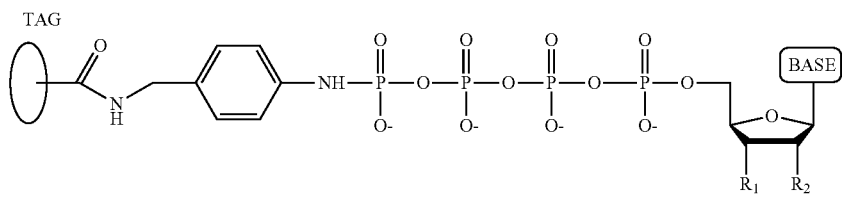

wherein $R_1$ is OH, wherein $R_2$ is H or OH, wherein the base is adenine, guanine, cytosine, thymine, uracil, a 7-deazapurine or a 5-methylpyrimidine.

A process for producing a nucleotide tetraphosphate analogue, wherein the nucleotide tetraphosphate analogue differs from a nucleotide tetraphosphate by having a tag attached to the terminal phosphate thereof, comprising:
 a) contacting a nucleotide triphosphate with 1,1'-carbonyldiimidazole/dimethylformamide under conditions permitting formation of the following structure:

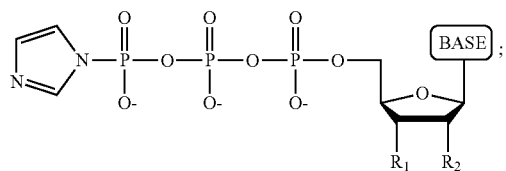

b) contacting the product resulting from step a) with phosphoric acid under conditions permitting formation of a nucleotide tetraphosphate;
 c) contacting the nucleotide tetraphosphate with carbonyldiimidazole/dimethylformamide and a tag having a hydroxyl or amino group attached thereto so as to form a compound having the structure:

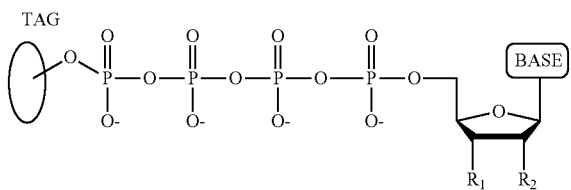

wherein $R_1$ is OH, wherein $R_2$ is H or OH, wherein the base is adenine, guanine, cytosine, thymine, uracil, a 7-deazapurine or a 5-methylpyrimidine.

A process for producing a nucleotide pentaphosphate analogue, wherein the nucleotide pentaphosphate analogue differs from a nucleotide pentaphosphate by having a tag attached to the terminal phosphate thereof, comprising:
 a) contacting a nucleotide triphosphate with 1,1'-carbonyldiimidazole/dimethylformamide under conditions permitting formation of the following structure:

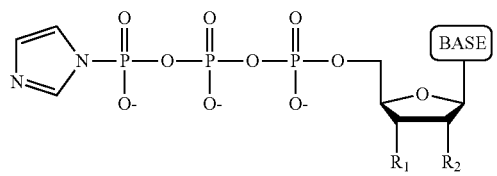

wherein $R_1$ is OH, wherein $R_2$ is H or OH, wherein the base is adenine, guanine, cytosine, thymine, uracil, a 7-deazapurine or a 5-methylpyrimidine;
 b) contacting the product resulting from step a) with a tag having a pyrophosphate group attached thereto under conditions permitting formation of the nucleotide pentaphosphate analogue.

A process for producing a nucleotide pentaphosphate analogue, wherein the nucleotide pentaphosphate analogue differs from a nucleotide pentaphosphate by having a tag attached to the terminal phosphate thereof, comprising:
 a) contacting a nucleotide triphosphate with 1,1'-carbonyldiimidazole/dimethylformamide under conditions permitting formation of the following structure:

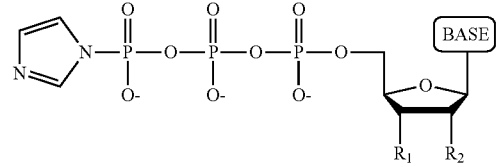

wherein $R_1$ is OH, wherein $R_2$ is H or OH, wherein the base is adenine, guanine, cytosine, thymine, uracil, a 7-deazapurine or a 5-methylpyrimidine;
 b) contacting the product resulting from step a) with a pyrophosphate group under conditions permitting formation of a nucleotide pentaphosphate;
 c) contacting the nucleotide pentaphosphate with carbonyldiimidazole/dimethylformamide and a tag having a hydroxyl or amino group attached thereto so as to form the nucleotide pentaphosphate analogue.

A process for producing a nucleotide hexaphosphate analogue, wherein the nucleotide hexaphosphate analogue differs from a nucleotide hexaphosphate by having a tag attached to the terminal phosphate thereof, comprising:
 a) contacting a nucleotide triphosphate with 1,1'-carbonyldiimidazole/dimethylformamide under conditions permitting formation of the following structure:

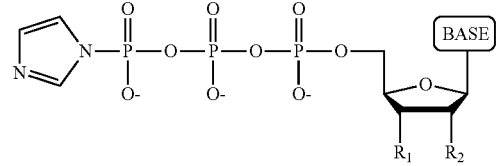

wherein $R_1$ is OH, wherein $R_2$ is H or OH, wherein the base is adenine, guanine, cytosine, thymine, uracil, a 7-deazapurine or a 5-methylpyrimidine;
 b) contacting the product resulting from step a) with a tag having a triphosphate group attached thereto under conditions permitting formation of the nucleotide hexaphosphate analogue.

A process for producing a nucleotide hexaphosphate analogue, wherein the nucleotide hexaphosphate analogue differs from a nucleotide hexaphosphate by having a tag attached to the terminal phosphate thereof, comprising:
 a) contacting a nucleotide triphosphate with 1,1'-carbonyldiimidazole/dimethylformamide under conditions permitting formation of the following structure:

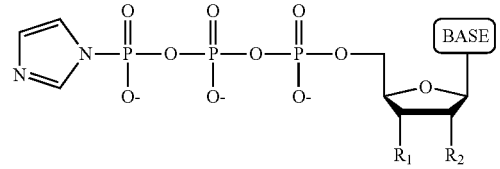

wherein $R_1$ is OH, wherein $R_2$ is H or OH, wherein the base is adenine, guanine, cytosine, thymine, uracil, a 7-deazapurine or a 5-methylpyrimidine;
 b) contacting the product resulting from step a) with a triphosphate group under conditions permitting formation of a nucleotide hexaphosphate;

c) contacting the nucleotide hexaphosphate with carbonyldiimidazole/dimethylformamide and a tag having a hydroxyl or amino group attached thereto so as to form the nucleotide hexaphosphate analogue.

A compound having the structure:

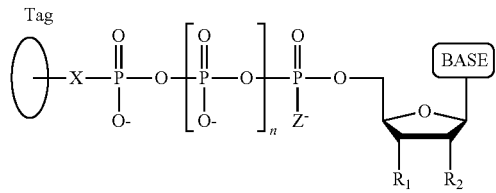

wherein the tag is ethylene glycol, an amino acid, a carbohydrate, a dye, mononucleotide, dinucleotide, trinucleotide, tetranucleotide, pentanucleotide or hexanucleotide, wherein $R_1$ is OH, wherein $R_2$ is H or OH, wherein X is O, NH, S or $CH_2$, wherein Z is O, S, or $BH_3$, wherein the base is adenine, guanine, cytosine, thymine, uracil, a 7-deazapurine or a 5-methylpyrimidine, and wherein n is 1, 2, 3, or 4.

In an embodiment $R_2$ is H. In an embodiment $R_2$ is OH.

A compound having the structure:

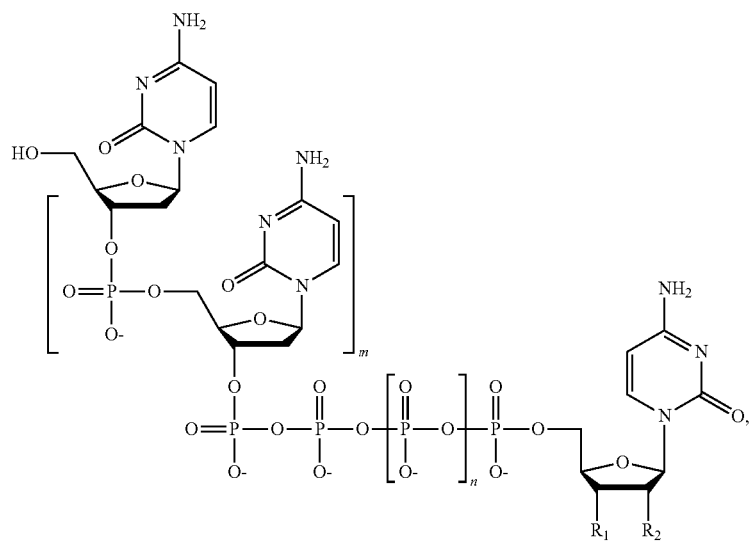

$(dCp)_m\text{-}(PO_4)_n\text{-}dC$

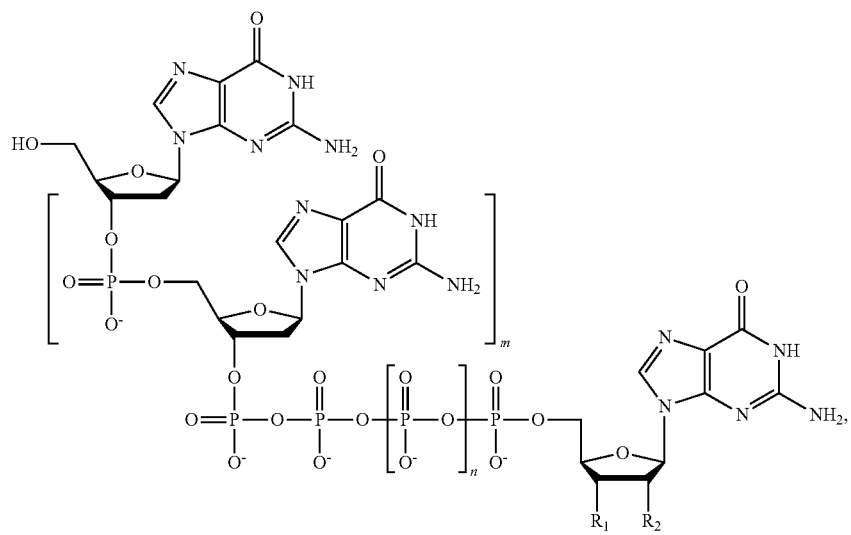

$(dGp)_m\text{-}(PO_4)_n\text{-}dG$

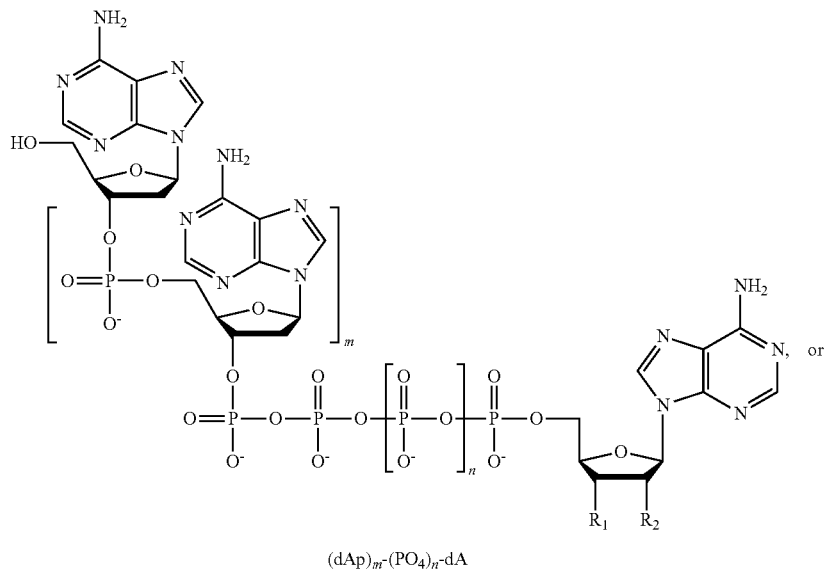
(dAp)$_m$-(PO$_4$)$_n$-dA
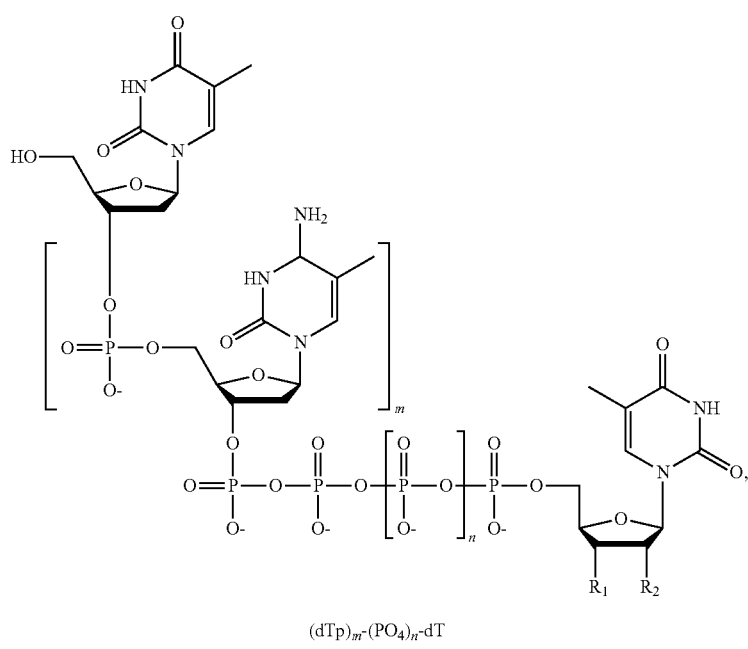
(dTp)$_m$-(PO$_4$)$_n$-dT
wherein in each structure n is, independently, 1, 2, 3 or 4, and m is, independently, an integer from 0 to 100, and wherein when m is 0 the terminal phosphate of the dNTP is bonded directly to the 3' O atom of the nucleoside shown on the left hand side of the structure, wherein R$_1$ is —OH, or —O—CH$_2$N$_3$, and R$_2$ is H or OH.

In an embodiment m is from 0 to 50. In an embodiment m is from 0 to 10. In an embodiment $R_1$ is —OH. In an embodiment $R_2$ is —H. In an embodiment $R_2$ is —OH.

A compound having the structure:

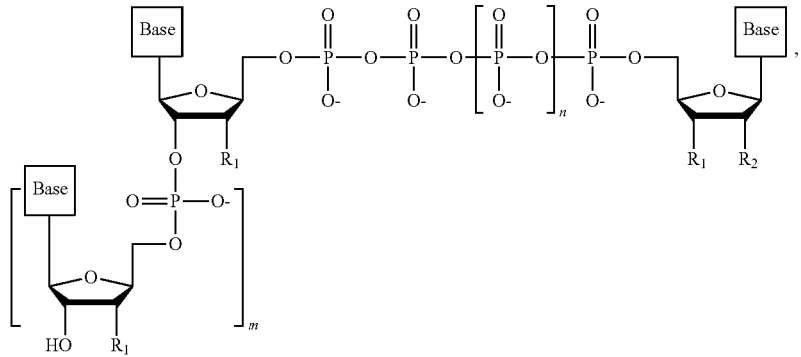

wherein m an integer from 0 to 100, and wherein the compound comprises a single type of base, and wherein the base is adenine, guanine, cytosine, uracil or thymine or a derivative thereof of each.

In an embodiment m is from 0 to 50. In an embodiment m is from 0 to 10.

In an embodiment the compound has the structure:

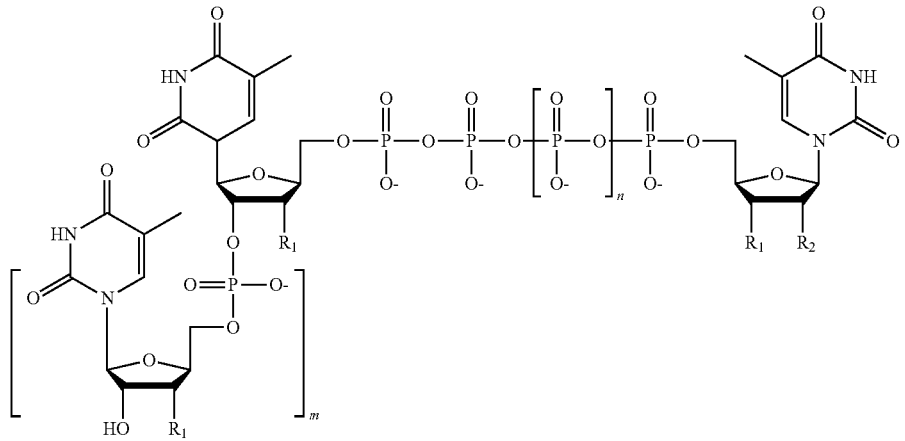

wherein m is an integer from 0 to 100.

A compound having the structure:

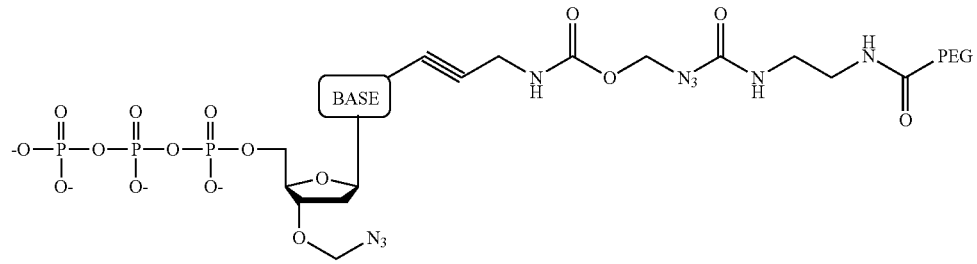

wherein the base is adenine, guanine, cytosine, thymine, uracil, a 7-deazapurine or a 5-methylpyrimidine.

45

A compound having the structure:

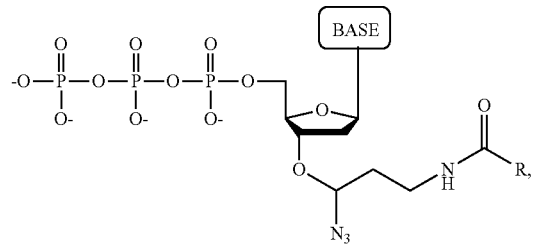

wherein the base is adenine, guanine, cytosine, thymine, uracil, a 7-deazapurine or a 5-methylpyrimidine, and R is a substituted or unsubstituted hydrocarbyl, up to 3000 daltons.

A compound having the structure:

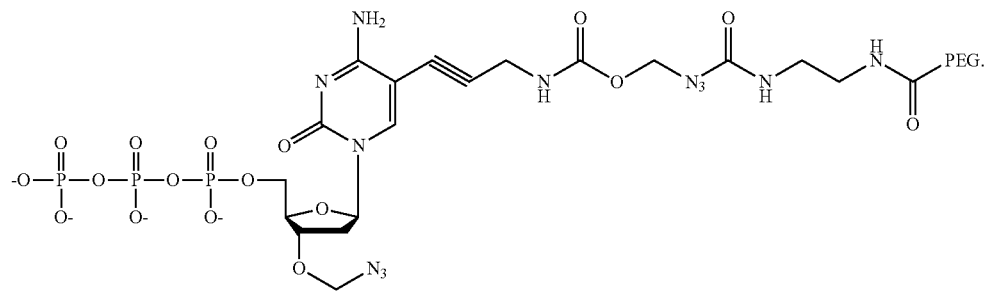

A compound having the structure:

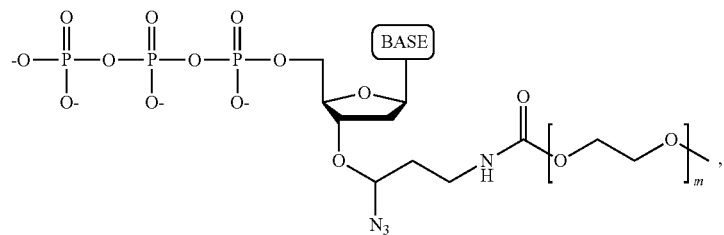

wherein the base is adenine, guanine, cytosine, thymine, uracil, a 7-deazapurine or a 5-methylpyrimidine, and m is an integer from 1-50.

A compound having the structure:

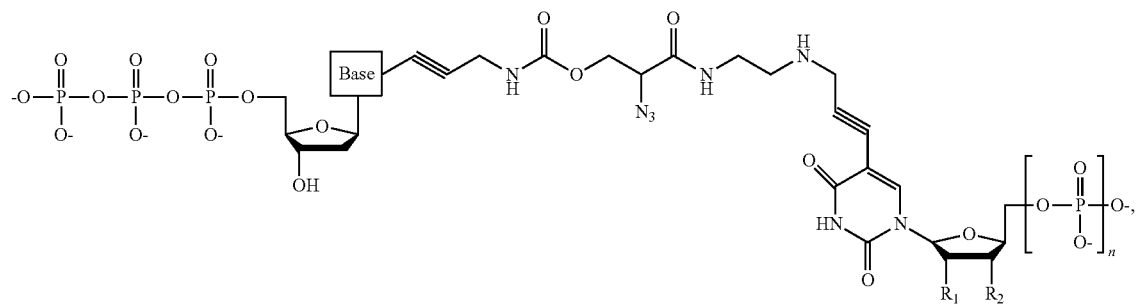

wherein n is 1 or 2 and the base is adenine, guanine, cytosine, thymine, uracil, a 7-deazapurine or a 5-methylpyrimidine.

46

A compound having the structure:

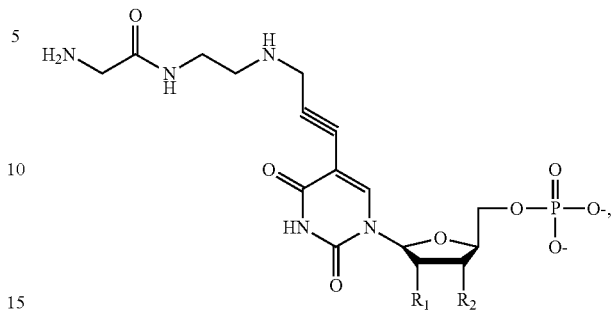

47
-continued

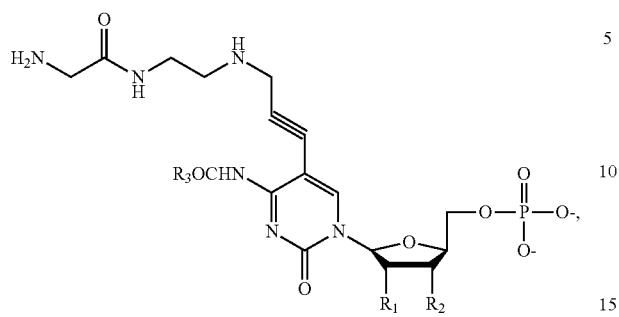

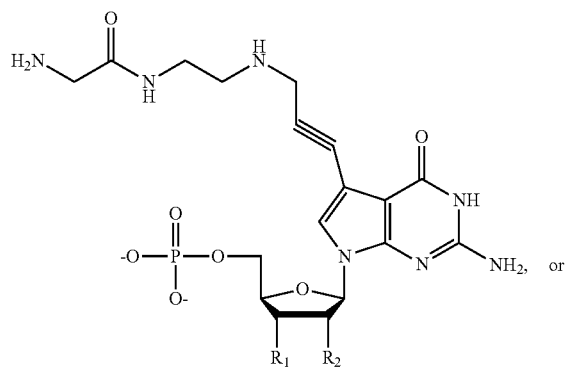

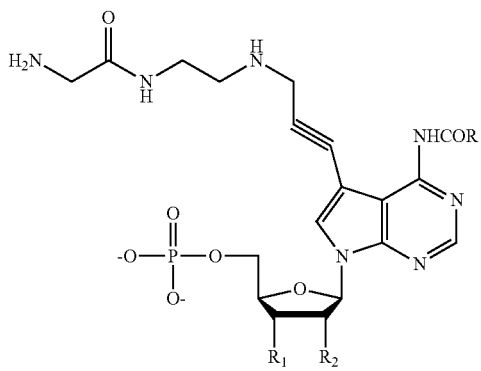

wherein R₁ is —OH, or —O—CH₂N₃, and R₂ is H or OH.

A method for determining the nucleotide sequence of a single-stranded RNA comprising:

(a) contacting the single-stranded RNA, wherein the single-stranded RNA is in an electrolyte solution in contact with a nanopore in a membrane, wherein the single-stranded RNA has a primer hybridized to a portion thereof, with a RNA polymerase and at least four ribonucleotide polyphosphate (rNPP) analogues under conditions permitting the RNA polymerase to catalyze incorporation of one of the rNPP analogues into the primer if it is complementary to the nucleotide residue of the single-stranded RNA which is immediately 5' to a nucleotide residue of the single-stranded RNA hybridized to the 3' terminal nucleotide residue of the primer, so as to form a RNA extension product, wherein each of the four rNPP analogues has the structure:

48

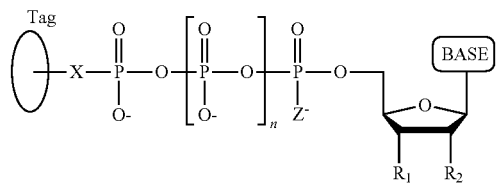

wherein the base is adenine, guanine, cytosine, thymine or uracil, or a derivative thereof of each, wherein R₁ is OH, wherein R₂ is OH, wherein X is O, NH, S or CH₂, wherein n is 1, 2, 3, or 4, wherein Z is O, S, or BH₃, and with the proviso that (i) the type of base on each rNPP analogue is different from the type of base on each of the other three rNPP analogues, and (ii) either the value of n of each rNPP analogue is different from the value of n of each of the other three rNPP analogues, or the value of n of each of the four rNPP analogues is the same and the type of tag on each rNPP analogue is different from the type of tag on each of the other three rNPP analogues, wherein incorporation of the rNPP analogue results in release of a polyphosphate having the tag attached thereto; and (b) determining which rNPP analogue has been incorporated into the primer to form a RNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, as appropriate, thereby identifying the nucleotide residue in the single-stranded RNA complementary to the incorporated rNPP analogue; and (c) iteratively performing steps (a) and (b) for each nucleotide residue of the single-stranded RNA being sequenced, wherein in each iteration of step (a) the rNPP analogue is incorporated into the RNA extension product resulting from the previous iteration of step (a) if it is complementary to the nucleotide residue of the single-stranded RNA which is immediately 5' to a nucleotide residue of the single-stranded RNA hybridized to the 3' terminal nucleotide residue of the RNA extension product, thereby determining the nucleotide sequence of the single-stranded RNA.

A method for determining the nucleotide sequence of a single-stranded RNA comprising:

(a) contacting the single-stranded RNA, wherein the single-stranded RNA is in an electrolyte solution in contact with a nanopore in a membrane and wherein the single-stranded RNA has a primer hybridized to a portion thereof, a RNA polymerase and a ribonucleotide polyphosphate (rNPP) analogue under conditions permitting the RNA polymerase to catalyze incorporation of the rNPP analogue into the primer if it is complementary to the nucleotide residue of the single-stranded RNA which is immediately 5' to a nucleotide residue of the single-stranded RNA hybridized to the 3' terminal nucleotide residue of the primer, so as to form a RNA extension product, wherein the rNPP analogue has the structure:

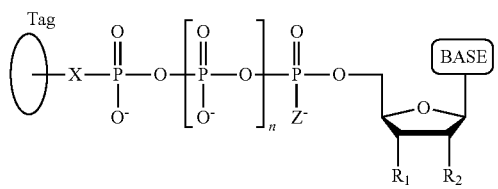

wherein the base is adenine, guanine, cytosine, uracil or thymine, wherein $R_1$ is —OH, —O—CH$_2$N$_3$ or —O-2-nitrobenzyl, wherein $R_2$ is —OH, wherein X is O, NH, S or CH$_2$, wherein n is 1, 2, 3, or 4, wherein Z is O, S, or BH$_3$, and wherein if the rNPP analogue is not incorporated, iteratively repeating the contacting with a different rNPP analogue until a rNPP analogue is incorporated, with the proviso that (1) the type of base on each rNPP analogue is different from the type of base on each of the other rNPP analogues, and (2) either the value of n of each rNPP analogue is different from the value of n of each of the other three rNPP analogues, or the value of n of each of the four rNPP analogues is the same and the type of tag on each rNPP analogue is different from the type of tag on each of the other three rNPP analogues, wherein incorporation of a rNPP analogue results in release of a polyphosphate having the tag attached thereto;

(b) determining which rNPP analogue has been incorporated into the primer to form a RNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or different for each type of tag, as appropriate, thereby identifying the nucleotide residue in the single-stranded RNA complementary to the incorporated dNPP analogue;

(c) iteratively performing steps (a) and (b) for each nucleotide residue of the single-stranded RNA being sequenced, wherein in each iteration of step (a) the rNPP analogue is incorporated into the RNA extension product resulting from the previous iteration of step (a) if it is complementary to the nucleotide residue of the single-stranded RNA which is immediately 5' to a nucleotide residue of the single-stranded RNA hybridized to the 3' terminal nucleotide residue of the RNA extension product, thereby determining the nucleotide sequence of the single-stranded RNA.

In an embodiment the dNPP analogue has the structure:

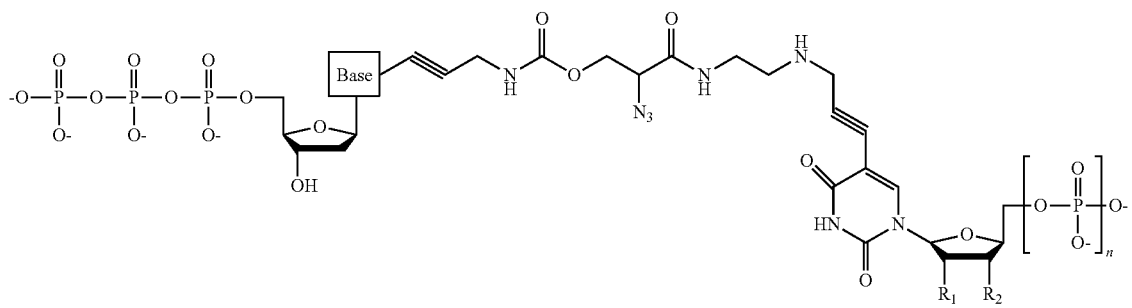

wherein n is 1 or 2 and the base is adenine, guanine, cytosine, thymine, uracil, a 7-deazapurine or a 5-methylpyrimidine.

In an embodiment the biological nanopore is integrated with CMOS electronics. In another embodiment the solid-state nanopore is integrated with CMOS electronics.

In an embodiment the attachment to the solid surface is via biotin-streptavidin linkages. In another embodiment the DNA polymerase is attached to the solid surface via gold surface modified with an alkanethiol self-assembled monolayer functionalized with amino groups, wherein the amino groups are modified to NHS esters for attachment to amino groups on the DNA polymerase.

In one embodiment the dNPP analogue is a terminal-phosphate-tagged nucleoside-polyphosphate. In a further embodiment each type of dNPP analogue has a polyethylene glycol tag which differs in size from the polyethylene glycol tags of each of the other three types of dNPP analogues.

In one embodiment the tag has the structure as follows:

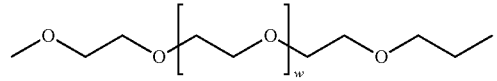

wherein W is an integer between 0 and 100.

In another embodiment the tag has the structure as follows:

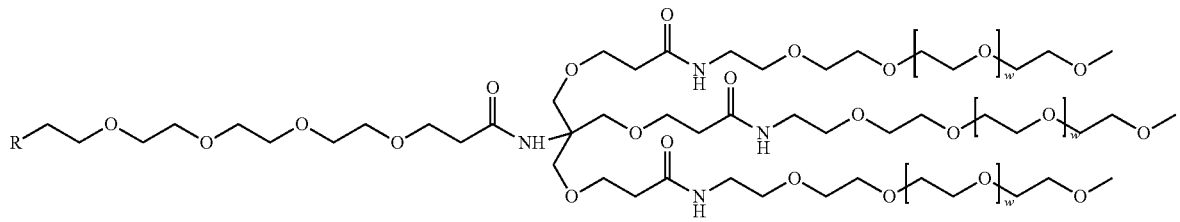

wherein R is NH$_2$, OH, COOH, CHO, SH, or N$_3$, and W is an integer from 0 to 100.

A composition comprising at least four deoxynucleotide polyphosphate (dNPP) analogues, wherein each of the four dNPP analogues comprises a type of base different from the type of base of the other three dNPP analogues.

In one embodiment, each of the four dNPP analogues has a polyethylene glycol tag which is different in size from the polyethylene glycol tags of each of the other three dNPP analogues.

In an embodiment net charge on the tagged nucleoside polyphosphate is neutral. In another embodiment the released tag has a positive charge.

In one embodiment, the method further comprising a step of treating with alkaline phosphatase after step b), wherein the alkaline phosphatase hydrolyzes free phosphate groups on the released tag-pyrophosphate.

In one embodiment multiple copies of the single-stranded DNA are immobilized on a bead.

A "derivative" of adenine, guanine, cytosine, thymine or uracil, include a 7-deaza-purine and a 5-methyl pyrimidine. Examples include 7-deaza adenine, 7-deaza-guanine, and 5-methyl-cytosine.

The present invention also provides a compound having the structure of any of the compounds set forth in the figures and/or schemes of the present application.

The present invention also provides a dNPP analogue comprising a tag having the structure of any of the tags set forth in the figures and/or schemes of the present application.

In an embodiment, the tag is a hydrocarbyl, substituted or unsubstituted, such as an alkyl, alkenyl, alkynyl, and having a mass of 3000 daltons or less.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" is defined to include groups having 1, 2, ..., n–1 or n carbons in a linear or branched arrangement. For example, a "C1-C5 alkyl" is defined to include groups having 1, 2, 3, 4, or 5 carbons in a linear or branched arrangement, and specifically includes methyl, ethyl, n-propyl, isopropyl, n-butyl, t-butyl, and pentyl As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl radical having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl radical having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. R$_1$, R$_2$, etc. are to be chosen in conformity with well-known principles of chemical structure connectivity.

In the compound structures depicted herein, hydrogen atoms, except on ribose and deoxyribose sugars, are generally not shown. However, it is understood that sufficient hydrogen atoms exist on the represented carbon atoms to satisfy the octet rule.

As used herein, and unless stated otherwise, each of the following terms shall have the definition set forth below.
A—Adenine;
C—Cytosine;
DNA—Deoxyribonucleic acid;
G—Guanine;
RNA—Ribonucleic acid;
T—Thymine; and
U—Uracil.
dNPP—deoxyribonucleotide polyphosphate
rNPP—ribonucleotide polyphosphate "Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

A nucleotide polyphosphate, such as a deoxyribonucleotide polyphosphate ("dNPP") or a ribonucleotide polyphosphate "(rNPP"), is a nucleotide comprising multiple, i.e. three, four, five, six, or more phosphates in a linear fashion bonded to its 5' sugar carbon atom. A nucleotide polyphosphate analogue is an analogue of such a deoxyribonucleotide polyphosphate or of such a ribonucleotide polyphosphate as defined herein, differing thereform by having a tag attached thereto at a specified position. Such analogues are incorporable into a primer or nucleic acid extension strand, such as a DNA extension strand, by contacting with an appropriate nucleic acid polymerase under the appropriate nucleic acid polymerization conditions known to those in the art.

In one embodiment the dNPP is a deoxynucleotide triphosphate.

As used herein a tetranucleotide, a pentanucleotide, or a hexanucleotide, encompasses 4, 5 or 6, respectively, nucleic acid monomer residues joined by phosphodiester bonds, wherein the free terminal residue can be a nucleotide or a nucleoside. In an embodiment, the free terminal residue is a nucleoside and the other residues are nucleotides.

"Solid substrate" shall mean any suitable medium present in the solid phase to which a nucleic acid may be affixed. Non-limiting examples include chips, wells, beads, nanopore structures and columns. In a non-limiting embodiment the solid substrate can be present in a solution, including an aqueous electrolyte solution.

"Hybridize" shall mean the annealing of one single-stranded nucleic acid to another nucleic acid (such as primer) based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analogue capable of forming a phosphodiester bond, therewith.

As used herein, unless otherwise specified, a base which is "different from" another base or a recited list of bases shall mean that the base has a different structure than the other base or bases. For example, a base that is "different from" adenine, thymine, and cytosine would include a base that is guanine or a base that is uracil.

"Primer" as used herein (a primer sequence) is a short, usually chemically synthesized oligonucleotide, of appropriate length, for example about 18-24 bases, sufficient to hybridize to a target DNA (e.g. a single stranded DNA) and permit the addition of a nucleotide residue thereto, or oligonucleotide or polynucleotide synthesis therefrom, under suitable conditions well-known in the art. In an embodiment the primer is a DNA primer, i.e. a primer consisting of, or largely consisting of, deoxyribonucleotide residues. The primers are designed to have a sequence which is the reverse complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product.

In an embodiment the single-stranded DNA, RNA, primer or probe is bound to a solid substrate via 1,3-dipolar azide-alkyne cycloaddition chemistry. In an embodiment the DNA, RNA, primer or probe is bound to a solid substrate via a polyethylene glycol molecule. In an embodiment the DNA, RNA, primer or probe is alkyne-labeled. In an embodiment the DNA, RNA, primer or probe is bound to a solid substrate via a polyethylene glycol molecule and a solid substrate is azide-functionalized In an embodiment the DNA, RNA, primer or probe is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded DNA. In an embodiment the RNA is single-stranded RNA.

In an embodiment the solid substrate is in the form of a chip, a bead, a well, a capillary tube, a slide, a wafer, a filter, a fiber, a porous media, a porous nanotube, or a column. This invention also provides the instant method, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In an embodiment nucleic acid samples, DNA, RNA, primer or probe are separated in discrete compartments, wells or depressions on a surface or in a container.

This invention also provides the instant method, wherein about 1000 or fewer copies of the nucleic acid sample, DNA, RNA, primer or probe, are bound to the solid surface. This invention also provides the instant invention wherein $2 \times 10^7$, $1 \times 10^7$, $1 \times 10^6$ or $1 \times 10^4$ or fewer copies of the nucleic acid sample, DNA, RNA, primer or probe are bound to the solid surface.

In an embodiment the immobilized nucleic acid sample, DNA, RNA, primer or probe is immobilized at a high density. This invention also provides the instant invention wherein over or up to $1 \times 10^7$, $1 \times 10^8$, $1 \times 10^9$ copies of the nucleic acid sample, DNA, RNA, primer or probe, are bound to the solid substrate.

In an embodiment the DNA polymerase is 9° N polymerase or a variant thereof, *E. Coli* DNA polymerase I, Bacteriophage T4 DNA polymerase, Sequenase, Taq DNA polymerase or 9° N polymerase (exo-)A485L/Y409V.

In an embodiment of the methods or of the compositions described herein, the DNA is single-stranded. In an embodiment of the methods or of the compositions described herein, the RNA is single-stranded, Phi29, or variants thereof.

In an embodiment of the methods described for RNA sequencing, the polymerase is an RNA polymerase, reverse transcriptase or appropriate polymerase for RNA polymerization as known in the art.

The linkers may be photocleavable. In an embodiment UV light is used to photochemically cleave the photochemically cleavable linkers and moieties. In an embodiment, the photocleavable linker is a 2-nitrobenzyl moiety.

The —$CH_2N_3$ group can be treated with TCEP (tris(2-carboxyethyl)phosphine) so as to remove it from the 3' O atom of a dNPP analogue, or rNPP analogue, thereby creating a 3' OH group.

Methods for production of cleavably capped and/or cleavably linked nucleotide analogues are disclosed in U.S. Pat. No. 6,664,079, which is hereby incorporated by reference.

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

Because of well-understood base-pairing rules, determining the identity (of the base) of dNPP analogue (or rNPP analogue) incorporated into a primer or DNA extension product (or RNA extension product) by measuring the unique electrical signal of the tag translocating through the nanopore, and thereby the identity of the dNPP analogue (or rNPP analogue) that was incorporated, permits identification of the complementary nucleotide residue in the single stranded polynucleotide that the primer or DNA extension product (or RNA extension product) is hybridized to. Thus, if the dNPP analogue that was incorporated comprises an adenine, a thymine, a cytosine, or a guanine, then the complementary nucleotide residue in the single stranded DNA is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the rNPP analogue that was incorporated comprises an adenine, an uracil, a cytosine, or a guanine, then the complementary nucleotide residue in the single stranded RNA is identified as an uracil, an adenine, a guanine or a cytosine, respectively.

Incorporation into an oligonucleotide or polynucleotide (such as a primer or DNA extension strand) of a dNPP or rNPP analogue means the formation of a phosphodiester bond between the 3' carbon atom of the 3' terminal nucleotide residue of the polynucleotide and the 5' carbon atom of the dNPP analogue or rNPP analogue, respectively.

As used herein, unless otherwise specified, a base (e.g. of a nucleotide polyphosphate analogue) which is different from the type of base of a referenced molecule, e.g. another nucleotide polyphosphate analogue, means that the base has a different chemical structure from the other/reference base or bases. For example, a base that is different from adenine would include a base that is guanine, a base that is uracil, a base that is cytosine, and a base that is thymine. For example, a base that is different from adenine, thymine, and cytosine would include a base that is guanine and a base that is uracil.

As used herein, unless otherwise specified, a tag (e.g. of a nucleotide polyphosphate analogue) which is different from the type of tag of a referenced molecule, e.g. another nucleotide polyphosphate analogue, means that the tag has a different chemical structure from the chemical structure of the other/referenced tag or tags.

"Nanopore" includes, for example, a structure comprising (a) a first and a second compartment separated by a physical barrier, which barrier has at least one pore with a diameter, for example, of from about 1 to 10 nm, and (b) a means for applying an electric field across the barrier so that a charged molecule such as DNA, nucleotide, nucleotide analogue, or tag, can pass from the first compartment through the pore to the second compartment. The nanopore ideally further comprises a means for measuring the electronic signature of a molecule passing through its barrier. The nanopore barrier may be synthetic or naturally occurring in part. Barriers can include, for example, lipid bilayers having therein α-hemolysin, oligomeric protein channels such as porins, and synthetic peptides and the like. Barriers can also include inorganic plates having one or more holes of a suitable size. Herein "nanopore", "nanopore barrier" and the "pore" in the nanopore barrier are sometimes used equivalently.

Nanopore devices are known in the art and nanopores and methods employing them are disclosed in U.S. Pat. Nos. 7,005,264 B2; 7,846,738; 6,617,113; 6,746,594; 6,673,615; 6,627,067; 6,464,842; 6,362,002; 6,267,872; 6,015,714; 5,795,782; and U.S. Publication Nos. 2004/0121525, 2003/0104428, and 2003/0104428, each of which are hereby incorporated by reference in their entirety.

In an embodiment of the molecules and the methods disclosed herein the tag is attached to the remainder of the molecule by a chemical linker which is cleavable.

In an embodiment the nanpore is in a solid-state membrane. In an embodiment the membrane is a silicon nitride membrane. In an embodiment the nanopore is a biopore. In an embodiment the pore is proteinaceous. In an embodiment the pore is an alpha-hemolysin pore. In an embodiment the pore is a graphene pore.

In an embodiment the DNA, RNA or single stranded nucleic acid is located on one side of the membrane in which the nanopore is located and the membrane is located in a conducting electrolyte solution.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS AND DISCUSSIONS

The invention disclosed herein pertains to modified nucleotides for single molecule analysis of DNA (or RNA, mutatis mutandis) using nanopores. Modifications can be made at various positions of a nucleotide, i.e. the terminal phosphate, the base, and/or the 2', or 3'-OH to form a nucleotide analogue. After a polymerase extension reaction on a template-primer complex, the released tag-attached pyrophosphate passes through a nanopore and the resulting current blockage is monitored to determine the nucleotide base added. If the modification or tag is at the base moiety, or the 2'/3'-OH of the sugar moiety of the nucleotide, then after incorporation by DNA/RNA polymerase, the linker-tag is cleaved from the base/sugar by chemical or photochemical means and released linker-tag passes through a nanopore to identify the added nucleotide.

Nucleoside-5'-polyphosphates carrying different number of phosphate groups as linkers and modified with tags attached to the terminal phosphate of the nucleotides are designed and synthesized. After incorporation by DNA/RNA polymerase in a template-primer extension reaction, the released tag-attached polyphosphate (di-, tri-, tetra-, penta-, etc.) can be detected using a nanopore to produce sequence data. Optionally, the released tag-polyphosphates can also be treated with alkaline phosphatase to provide free tags. Using four different tags which are distinct and specific for each nucleotide base, the sequence of the template DNA or RNA can be determined.

Nucleotides carrying different number of phosphate groups or tags for the synthesis of modified nucleotides, which are efficient substrates in polymerase reactions, are provided. The released tag-attached polyphosphate is detected using a nanopore to determine conditions for design and modification of the nucleotides to achieve distinct blockade signals.

Also provided are nucleotides carrying linker-tag attached at the nucleotide base moiety, and/or the 2'/3'-OH of the sugar moiety, for DNA polymerase reaction to generate linker-tag labeled single base DNA extension product. These nucleotides are good substrates for commonly used DNA/RNA polymerases. The linker-tag attached at the extended DNA product is cleaved by chemical or photochemical means to generate the primer ready for further extension using the modified nucleotides. The released linker-tag is passed through nanopore and identified based on the difference in size, shape, and charge on the tag to produce sequence data.

As disclosed herein, these molecular tools facilitate single molecule sequencing using nanopore at single base resolution.

Here are disclosed several improvements to the nanopore approach: 1) to achieve accurate and obvious discrimination of the four bases (A, C, G and T) that make up the nucleic acid molecules; 2) to enhance and differentiate the strength of the detection signals; 3) to develop an effective method for discerning and processing the electronic blockade signals generated; 4) to control the translocation rate of nucleic acids through the pore, such as slowing down the movement of tags to improve the ability of base-to-base discrimination; and 5) to design and make new and more effective synthetic nanopores for differentiating the four different nucleotides in DNA.

Figure 1:
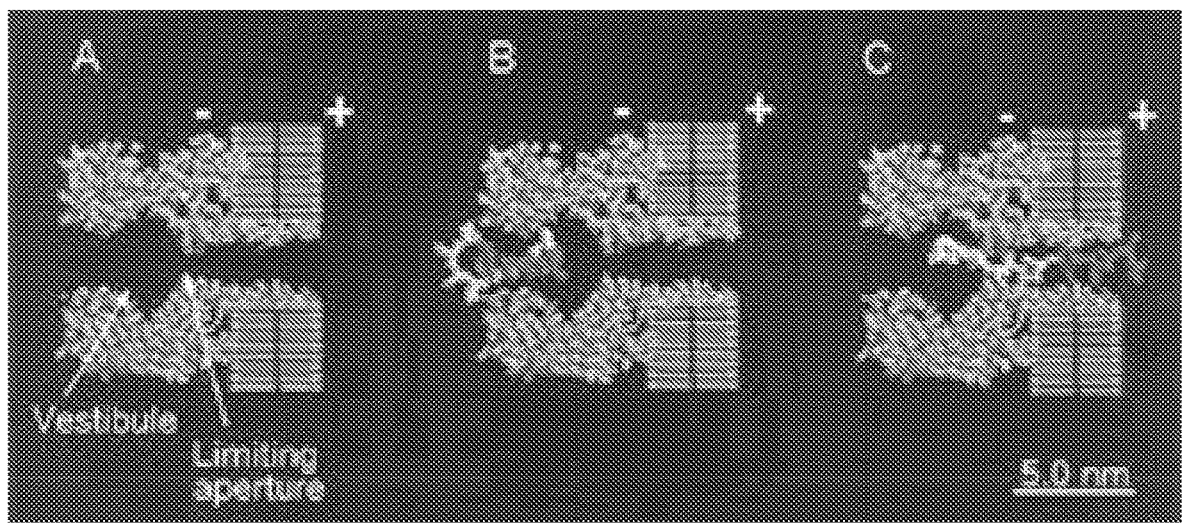
FIG. 1. α-Hemolysin protein self-assembles in a lipid bilayer to form an ion channel and a nucleic acid stretch passes through it (top), with the corresponding electronic signatures generated (bottom) [Vercoutere et al. 2001 and Deamer et al. 2002].
Figure 1:
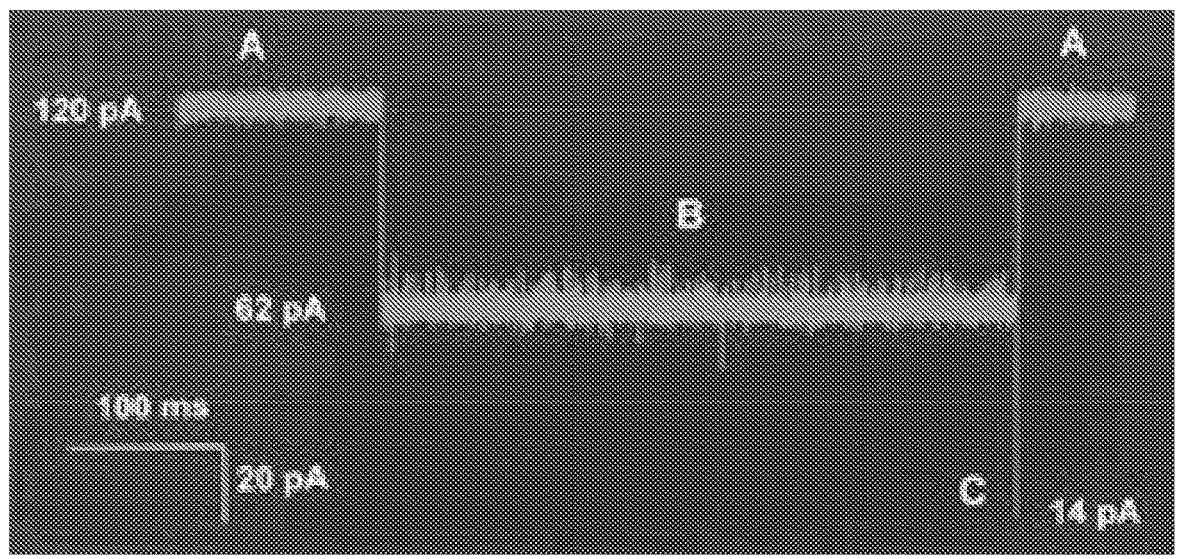
Figure 2:
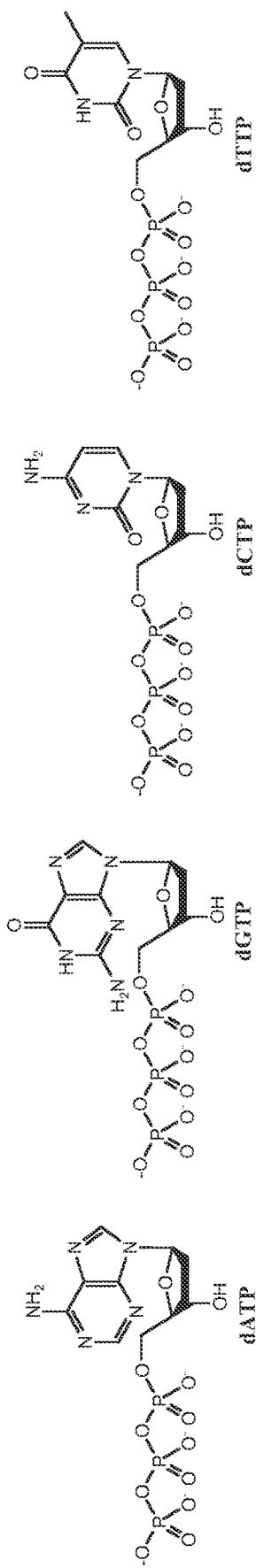
FIG. 2. Structures of nucleotides deoxyribonucleotide adenosine triphosphate, deoxyribonucleotide guanosine triphosphate, deoxyribonucleotide cytosine triphosphate, and deoxyribonucleotide thymidine triphosphate.

The structures of four nucleotides are shown in FIG. 2. A and G are purines, while C and T are pyrimidines. The overall molecular size of A and G is very similar, while the size of C and T is similar. Nanopores have been shown to be able to differentiate between purines and pyrimidines [Akeson et al. 1999 and Meller et al. 2000], but not be able to distinguish between individual purines, A and G, or between individual pyrimidines, C and T.

Previous studies have shown modifications of nucleoside-5'-triphosphates, including introducing more phosphate groups to produce tetra-, penta-, or hexa-phosphates, introducing dye directly to the terminal phosphate, or attaching a linker between the terminal phosphate and the dye [Kumar et al., 2006 and 2008]. Tetra- and penta-phosphates are better DNA polymerase substrates, and dye-labeled hexa-phosphate nucleotides have been developed [Kumar et al. 2005; Sood et al. 2005; Eid et al. 2009].

Figure 3:
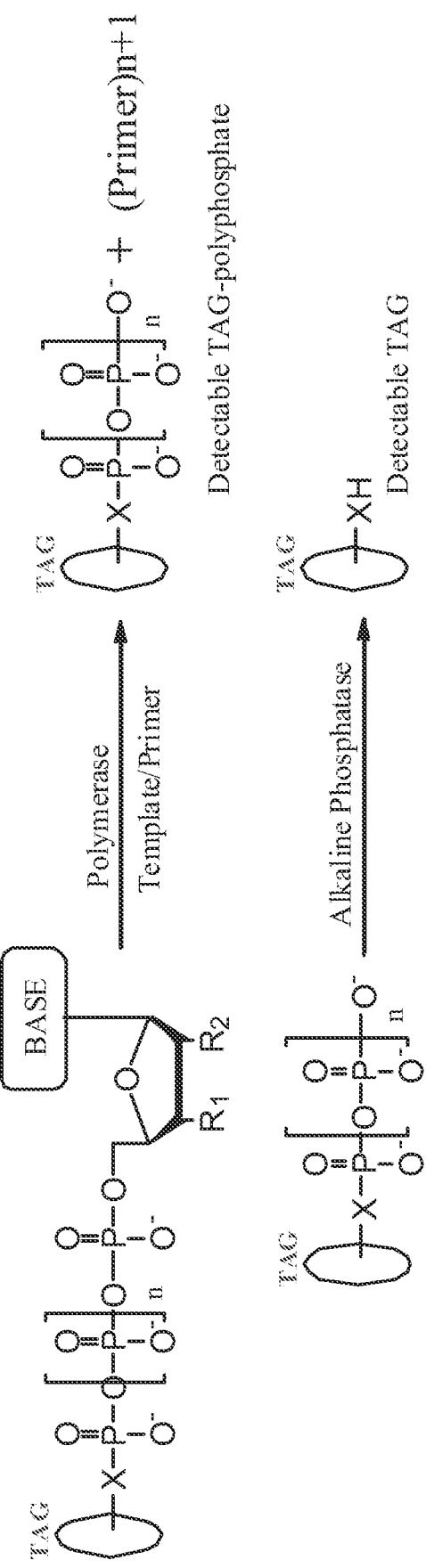
FIG. 3. Mechanism of primer extension and release of tagged-polyphosphate for detection.

Nucleotide analogues which are designed to enhance discrimination of each nucleotide by modification of the nucleotides at the terminal phosphate moiety are disclosed herein. Nucleoside-5'-polyphosphates are synthesized and different tags (such as, different length/mass poly(ethylene glycol)s (PEGs), amino acids, carbohydrates, oligonucleotides, dyes or organic/inorganic molecules) are attached to the terminal phosphate group. After polymerase extension reactions, tag-attached polyphosphate moieties are generated (FIG. 3) and different signal specific to each base is produced when the tag-attached polyphosphate moieties pass through the nanopore. These modifications enlarge the discrimination of the bases by nanopore due to the increased size, mass or charge differences of released tagged-polyphosphate units between the four nucleotides (A, G, C and T).

The DNA translocation rate through the nanopore is reduced due to the bulkiness of the released tag-attached polyphosphates, although the translocation rate of the tags through the nanopore does not need to be reduced as long as the tags can be differentiated. Thus, the accuracy and reliability required for the base-to-base sequencing becomes achievable. Other analytical parameters in nanopore sequencing, such as concentration of the polynucleotide, magnitude of the applied voltage, temperature and pH value of the solution, are optimized in order to get the most accurate and reliable results for the detection and analysis of DNA chain.

Single-molecule approaches to sequencing allow for the possibility of deriving haplotypes for genetic studies and permitting direct sequencing of mRNAs. Among the potential single-molecule approaches for decoding the sequence of DNA or RNA molecules is the use of biological or synthetic nanopores as detectors of the individual DNA bases.

Existing sequencing-by-synthesis (SBS) approach uses cleavable fluorescent nucleotide reversible terminators (CF-NRTs) [Guo et al. 2010]. SBS method is based on the ability to pause after each nucleotide addition during the polymerase reaction and the use of specific fluorophores to discriminate among the bases. However, a major limitation of SBS for single molecule sequencing is the requirement for expensive fluorescence detectors and rapid imaging software. The method and process disclosed herein harness the advantages of SBS, especially its high accuracy, with the speed and sensitivity of the nanopore as an ionic current impedance detector.

While much research has gone into threading DNA through nanopores, with the hope of discriminating each base as it passes through due to its variable effect on the ion current, this has been very hard to achieve, both due to the speed of transmission and the effect of surrounding bases which may contribute their own effects on ions and counter ions passing through the pores [Timp et al. 2010]. The use of cyclodextrins or other ring-shaped structures in the lumen of protein pores help provide a ratcheting mechanism to slow down transit time [Astier et al. 2006], but the ability to absolutely recognize each base for sequencing as it passes remains a challenge. An alternative strategy which uses exonuclease to allow one nucleotide at a time to traverse the pore has led to single base discrimination [Clarke et al. 2009]. However, there is still difficulty in controlling the reaction time of the exonuclease for different lengths of DNA and nucleotide and the speed at which the released ions arrive at the pore with this approach.

Polymerase reaction itself displays high processivity and stable rates of base incorporation. Indeed, polymerase reactions have been used to control the movement of DNA strands through nanopores for direct base discrimination [Benner et al. 2007, Cockroft et al. 2008, Hurt et al. 2009]. During the polymerase reaction, there is release of a pyrophosphate (PPi) moiety. Therefore, if one attaches a different tag to the triphosphate for each of the four nucleotides, these could be discriminated as they are released and pass through an appropriate nanopore for DNA sequence determination. These relatively small pyrophosphate analogs, or equivalent molecules with additional positively charged groups, can reach the pore extremely rapidly. The rate of nucleotide incorporation by polymerases is approximately 1000 nucleotides per second, i.e. a millisecond per base addition, while the transport rate through the nanopore is 1 molecule per microsecond. Thus, with proper fluidics and engineering, there are no de-phasing issues to sequence DNA with our approach, nor are there difficulties with the decoding of homopolymer stretches. It has been shown that one can discriminate among a wide size range of polyethylene glycols differing by as little as one or two carbon units by the effect they have on blocking currents in nanopores [Reiner et al. 2010, Robertson et al. 2007], a resolution essentially equivalent to that obtained by a mass spectrometer. Therefore, as described below, different length PEG chains are attached to the terminal phosphate of dATP, dCTP, dGTP and dTTP. As each nucleotide is incorporated during the polymerase reaction, a specifically tagged phosphate group is released into the nanopore, yielding a distinct current blockade signal to indicate which nucleotide is incorporated. The speed of sequencing is extremely fast, limited only by the rate of the polymerase reaction. As an alternative approach for tagging the nucleotides, we also utilize different phosphate chain lengths (e.g., tri-, tetra-, and penta-phosphates).

Additionally, we also use solid-state nanopores which have advantages in terms of better control over and flexibility of fabrication, thus ensure rapid vectorial transport of tagged polyphosphates but not the nucleotide precursors or the DNA toward and through the nanopores or nanochannels. To achieve this, two important design features are incorporated. First, the precursors (tagged nucleotide polyphosphates) are synthesized with an overall neutral charge, while the cleaved tagged phosphates have an overall positive charge. By utilizing a current that attracts positive ions, the nanopores only need to discriminate the four alternative released tagged molecules. Differential charge on precursors and products are achieved by incorporate into the tags a number of lysines or arginines (positively charged) exactly balancing the number of phosphates (negatively charged). After incorporation of the α-phosphate into the growing primer, there is one more lysine than phosphate in the released product. Optionally, alkaline phosphatase can be used to cleave off all the phosphates to produce a PEG tag with a stronger positive charge. Second, to assure that the released phosphates move immediately through the nearest pore, the DNA polymerase is immobilized to the inlet of the pore, for example via a biotin-streptavidin linkage. As the DNA chain threads through the polymerase, the released tagged products only have to diffuse the same short distance to reach the nanopore.

It is also important to recognize the advantages of the bioelectronic transduction mechanism over optical approaches. For single-molecule optical transduction techniques, the signal from a single-fluorophore is typically <2500 photons/sec (corresponding to detected current levels on the order of 50 fA) at high short noise levels, requiring complex optics to try to collect every photon emitted, making scaling of the platforms to higher densities difficult. Synthesis reactions must be slowed to 1 Hz to allow sufficient integration times for these weak, noisy optical signals. The challenges to optical techniques have opened up the possibility for bioelectronic detection approaches, which have significantly higher signal levels (typically more than three orders of magnitude higher), allowing for the possibility for high-bandwidth detection with the appropriate co-design of transducer, detector, and amplifier. Signal levels for nanopores can be as high as 100 pA from alpha-hemolysin [Kasianowicz et al. 1996], 300 pA for MspA [Derrington et al. 2010], and upwards of 4 nA from solid-state nanopores [Wanunu et al. 2010].

Significant effort has been directed toward the development of nanopore technology as a bioelectronic transduction mechanism [Benner et al. 2007, Deamer et al. 2002, Kasianowicz et al. 1996, Branton 2008, Branton et al. 2008, Chen 2004, Gershow et al. 2007, Nealy 2007, Matysiak et al. 2006]. Two essential attributes of this electronic sensor give it single-molecule sensitivity. The first is the very localized (nanoscale) geometry of charge sensitivity in the pore itself. The diameter of a pore might be 2-3 nm, and due to electrolyte charge screening the measured current is highly insensitive to charge sources more than a few nanometers from the pore. Second, the nanopore sensor provides a gain through the effect the comparatively slow-moving charge a biopolymer has on a nearby concentration of higher-mobility salt ions. Nanopores, however, are extremely limited by the relatively short time biomolecules spend in the charge-sensitive region of the pore. This is directly addressed by the use of tags, which can be optimized to produce high signal levels and longer translocation events. At the same time, CMOS co-integration of these pores is exploited to dramatically improve the noise-limited bandwidths for detection in a nanopore device. Both solid-state and biological pores are supported by this platform. This solid-state integration, along with associated microfluidics, also uniquely enables the scale-up of this design to large arrays with integrated electronics for detection.

Example 1

I. Design and Synthesis of Modified Nucleotides

Figure 4:
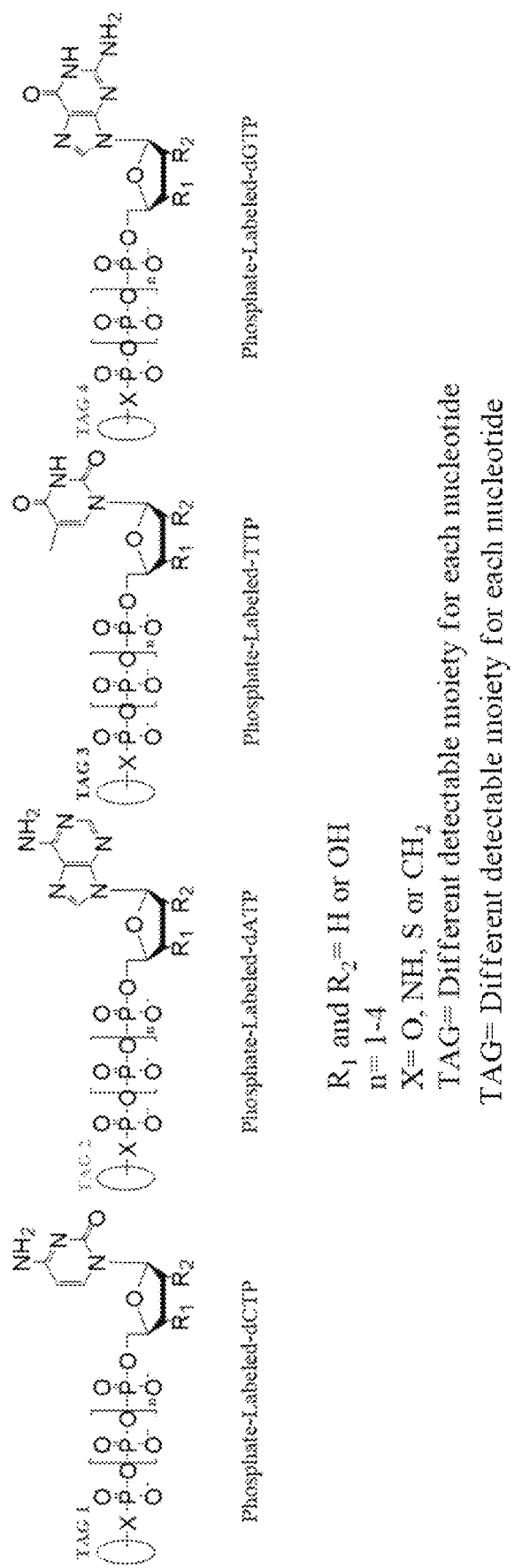
FIG. 4. Structure of four phosphate-tagged nucleoside-5'-polyphosphates.

Effect of bulkiness of the tagged-polyphosphate on electronic blockade signals generated by a nanopore is determined using various phosphate-linked-nucleotides with different size tags or groups attached to the terminal phosphate of the nucleotide. Structures of four phosphate-tagged nucleoside-5'-polyphosphates are shown in FIG. 4. First, a series of nucleoside-5'-tri-, tetra-, penta-, and hexa-phosphates is synthesized. In these nucleotides, the terminal phosphate is attached with a linker through which different tags, e.g. different length and mass ethylene glycols or other molecules which increases the bulkiness or charge of the released polyphosphate, are attached. These nucleotides are tested with nanopore to determine which tags or bulky groups attached to the terminal phosphate correlate to more dramatic difference in electronic blockade signal between the different bases.

Figure 5:
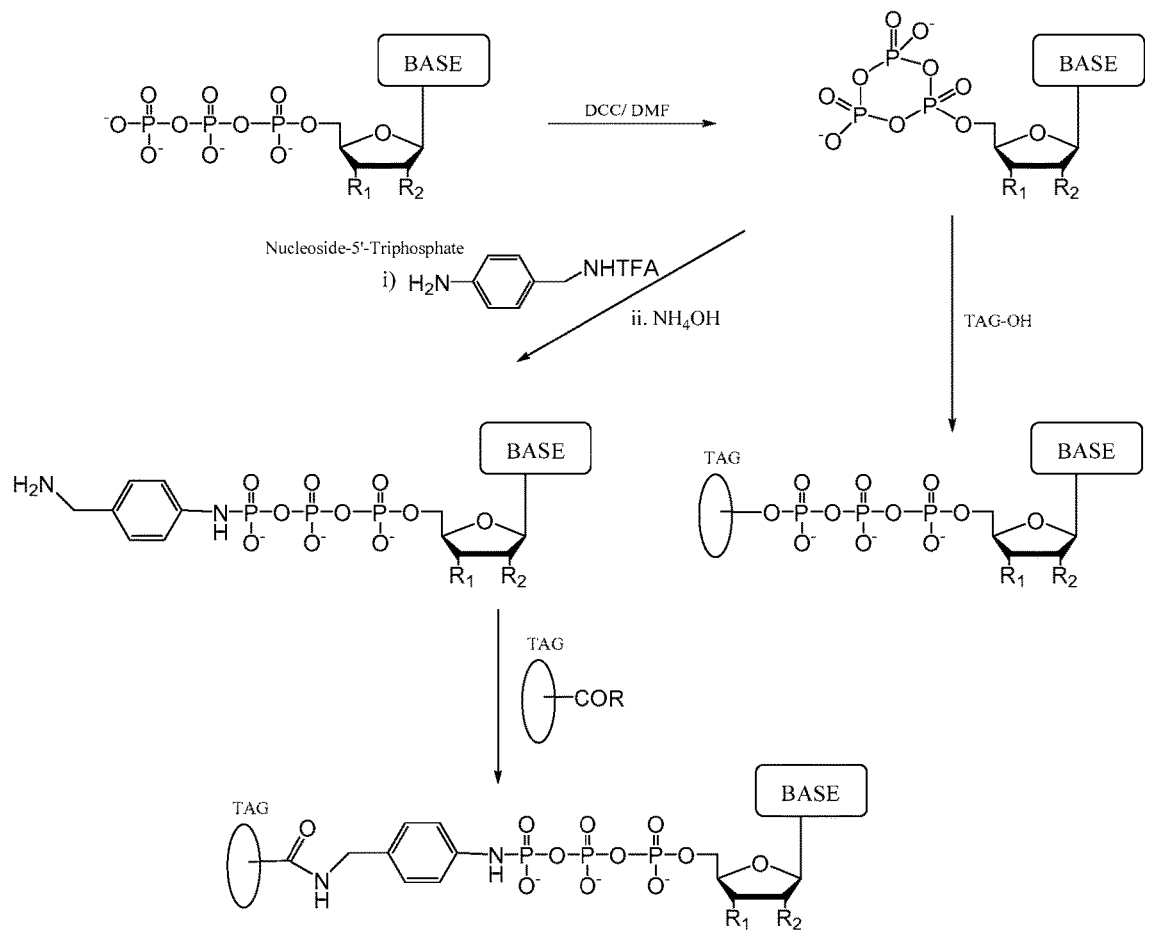
FIG. 5. Synthesis of phosphate-tagged nucleoside-5'-triphosphates.

1) Terminal Phosphate-Modified Nucleoside-Polyphosphates a. Terminal Phosphate-Tagged Nucleoside-5'-triphosphates As shown in FIG. 5, terminal phosphate tagged-nucleoside-5'-triphosphates can be synthesized by reacting the corresponding dNTP with DCC/DMF to give cyclic trimetaphosphate which can be opened with appropriate nucleophiles to give tag or linker attached nucleoside-5'-triphosphate. This can be used in a template-primer extension reaction and the released tag-attached pyrophosphate can be read using nanopore. Alternatively, the linker attached to the phosphate can be reacted with tag-NHS ester to provide alternate tag-attached nucleoside-5'-triphosphate.

b. Terminal Phosphate-Tagged Nucleoside-5'-tetraphosphates

Figure 6:
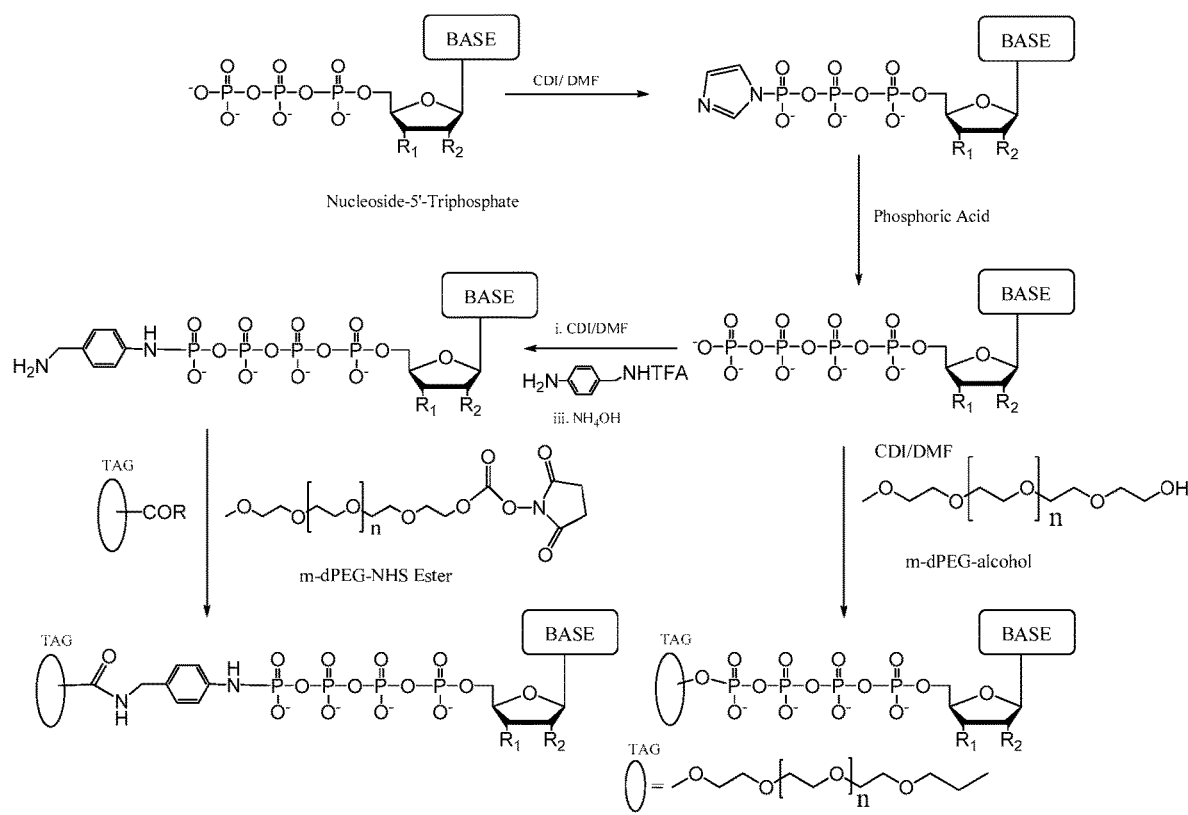
FIG. 6. Synthesis of phosphate-tagged nucleoside-5'-tetraphosphates.

For the synthesis of terminal phosphate tagged nucleoside-5'-tetraphosphates, the corresponding triphosphate is first reacted with CDI in DMF to activate the terminal phosphate group which is then reacted with phosphoric acid or tag-monophosphate to give the tetraphosphate (FIG. 6). The terminal phosphate on the tetraphosphate can be further activated with CDI followed by reaction with appropriate nucleophiles to provide a linker attached tetraphosphate which can further be used to attach tags of different mass, length or bulk, such as m-dPEG-NHS ester, also shown in FIG. 6.

c. Terminal Phosphate-Tagged Nucleoside-5'-penta- and hexaphosphates

Figure 7:
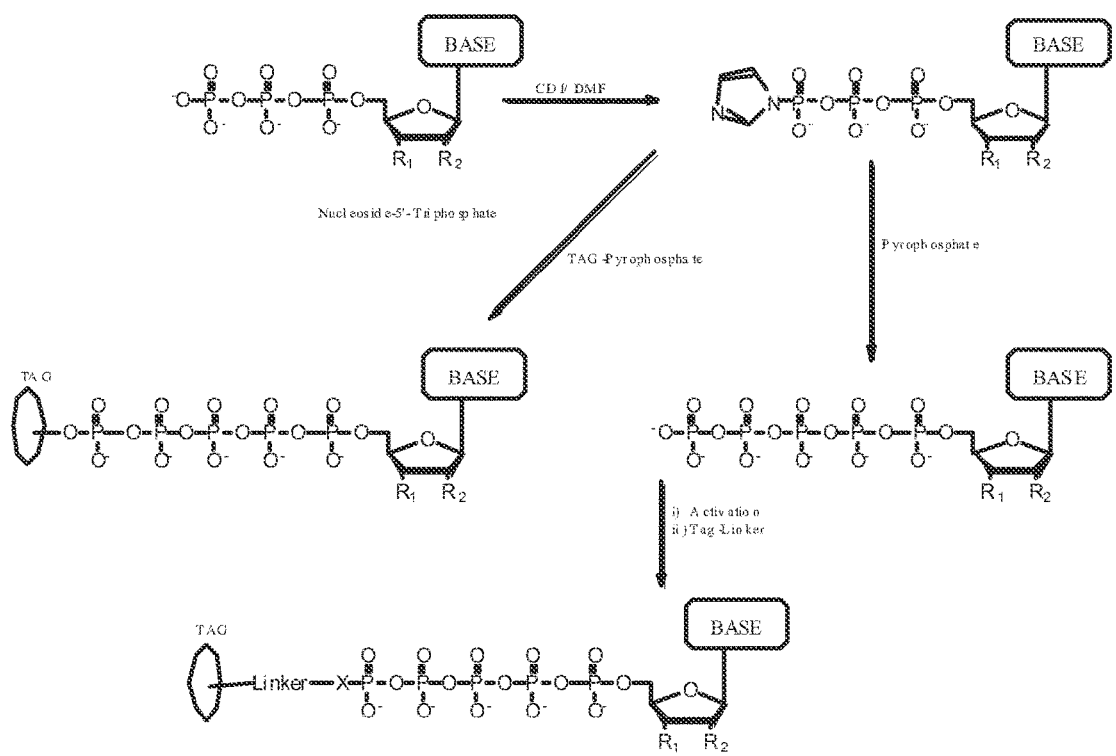
FIG. 7. Synthesis of terminal phosphate-tagged nucleoside-5'-pentaphosphates.

Synthesis of terminal phosphate tagged nucleoside-5'-penta- and hexaphosphates follows the same principle as shown in FIG. 7. They can be prepared either from activated triphosphates or the tetraphosphates by reacting with phosphoric acid, pyrophosphate or tag-attached phosphates. Alternatively, a linker can be attached to penta- or hexaphosphate followed by reaction with activated NHS esters.

d. Oligo-Tag Attached Nucleoside-Polyphosphates

There are a number of issues with current approach to nanopore sequencing such as recognition of the bases as they pass through the nanopore and the speed or rate of transport to allow recognition of the nucleobase be registered. DNA passes through a α-hemolysin nanopore at a rate of 1-5 µs, which is too fast to record for single molecule sequencing experiments. Some progress has been made to overcome these issues by a variety of protein engineering strategies including the use of molecular brakes (short covalently attached oligonucleotides) [Bayley, H. 2006].

Figure 8:
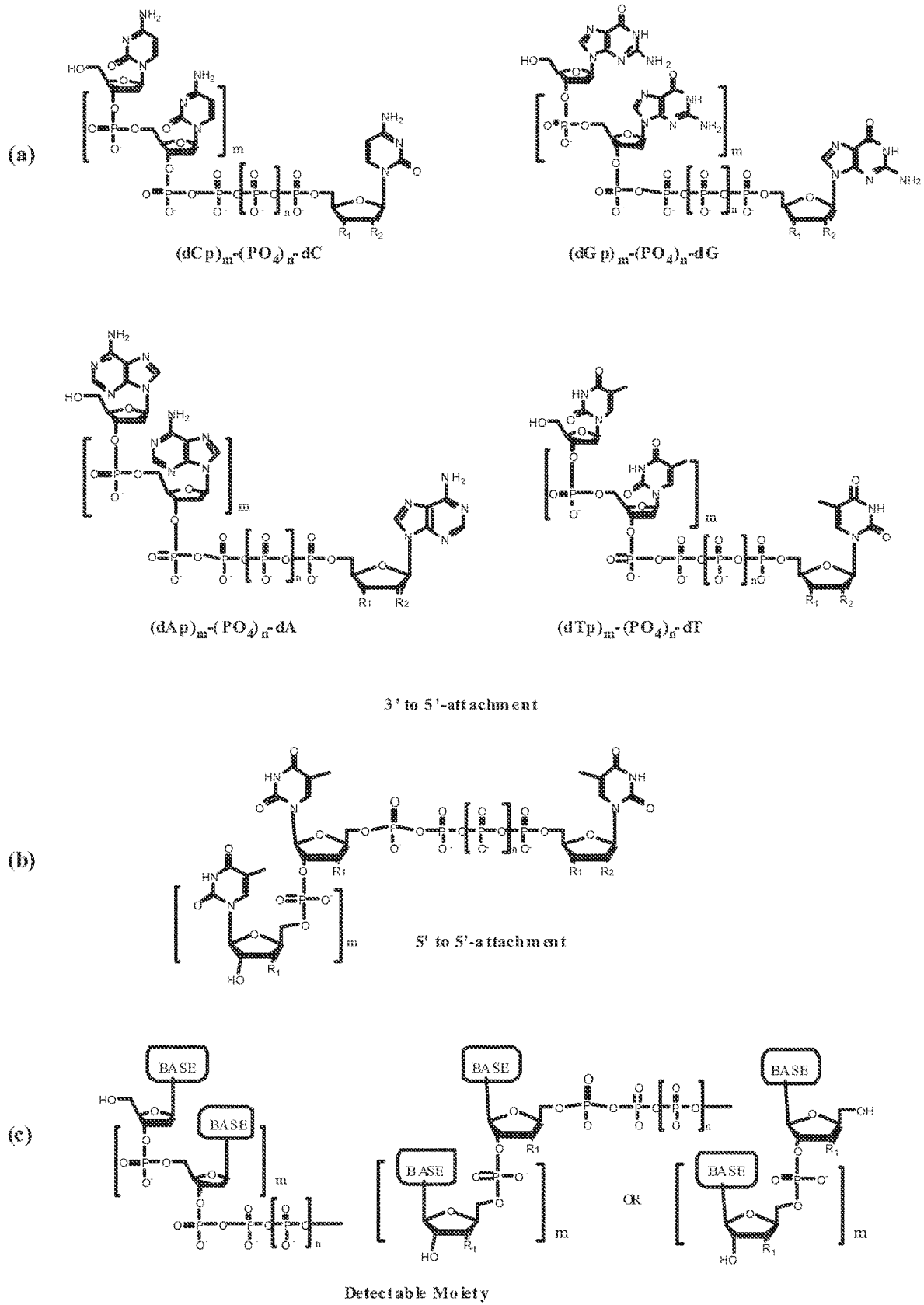
FIG. 8. a) oligo-3' to 5'-phosphate attachment, b) oligo-5' to 5'-phosphate attachment, c) detectable moiety after polymerase reaction.

As disclosed herein, short oligonucleotides can be attached to the terminal-phosphate of a nucleoside polyphosphate by reaction of the activated terminal phosphate with the 3'-OH or the 5'-OH of the oligonucleotide. Alternatively, the 3'- or 5'-phosphate of the oligonucleotide can be activated with CDI or Imidazole/DCC and reacted with nucleoside-5'-polyphosphates. Structures of oligo-attached nucleoside phosphates (oligo-3' to 5'-phosphate; oligo-5' to 5'-phosphate) are shown in FIGS. 8(a) and 8(b), respectively. The polymerase reaction by-product which is monitored by passing through the nanopore is shown in FIG. 8(c).

The rate of migration through the nanopore of the polymerase reaction by-product can be controlled by attaching oligonucleotides of different length to different nucleoside-5'-polyphosphates. For example, if nucleoside dA has 1 or 2 oligo-dA units attached, dT may have 3 oligo-dT units, dC may have 4 oligo-dC units, and dG may have 5 oligo-dG units. Different combinations of the number of oligos for each nucleotide could be used to control the transport and retention time in a nanopore.

The transport and retention time in a nanopore also can be controlled by adding different number of phosphate groups to the nucleotides. Thus the charge and mass can vary for each nucleotide polyphosphate.

Examples of Linker Tag Structure

Specific examples of reactive groups on the terminal phosphates or the nucleoside base moiety and groups with which groups can react are provided in Table 1. The reactive groups with which they can react can be present either on the linker or on the tag.

TABLE 1

Possible Reactive Substituents and Functional Groups Reactive Therewith

| Reactive Groups | Functional Groups |
| --- | --- |
| Succinimidyl esters | Primary amino, secondary amino |
| Anhydrides, acid halides | Amino and Hydroxyl groups |
| Carboxyl | Amino, Hydroxy, Thiols |
| Aldehyde, Isothiocyanate & Isocyanates | Amino groups |
| Vinyl sulphone & Dichlorotriazine | Amino groups |
| Haloacetamides | Thiols, Imidazoles |
| Maleimides | Thiols, Hydroxy, Amino |
| Thiols | Thiols, Maleimide, Haloacetamide |
| Phosphoramidites, Activated P. | Hydroxy, Amino, Thiol groups |
| Azido | Alkyne |

Tags which can be detected by nanopore are included herewith but by no means are they limited to these group of compounds. One skilled in the art may change the functional group(s) to come up with a suitable tag.

The tags include aliphatic, aromatic, aryl, heteroaryl compounds with one or more 4-8 membered rings and may optionally be substituted with halo, hydroxy, amino, nitro, alkoxy, cyano, alkyl, aryl, heteroaryl, acid, aldehyde, Azido, alkenyl, alkynyl, or other groups. These includes, polyethylene glycols (PEGs), carbohydrates, aminoacids, peptides, fluorescent, fluorogenic (non-fluorescent but become fluorescent after removal of protecting group) chromogenic (colorless but become colored after removal of protecting group) dyes, chemiluminiscent compounds, nucleosides, nucleoside-mono, di or polyphosphates, oligonucleotides, aryl, heteroaryl or aliphatic compounds. Some examples are given in FIG. 16.

Structure of PEG-phosphate-labeled nucleotides and some examples of possible PEGs with different reactive groups to react with functional groups are exemplified in FIG. 17.

Some other examples of the dyes or compounds which can be used to attach to the terminal phosphate or the base moiety of the nucleotides are provided here. By no means, these are the only compounds which can be used. These are listed here as examples and one skilled in the art can easily come up with a suitable linker-tag which can be attached to the nucleotide and detected by nanopore.

Other examples of suitable tags are:
Fluorescent dyes: Xanthine dyes, Bodipy dyes, Cyanine dyes Chemiluminiscent compounds: 1,2-dioxetane compounds (Tropix Inc., Bedford, Mass.). Amino acids & Peptides: naturally occurring or modified aminoacids and polymers thereof. Carbohydrates: glucose, fructose, galactose, mannose, etc. NMPs & NDPs: nucleoside-monophosphates, nucleoside-diphosphates. Aliphatic or aromatic acids, alcohols, thiols, substituted with halogens, cyano, nitro, alkyl, alkenyl, alkynyl, azido or other such groups.

2) Base-Modified Nucleoside-5'-triphosphates

A variety of nucleotide reversible terminators (NRTs) for DNA sequencing by synthesis (SBS) are synthesized wherein a cleavable linker attaches a fluorescent dye to the nucleotide base and the 3'-OH of the nucleotide is blocked with a small reversible terminating group [Ju et al. 2006, Guo et al. 2008 & 2010]. Using these NRTs, DNA synthesis is reversibly stopped at each position. After recording the fluorescent signal from the incorporated base, the cleavable moieties of the incorporated nucleotides are removed and the cycle is repeated.

Figure 9A:
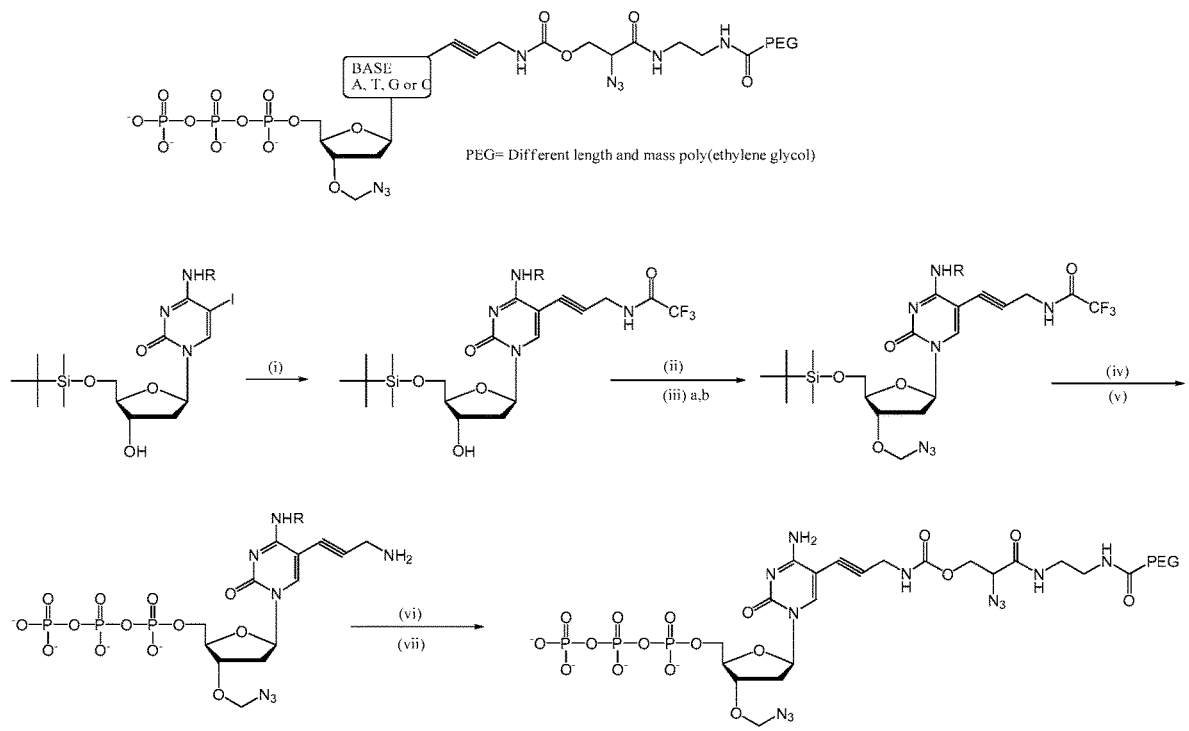
FIG. 9(A). Synthesis of base-modified nucleoside-5'-triphosphates.

The same type of nucleotides can also be used for nanopore DNA sequencing. As shown in FIG. 9(A), a small blocking group at 3'-OH and a tag-attached at the base linked through a cleavable linker can be synthesized. After polymerase extension reaction, both the 3'-O-blocking group and the tag from the base are cleaved and the released tag can be used to pass through the nanopore and the blockage signal monitored. Four different tags (e.g. different length and molecular weight poly-ethylenene glycols (PEGs), as shown in FIG. 9(A)) can be used, one for each of the four bases, thus differentiating the blockage signals.

Figure 9B:
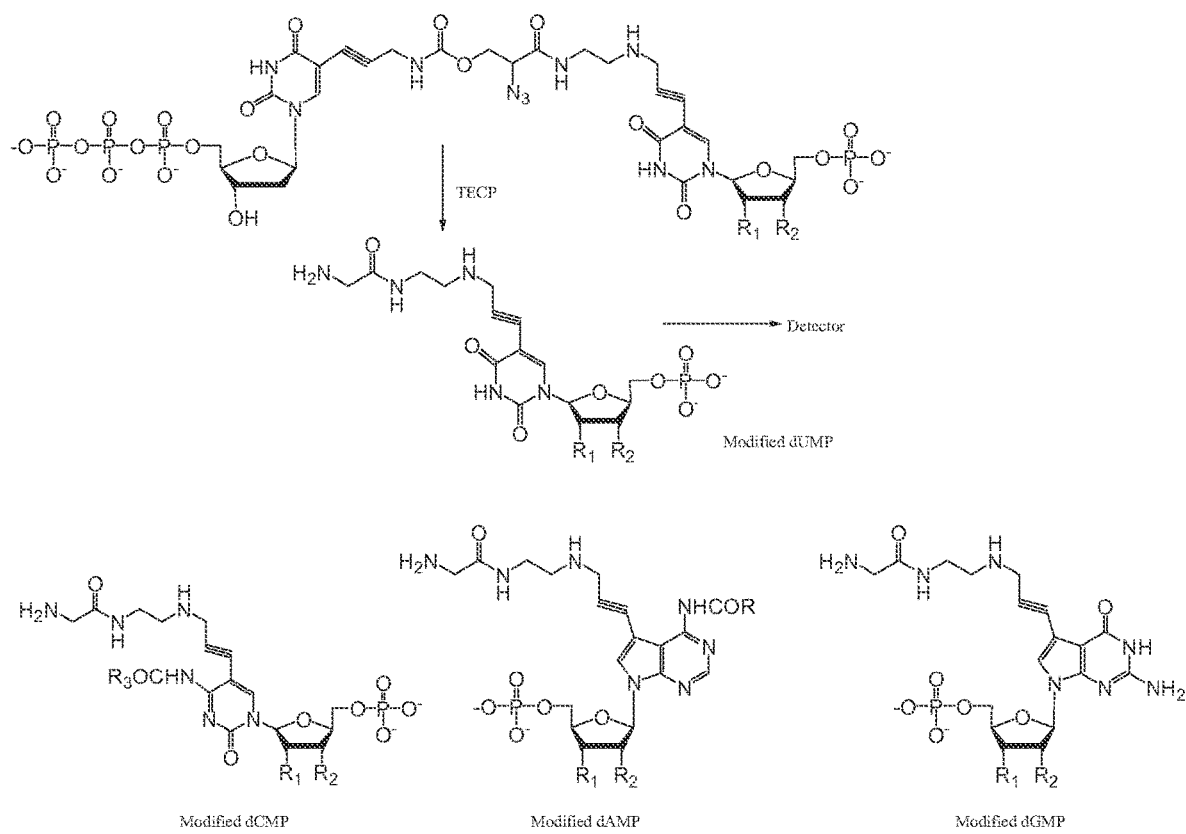
FIG. 9(B). Cleavage of base-modified nucleoside-5'-triphosphate and cleavage with TCEP.

Alternatively, the 3'-O-blocking group is not used because it has been shown that a bulky group or nucleotide base can prevent the DNA polymerase from adding more than one nucleotide at a time [Harris et al. 2008]. As shown in FIG. 9(B), a bulky dNMP is introduced through a cleavable linker. Thus, different dNMPs are introduced through a linker according to the original dNTP. For example, with dTTP nucleotide, a dTMP is introduced (for dATP, a dAMP; for dGTP, a dGMP and for dCTP, a dCMP is introduced). After polymerase incorporation and cleavage with TCEP, modified dNMPs are generated which are passed through the nanopore channel and detected by appropriate methods.

3) 2'- or 3'-OH Modified Nucleoside-5'-triphosphates

Figure 10:
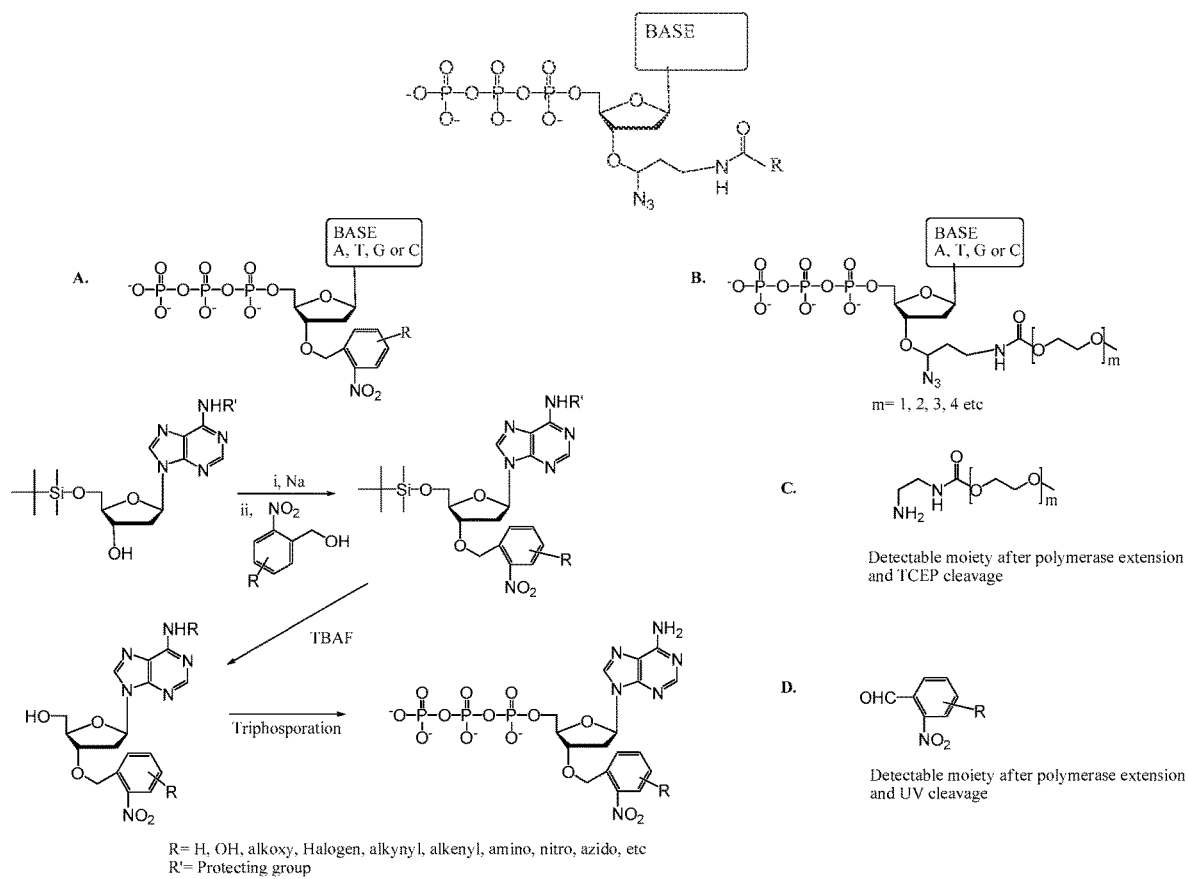
FIG. 10. Synthesis of 3'-O-modified nucleoside-5'-triphosphates. A. 3'-O-2-nitrobenzyl attached dNTPs; B. 3'-O-azidomethyl attached dNTPs; C. Detectable moiety after polymerase extension and TCEP cleavage; and D. Detectable moiety after polymerase extension and UV cleavage.

Synthesis of all four 3'-modified nucleoside-5'-triphosphates can be carried out [Guo et al. 2008, Li et al. 2003, Seo et al. 2004]. 3'-O-2-nitrobenzyl and 3'-O-azidomethyl attached dNTPs (FIGS. 10A and 10B, respectively) are good substrates for DNA polymerases. After incorporation by DNA/RNA polymerase in a sequencing reaction, these 3'-O-tagged nucleotides terminate the synthesis after single base extension because of the blocking group at the 3'-OH. Further extension is possible only after cleavage of the blocking group from the 3'-O position. The 3'-O-2-nitrobenzyl group can be efficiently cleaved by UV light and 2'-O-azidomethyl by treatment with TCEP to generate the free OH group for further extension. The cleaved product from the reaction (FIG. 10C or 10D) is monitored for electronic blockage by passing through the nanopore and recording the signal. Four different substituted nitrobenzyl protected dNTPs and four different azidomethyl substituted dNTPs, one for each of the four bases of DNA, are synthesized.

II. DNA-Extension Using Modified Nucleotides

1) Phosphate-Tagged Nucleotides

Figure 11:
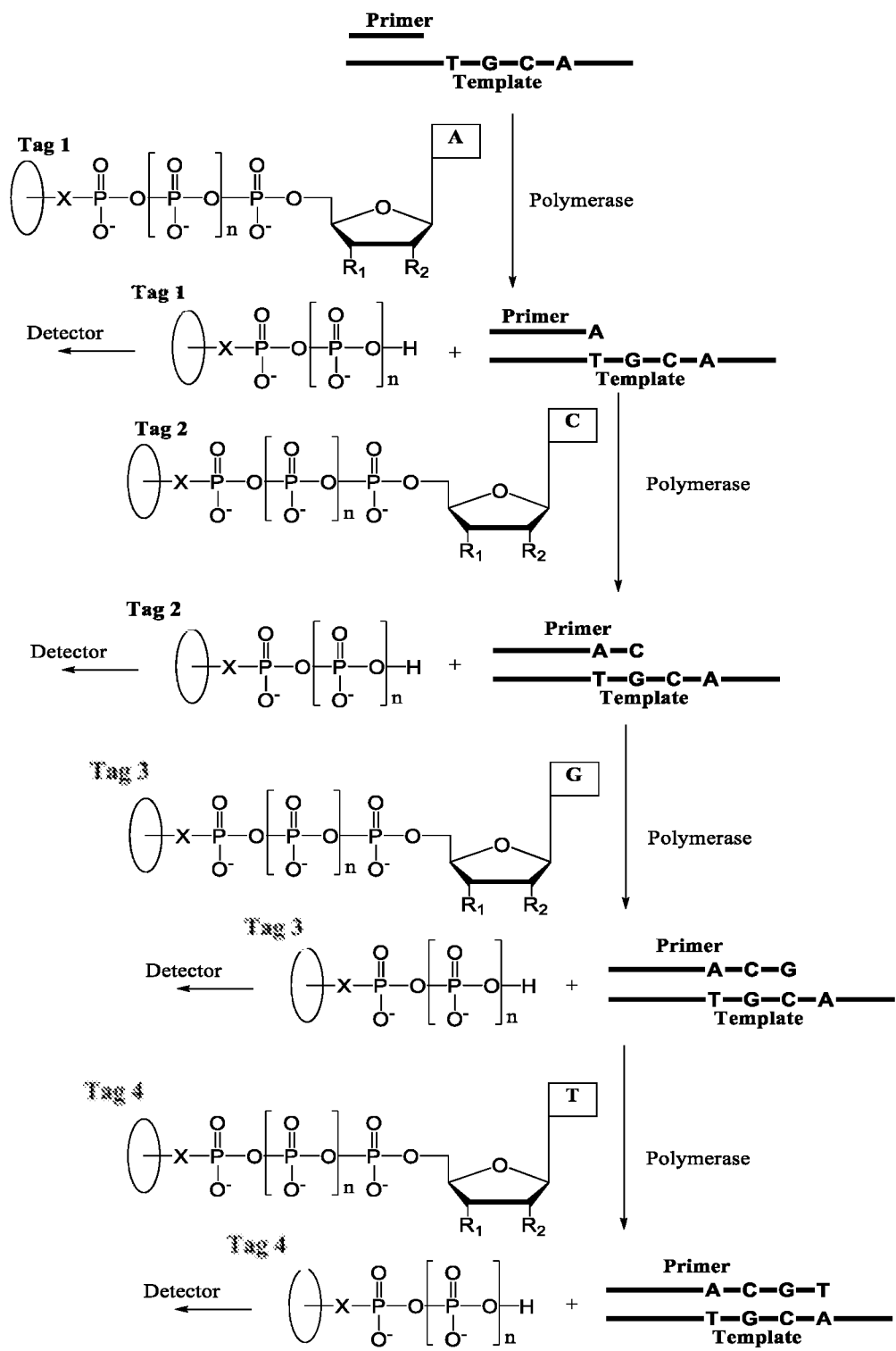
FIG. 11. DNA extension reaction using phosphate modified nucleotide analogues.

Terminal phosphate-tagged nucleoside polyphosphates described above are used in polymerase reactions to generate extension products. As shown in FIG. 11, after a polymerase reaction, the released by-product of the phosphate-tagged nucleotide, tag-polyphosphate, is obtained and the extended DNA is free of any modifications. The released tag-polyphosphate is then used in an engineered nanopore by single-channel recording techniques for sequencing analysis. The released tag-polyphosphates can also be treated with alkaline phosphatase to provide free tags which can also be detected. Using four different tags for the four nucleotides (A, T, G & C) to generate four different tagged-polyphosphates which differ by mass, charge or bulk, the sequence of the DNA can be determined.

2) Base-Tagged Nucleotides with Cleavable Linkers

Figure 12:
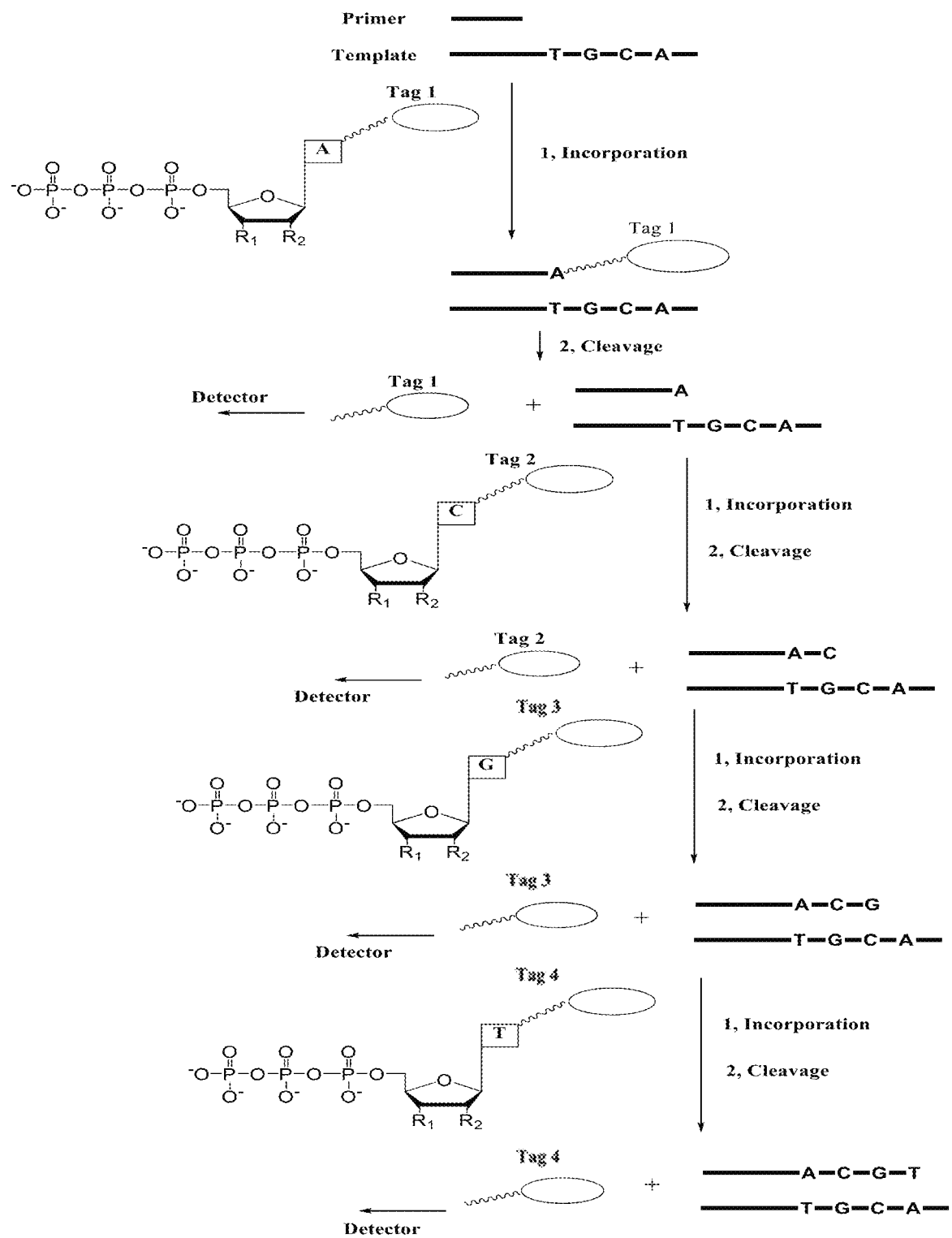
FIG. 12. DNA extension reaction using base-tagged nucleotide analogues.

Base-tagged nucleotide triphosphates for DNA sequencing by synthesis (SBS) and single molecule sequencing are synthesized [Guo et al. 2008 and 2010]. The addition of large bulky groups at the 5-position of pyrimidines (C & T) and 7-position of 7-deazapurines (G & A) can block the addition of more than one nucleotide in a DNA polymerase reaction. Modified nucleotides with a cleavable linker, a bulky group, and different charges attached to the nucleotide base are synthesized. The modified nucleotides may also have a small blocking group at the 3'-OH of the nucleotides. These modified nucleotides are used in a polymerase extension reaction. As shown in FIG. 12, after extension with the appropriate nucleotide, the linker and tag from the nucleotide base and from sugar 3'-O, if blocked, are cleaved by chemical or photochemical means and the released linker-tag is used in an engineered nanopore by single-channel recording techniques for sequencing analysis.

3) 2'- or 3'-Tagged Nucleotides with Cleavable Linkers

Figure 13:
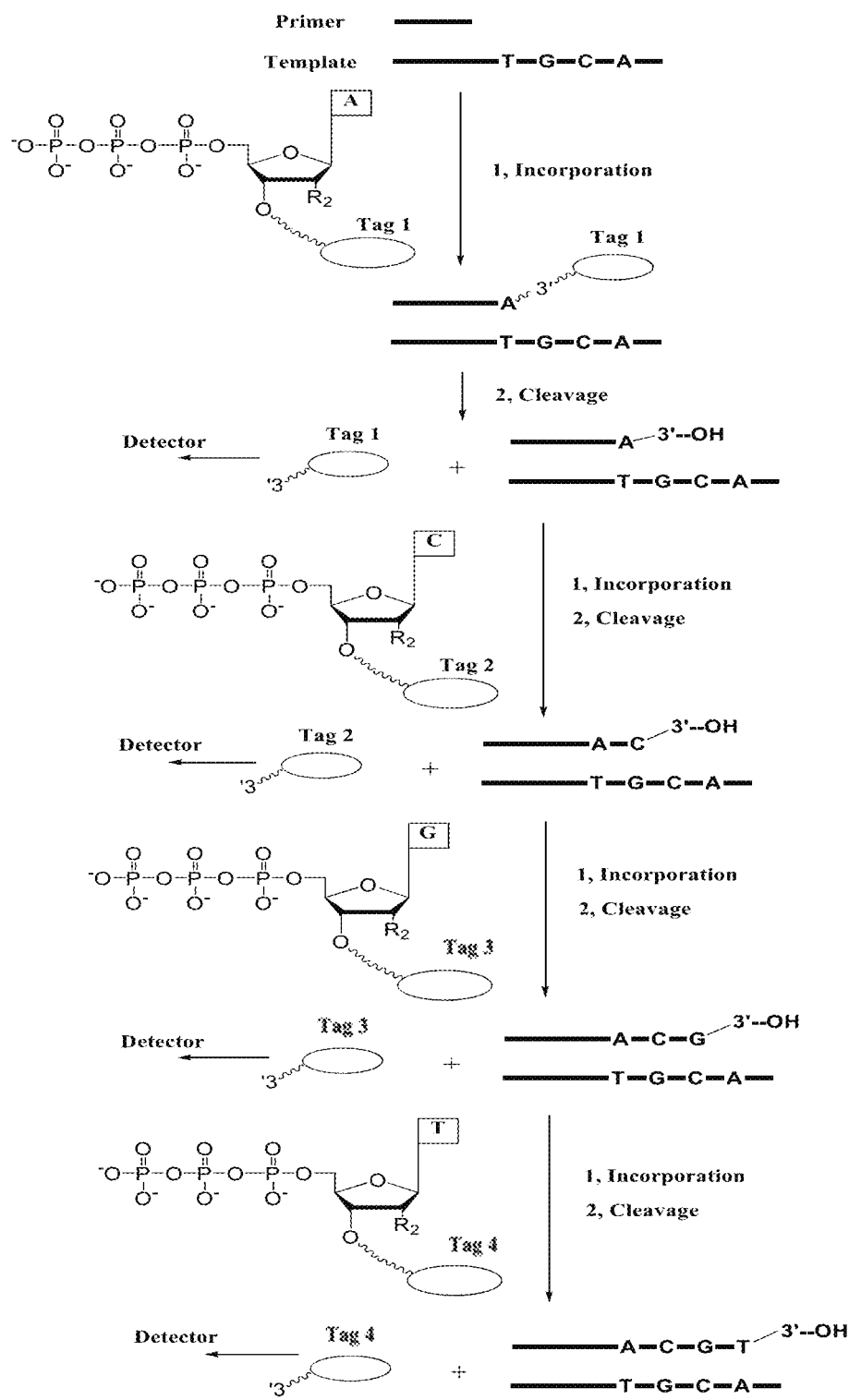
FIG. 13. DNA extension reaction using 2'- or 3'-OH labeled nucleotide analogues.

A linker and tag can also be attached to the 2'- or 3'-OH of nucleotides. After a polymerase extension reaction, the linker-tag is cleaved from the extended product by chemical, photochemical or enzymatic reaction to release the free 3'-OH for further extension. As shown in FIG. 13, the released linker-tag is then used in an engineered nanopore by single-channel recording techniques for sequencing analysis.

III. DNA-Sequencing Study Using Nanopore

Figure 14:
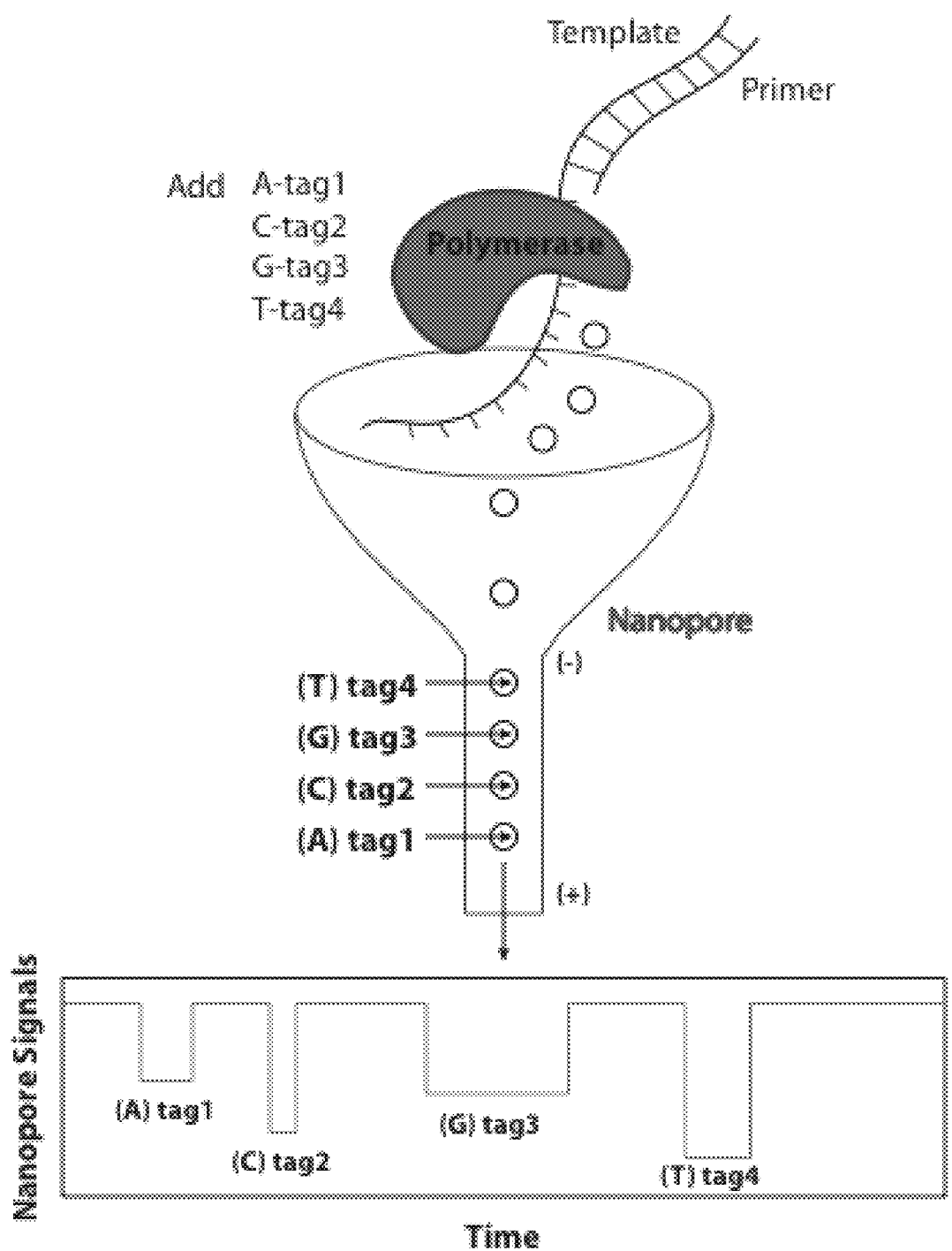
FIG. 14. Schematic of DNA sequencing by nanopore with modified nucleotides, particularly applicable to single molecule real time sequencing involving addition of all 4 nucleotides and polymerase at same time to contact a single template molecule.

Discrimination of different nucleotides in DNA sequencing using nanopore is evaluated following the strategy shown in FIGS. 11-13. To validate a nanopore's ability to distinguish the four different linker-tags in DNA, a series of experiments as shown in FIG. 14 is performed. The DNA/RNA polymerase can be bound to the nanopore and a template to be sequenced is added along with the primer. Either DNA template or primer can also be immobilized on top of the nanopore and then subsequently form a template-primer complex upon addition of a DNA polymerase. To this template-primer complex, four differently tagged nucleotides are added together or sequentially. After polymerase catalyzed incorporation of the correct nucleotide, the added nucleotide releases the tag-attached polyphosphate (in case of terminal-phosphate-labeled nucleotides) which then pass through the nanopore to generate the electric signal to be recorded and used to identify the added base. Optionally, the released tag-polyphosphate can also be treated with alkaline phosphatase to provide free tag which can also be detected by passing through the nanopore. Each tag generates a different electronic blockade signature due to the difference in size, mass or charge. In the case of base-modified or 2'/3'-modified nucleotides, after the DNA/RNA polymerase extension, the tag from the extended primer is cleaved by chemical, photochemical or enzymatic means and the electronic signature of the released tag is monitored. The shape, size, mass, charge or other properties of the tag can be adjusted according to the requirements.

Figure 15:
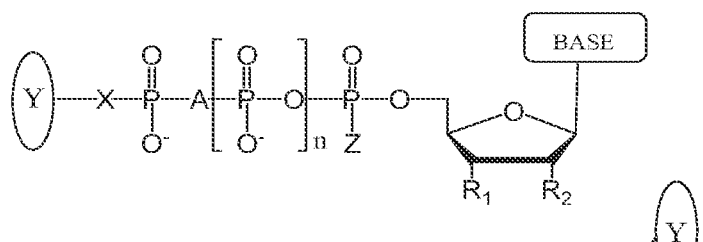
FIG. 15. Phosphate, Base, 2'- and 3'-modified nucleoside phosphates with possible linkers and tags BASE=adenine, guanine, thymine, cytosine, uracil, 5-methyl C, 7-deaza-A, 7-deaza-G or their derivatives thereof.
Figure 15:
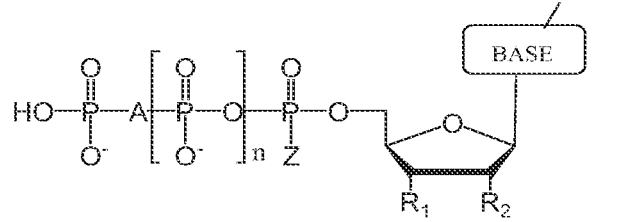
Figure 15:
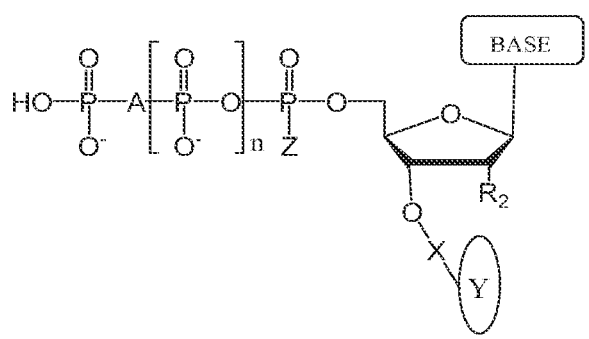
Figure 15:
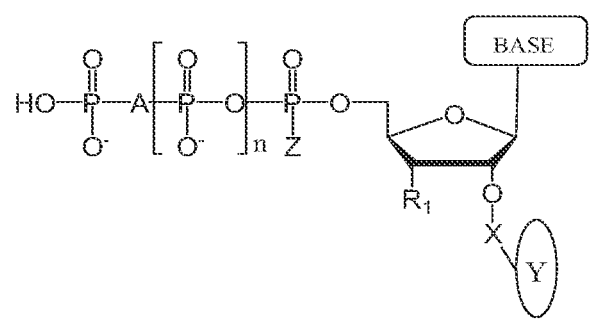

As disclosed herein, signals from each of the nucleotides (FIG. 15) and the transitions between nucleotides of different identities are distinguished and characterized. The magnitude and duration of the blockade signatures on the event diagram are analyzed and compared with known diagrams. Thus, with these rational chemical designs and modifications of the building blocks of DNA, the use of nanopore is optimized to decipher DNA sequence at single molecule level with single base resolution.

To implement this novel strategy for DNA sequencing, an array of nanopores can be constructed on a planar surface to conduct massive parallel DNA sequencing as shown in FIG. 18. The array of nanopores can also be constructed on a silicon chip or other such surfaces. The nanopore can be constructed from the protein with lipid bilayers or other such layers (α-hemolysin pore, *Mycobacterium smegnatis* porin A, MspA) [Derrington et al. 2010] or they can be synthetic solid-state nanopores fabricated in silicon nitride, silicon oxide or metal oxides [Storm et. al. 2005; Wanunu et al. 2008] or a hybrid between a solid-state pore and α-hemolysin [Hall et al. 2010].

FIG. 18 shows a schematic of array of nanopores for massive parallel DNA sequencing by synthesis. The nanopores can sense each DNA/RNA polymerase catalyzed nucleotide addition by-product (Tag-attached to the phosphate or the base and/or 2', 3'-OH of the sugar moiety) as it passes through the nanopore. The electrical properties of different tags will distinguish the bases based on their blockade property in the nanopores. The array of nanopores shown in FIG. 18 can each read the same sequence or different sequence. Increasing the number of times each sequence is read will result in better quality of the resulting sequence data.

Example 2

I. Synthesis of PEG-Labeled-Deoxyguanosine-5'-Tetraphosphates (dG4P-PEG):

PEG-labeled-deoxyguanosine-5'-tetraphosphates (dG4P-PEGs) is synthesized according to FIG. 19. First, 2'-deoxyguanosine triphosphate (dGTP) reacts with CDI in DMF to activate the terminal phosphate group which is then reacted with dibutylammonium phosphate to give the tetraphosphate. The terminal phosphate on this tetraphosphate is further activated with EDAC in 0.1M imidazole buffer followed by reaction with diaminoheptane to provide an amino attached tetraphosphate which is further reacted with mPEG-NHS esters to provide the required four PEG-dG4Ps. After polymerase incorporation, the net charge on the released PEG is –3 (PEG-NH-triphosphate).

II. Testing of Modified Nucleotides in Single Base Extension Reactions.

The dG4P-PEGs are characterized by MALDI-TOF mass spectroscopy as shown in Table II.

TABLE II

MALDI-TOF MS Results for dG4P-PEG

|  | Calculated M.W. | Measured M.W. |
| --- | --- | --- |
| dG4P-PEG24 | 1798 | 1798 |
| dG4P-PEG37 | 2371 | 2374 |

The dG4P-PEGs are excellent substrates for DNA polymerase in primer extension. The MALDI-TOF mass spectra of the DNA extension products are shown in FIG. 20.

Example 3—Single Molecule Detection by Nanopore of the Pegs Used to Label the Nucleotides Poly(ethylene glycol) is a nonelectrolyte polymer that weakly binds cations (e.g., it binds $K^+$ ions at $K_d \sim 2$ M). Thus, the net charge on the polymer depends on the mobile cation concentration and on the presence of other moieties that are chemically linked to it. It has been demonstrated that a single α-hemolysin nanopore can easily distinguish between differently-sized PEG polymers at better than monomer resolution, i.e., better than 44 g/mol [Reiner et al. 2010; Robertson et al. 2007]. That level of discrimination is made possible because the polymer reduces the pore's conductance due to volume exclusion (the pore conductance decreases with increasing polymer size) and by binding mobile cations that would otherwise flow freely through the pore [Reiner et al. 2010]. In addition, the residence time of the polymer in the pore is highly sensitive to the polymer's charge, which for PEG, scales in proportion to the polymer's length. A nanopore should be able to distinguish between differently-sized PEGs that are chemically linked to other moieties. PEGs (PEG 16, 24, 37 and 49) for labeling nucleotides are tested on nanopore and generate distinct electronic blockade signatures at the single molecule level as shown in FIG. 21.

To investigate the effect of bulkiness of the variously tagged polyphosphates on electronic blockade signals generated in the nanopore, various phosphate-linked-nucleotides are synthesized with different size polyethylene glycol (PEG) tags attached to the terminal phosphate of the nucleotide. First, as shown in FIG. 4, we synthesize a series of nucleoside-5'-tri-, tetra-, and penta-phosphates with the terminal phosphate attached via a linker to which different tags, e.g. different length and mass PEGs or other molecules to increase the molecular size or modify the charge of the released polyphosphate, could be attached. We then test these nucleotides in polymerase reactions coupled with detection by nanopore to see which tags or bulky groups attached to the terminal phosphate produce more dramatic differences in electronic blockade signals among different bases.

I. Screen and Select 4 PEG Tags with Distinct Nanopore Blockade Signals

Recently, it has been shown that when a polyethylene glycol (PEG) molecule enters a single α-hemolysin pore, it elicits distinct mass-dependent conductance states with characteristic mean residence times [Robertson et al. 2007]. FIG. 22A shows that the conductance based mass spectrum clearly resolves the repeat units of ethylene glycol, and the residence time increases with the mass of PEG.

I.a Testing PEG for Nanopore Blockade Signatures.

Different length and molecular weight PEGs (commercially available from Quanta Biodesign Ltd or other suppliers) are selected and the nanopore blockade signals monitored, as described in Example 2. As shown in FIG. 22A PEGs of 28-48 ethylene glycol units are clearly distinguished by nanopore. Therefore, PEGs with a broad range of ethylene glycol units displaying very distinct nanopore blockade signals are selected as tags to label the nucleotides A, C, G and T. Examples are shown in FIG. 22B. Branched PEGs as tags are also evaluated as these can be modified with positive charges in a more straightforward fashion. Structures of some linear and branched PEGs are shown at the bottom of FIG. 22.

I.b Design and Synthesis of Phosphate-Labeled PEGs Selected in I.a

In nanopore sequencing, the current blockade signals in the nanopore are generated by the PEG-phosphates released during the polymerase reaction. Thus, we design and synthesize phosphate-labeled PEGs with positively charged linkers, and test these molecules with organic (e.g., α-hemolysin) and synthetic (solid phase) nanopores to evaluate their current blockade signals. The selected PEGs are converted to their triphosphates as shown in FIG. 23. For example, Fmoc-protected amino-butanol can be converted to the corresponding triphosphate by reacting first with phosphorous oxychloride followed by reaction with tributylammonium pyrophosphate in a one pot reaction. The triphosphate after purification is activated with DCC/DMF or CDI/DMF to provide activated triphosphate which reacts with the OH-group of the PEGs to generate PEG-triphosphates. The same scheme is applicable for both linear as well as branched PEGs. These PEG phosphates are tested in nanopores to optimize the conditions for generating distinct current blockade signals.

The polyamino acid (polylysine, polyarginine, interrupted polylysine) linkers are synthesized by standard peptide synthetic strategies; if an ester linkage to the polyphosphate chain is built in, it should be possible to use alkaline phosphatase to cleave it, resulting in more strongly positive tags for nanopore interrogation. Positive charges may also be incorporated into the PEG chains.

I.c Design and Synthesis of a Library of Terminal Phosphate-Tagged Nucleoside-5'-triphosphates.

Terminal phosphate tagged nucleoside-5'-tri-, tetra-, and penta-phosphates are designed and synthesized. These molecules are tested in the polymerase reaction and the optimal ones are selected for nanopore detection. Terminal phosphate-tagged nucleoside-5'-tri-, tetra-, and penta-phosphates with a variety of tags, including small or large polylysines, amino acids, a variety of negatively or positively charged dyes, such as Energy Transfer dyes, and ethylene glycol units, have been shown to be accepted by DNA polymerases as excellent substrates for primer extension [Kumar et al. 2006 and 2008; Sood et al. 2005; and Eid et al. 2009].

I.c.1 Design and Synthesis of Terminal Phosphate-Tagged Nucleoside-5'-triphosphates.

As shown in FIG. 24, terminal phosphate tagged-nucleoside-5'-triphosphates is synthesized by reacting the corresponding dNTP with DCC/DMF to yield a cyclic trimetaphosphate which can be opened with nucleophiles to generate a tag or linker attached nucleoside-5'-triphosphate. In addition, the linker attached to the phosphate can be reacted with PEG-NHS esters to provide alternate PEG-attached nucleoside-5'-triphosphates. The resulting terminal phosphate-tagged nucleoside-5'-triphosphate is used in the template-primer extension reaction and the released tag-attached pyrophosphate is detected and differentiated by its specific nanopore current blockade parameters.

I.c.2 Design and Synthesis of Terminal Phosphate-Tagged Nucleoside-5'-tetraphosphates.

For synthesis of terminal phosphate tagged nucleoside-5'-tetraphosphates, the corresponding triphosphate is first reacted with CDI in DMF to activate the terminal phosphate group which is then reacted with phosphoric acid or tag-monophosphate to give the tetraphosphate as shown in FIG. 25. The terminal phosphate on the tetraphosphate can be further activated with EDAC in 0.1M imidazole buffer followed by reaction with an appropriate nucleophile to provide a linker attached tetraphosphate which can be used to attach tags of different mass, length or charge, such as m-PEG-NHS esters. In this case, four trimethyllysines are used to neutralize the charge of four phosphates. After polymerase incorporation, the net charge on the released PEG is +1 or, if treated with alkaline phosphatase, +4, which can be detected by the nanopore.

I.c.3 Design and Synthesis of Terminal Phosphate-Tagged Nucleoside-5'-Penta-Phosphates.

Synthesis of terminal phosphate tagged nucleoside-5'-penta-phosphates follows the same principle as shown in FIG. 26. They can be prepared either from activated triphosphates or tetraphosphates by reacting with phosphoric acid, pyrophosphate or tag-attached phosphates. Alternatively, a linker can be attached to the pentaphosphate followed by reaction with activated NHS esters.

The terminal phosphate tagged nucleoside polyphosphates described above are used in the polymerase reaction to generate extension products. Following the scheme shown in FIG. 11 the performance of the terminal phosphate tagged nucleoside polyphosphates in polymerase extension are evaluated. We first perform a single base extension reaction and characterize the DNA extension product by MALDI-TOF mass spectroscopy to evaluate incorporation efficiency. After establishing optimized reaction conditions, we immobilize the template on magnetic beads and repeat the single base extension reaction, after which the released polyphosphate-tags are isolated from the solution for detection using a single nanopore. This reaction is performed continuously to evaluate all 4 nucleotides (A, C, G, and T) and their corresponding released tags detected by the nanopore. Continuous polymerase reaction with the polyphosphate-tag nucleotides and the clear distinction of the released polyphosphate-tag by nanopore establish the feasibility of the approach.

As shown in FIG. 11, after the polymerase reaction, the released by-product of the phosphate-tagged nucleotide (tag-polyphosphate) is obtained and the extended DNA strand is free of any modifications. This is advantageous because any scars remaining on growing DNA chains can affect their ability to be recognized by polymerase with increasing nucleotide additions, eventually terminating further DNA synthesis. The released tag-attached polyphosphate are assayed in the nanopore to evaluate sequencing sensitivity and accuracy. In initial experiments we test the tags for their blockade signals before running SBS reactions. DNA sequence can be determined if different tags for the four nucleotides are used to generate four different tagged-polyphosphates which differ by mass, charge or bulk, and yield 4 distinct blockade signals.

II. Detection of the Released Tagged Phosphates by Protein Nanopores

We use a single α-hemolysin nanopore to detect PEGs that are linked to nucleotides attached via a multi-phosphate linker and the same polymer after the nucleotide/ribose moiety has been cleaved by the DNA polymerase reaction. Each of the four different DNA bases is linked to a PEG polymer with a unique length. Thus, each base that is removed from the PEG by the polymerase is identified. Because the unreacted nucleotides cannot be separated from the released tagged polyphosphates, especially in real time situations, we take advantage of the method's extreme sensitivity to molecular charge to discriminate between the released reaction product and the starting material. We measure single α-hemolysin conductance using conical glass supports [White et al., 2006 and 2007] which allow data collection at 100 kHZ and ~4 pA RMS noise. We measure the blockade depth and residence time distributions of both the tagged nucleotides and tagged products over a wide range of transmembrane potentials to determine optimum conditions for nucleotide discrimination and to extend our current theoretical understanding of PEG-nanopore interactions [Robertson et al. 2007] to molecules with fixed charges. Characterization and theoretical understanding permit the unambiguous identification of the nucleotides incorporated into polynucleotides by polymerase. Thus, with these rational chemical designs and modifications of the building blocks of DNA, we optimize the use of nanopores to decipher DNA at the single molecule level with single base resolution in protein or synthetic nanopores.

Example 4—Fabrication of a Single Solid-State Nanopore for Single Molecule Sequencing The transition from a protein nanopore to a solid state nanopore makes the fabrication of high-density nanopore arrays possible, a key step for yielding a high-throughput single molecule electronic DNA sequencer. Here, an integrated single solid state nanopore platform is developed to characterize the tagged nucleotides in the polymerase reaction based on the knowledge gained from the protein nanopore.

Integrated Nanopore Platform.

We developed specialized integrated low-noise CMOS electronics, which when integrated with solid-state nanopores, deliver significant performance advantages over "standard" measurement techniques which employ external electrophysiological amplifiers, such as the Axopatch 200B. These advantages come from exploiting capacitive (rather than resistive) feedback in a custom integrating amplifier design. DC current, which is characteristic of this and other bioelectronic interfaces, is removed with a low-noise current source operating in a DC servo loop. Reduced amplifier input capacitances and reduced parasitic capacitances associated with co-integration improve noise performance at high frequencies, enabling bandwidths approaching 1 MHz for solid-state pores. Such high temporal resolution, when combined with the tags developed, will provide high flexibility for tuning this platform for high sensitivity and real-time performance.

Use of this CMOS-integrated nanopore (CNP) integrated circuit in either a two-chip or one-chip configuration as shown in FIG. 27. In the former case, the pore is packaged together with the CNP as shown in FIG. 27B. In the latter, the pore is fabricated directly into the CNP as shown in FIG. 27C with fluidics on either side of the chip. In both cases, the cis electrode, which connects to the input of the amplifier, is integrated directly on the surface of the CNP. The one-chip configuration has the advantage of being easily scalable to a multiplexed platform at the cost of additional fabrication complexity. The ability to post-process fabricated CMOS dice (which are no more than 5 mm on a side) is a unique capability established over the last five years [Huang et al. 2011, Lei et al. 2008, and Levine et al. 2009]. This approach completely leverages existing foundry process flows rather than requiring new process development.

The one-chip fabrication approach proceeds by adapting standard solid-state nanopore fabrication techniques [Rosenstein et al. 2011]. In areas of the die reserved for the sensors, all metals have been blocked, leaving a thick stack of alternating glass fill and silicon nitride capping layers. The majority of the dielectric stack is etched using an inductively-coupled $CHF_3$ plasma. After depositing and patterning a PECVD $Si_3N_4$ etch mask on the back of the die, localized openings in the silicon substrate are made using an anisotropic potassium hydroxide etch. A short dip in buffered hydrofluoric acid is then used to isolate a single 50 nm layer of silicon nitride from the original dielectric stack as a suspended membrane. Finally, nanopores are drilled through these nitride membranes with a high resolution transmission electron microscope.

The measured noise of this system is shown in FIG. 28A, alongside a measurement of the baseline noise for a comparable configuration of the Axopatch 200B. For the highest bandwidth supported by the Axopatch (B=100 kHz), the integrated amplifier has a noise floor of 3.2 $pA_{RMS}$, compared to 9 $pA_{RMS}$ for the Axopatch. At the highest bandwidth characterized for the integrated amplifier (B=1 MHz), the noise level is 27 $pA_{RMS}$, in contrast with 247 $pA_{RMS}$ modeled by extrapolating the Axopatch response beyond its supported range (approximately a factor-of-ten lower noise). As a point of comparison, for a 1 nA signal, only about 6250 ions are transported through the pore in 1 us. An input-referred noise level of 27$pAV_{RMS}$ for integrated amplifier allows resolution of as few as 150 ions in this interval.

It is also important to note this superior electrical performance is obtained with an integrated amplifier that consumes an area of only 0.2 $mm^2$ on a CMOS chip compared with a rack-mounted Axopatch amplifier, demonstrating the significance of the innovative electronics. When a nanopore is connected to the amplifier input, the introduction of 1/f noise and membrane capacitance raises the noise spectrum above the open-headstage baseline. FIG. 28b shows a typical noise spectrum in this case, demonstrating noise floors of only 10 $pA_{RMS}$ and 163 $pA_{RMS}$ for bandwidths of 100 kHz and 1 MHz, respectively. Measured comparisons are shown with the Axopatch up to 100 kHz for the same nanopore. At 100 kHz, there is more than a factor-of-two reduction in input-referred noise power for the CNP. If the Axopatch could be measured at higher bandwidths, there would be a factor-of-six noise power difference at 1 MHz.

This platform also allows the integration of biological nanopores, providing even more flexibility. Biological nanopores are created in lipid membranes (typically 1, 2-dioleoyl-sn-glycero-3-phosphocholine (DOPC)) formed over a hole in a teflon membrane between two fluid cells. The surface must be sufficiently hydrophilic for the membrane to form from unilamellar vesicles. The conductance between the two chambers of the cell is monitored while the membrane protein is added to one of the cells, which is immediately flushed once incorporation is detected. The membranes used to fabricate the nanopores can also be used as solid supports for lipid bilayers with the drilling of larger holes into the membranes, over which the lipid bilayer is formed [Clarke et al. 2009; Benner et al., 2007; Hou et al., 2009; and Wang et al. 2011]. Planar bilayer lipid membranes (BLMs) have been engineered with different protein channels on patterned solid supports with nanopatterned holes (~100 nm in diameter), as well as tethering them directly on gold through a self-assembled monolayer assembly [Axelrod et al., 1976, Bultmann et al. 1991, Dutta et al. 2010, Jenkins et al. 2001, Nam et al. 2006, Palegrosdemange et al. 1991, Shen et al. 2009, Srinivasan et al. 2001, Yang et al. 2003, Yin et al. 2005]. Moreover, it has been shown that formation of contiguous BLMs with a diffusion coefficient of 4 $\mu m^2/s$ on nanopatterned substrates; BLMs formed on SAM-gold assemblies yielded a coefficient of 0.8 $\mu m^2/s$. Both fall within the ideal diffusion range of 0.1-10 $\mu m^2/s$ representative of well-formed BLMs [Axelrod et al. 1976, Bultmann et al. 1991]. Electrical characterizations of these BLMs indicate a high impedance membrane with a 1.4GW-mm² resistance, making it amenable for further electrical analysis of biological nanopores formed in the membrane [Oliver et al. 1994, Shi et al. 2000, Wiehelman 1988].

Immobilization of Polymerase to Nanopore-Bearing Surfaces

The size of the polymerase is about 5 nm×5 nm. One polymerase is positioned near the entrance to each nanopore. To accomplish this for the solid-state nanopores, it is necessary that (1) a unique position on the surface be modified with functional groups during CMOS fabrication to bind the polymerase; (2) that the sites be small enough that only one polymerase molecule can bind; (3) that they be far enough apart that there is little possibility of diffusion of the released tagged polyphosphates to a nearby channel; and (4) that the cross-linking agent be sufficiently flexible that the enzyme is functionally intact. Polymerase tethering is accomplished by combining a patterned attachment point with the use of an appropriate concentration of polymerase solution during incubation such that at most one enzyme molecule is attached.

Establishment of the appropriate tether point for the polymerase is accomplished by exploiting existing fabrication approaches for solid-state nanopores. Typically, to maximize the transduction signals, these pores are created by thinning a supported $Si_3N_4$ membrane using e-beam lithography to define a window which is subsequently thinned with a plasma etch (e. g. $SF_6$). The nanopore is then drilled in the thinned region using e-beam ablation. The well created by this window (FIG. 29) creates a natural place to tether the polymerase, guaranteeing close proximity to the nanopore entrance. Prior to etching the thinned window, the original membrane can be augmented with a buried epitaxial layer of attachment material. Once the window is etched, this can become a selective sidewall region for polymerase attachment. Attachment materials include silicon dioxide or gold. There may be limited selectivity with silicon dioxide, however, because an oxide can also form on the silicon nitride surface under appropriate conditions.

In principle, with silicon dioxide surfaces, biotin-streptavidin linkages can be used [Korlach et al. 2008 and 2010], utilizing biotinylated PEG molecules on the silica patches and incubate biotin-end labeled polymerase in the presence of streptavidin. The remainder of the surface is passivated with polyvinylphosphonic acid. Due to the concerns raised above, it is preferable instead to modify the gold surface with an alkanethiol self-assembled monolayer (SAM) functionalized with amino groups [Love et al. 2005]. These can be easily modified to NHS esters for attachment to amino groups on the polymerase. The thickness and homogeneity of the layer is determined by ellipsometry or atomic force microscopy.

Development of 5'-Modified Nucleotides with Positively Charged Linkers

A system for rapid diffusion of the released tags toward the pores while the precursor nucleotides and DNA are repelled by the pores is generated. The tagged nucleotides are engineered so that after incorporation into the DNA, the tag released from the nucleoside has a cumulative positive charge while the intact tag-nucleotides remain neutral. This allows actively gating the released tag specifically through the detection channel, if the channel is negatively charged according to known methods [Wanunu et al. 2007]. As all other free molecules present in the reaction mix (primers, unreacted nucleotides, template), other than the tag, are negatively charged, only the released tag carrying positive charge is attracted into the channel, increasing the specificity of detection and reducing noise. A different number of charged groups can be used on different tags, depending on the specific nucleotide base. Thus the cumulative charge of the tag along with its size can be used for base discrimination. After incorporation and release of the tag, if the polyphosphate is deemed to mask the positive charge, it can be removed using secondary reactions (for example, alkaline phosphatase immobilized at a second downstream site in the pore). The positively charged tag can be gated into the negatively charged channel for detection and recognition.

Diffusion and Drift

A critical aspect of this sequencing system is the reliable and timely capture of each nucleotide's released tag by the adjacent nanopore. Conditions must be engineered such that tags are captured quickly and in the correct order. Additionally, the capture rate of unincorporated tags should be minimized, and interference from adjacent channels should be negligible. Creating the well at the entrance of the pore (as shown in FIG. 29) assists this process, which also depends on close proximity of the polymerase to the nanopore opening. Analysis of nanopore capture processes generally considers a radially symmetric process surrounding the pore. Geometry dictates that in the absence of an electric field, a molecule tends to diffuse farther from a pore, opposing the electrostatic attraction. With a voltage gradient, there exists a critical distance L at which molecular motion due to diffusion and electrophoresis are equal [Gershow et al. 2007]. This critical distance is a function of the ionic current (I) and electrolyte conductivity ($\sigma$), as well as the diffusion constant (D) and mobility ($\mu$) of the analyte molecule, $$L = \frac{|I|}{2\pi\sigma}\frac{\mu}{D}.$$

Capture is a statistical process, but approximately 50% of molecules at a distance L is captured. This likelihood increases for shorter distances, and exceeds 90% for d<L/3. During this process, molecules typically are captured in a timescale on the order of $$t_{capture} = \frac{L^2}{2D}.$$

By placing the polymerase within L/3 of the nanopore, nearly all molecules are captured. It also ensures that $t_{capture}$ is significantly faster than the polymerase incorporation rate, to capture bases in the correct order.

An approximate value for the diffusion coefficient of 25-unit PEG molecules in water is D=3e−10 m²/s [Shimada et al. 2005], which is on the same order of magnitude as a similar-length ssDNA fragment [Nkodo et al. 2001]. Assuming validity of the Nernst-Einstein relation (although this does not always hold true for polymers), the mobility can be estimated as a function of the diffusion constant and net charge (Q), $$\mu \approx \frac{QD}{k_B T}.$$

For these estimates, then, with I=5nA in 1M KCl—see the following Table.

|  | +1e | +4e |
|---|---|---|
| 50% capture | 2.1 nm | 5.8 nm |
| 90% capture | 0.7 nm | 1.9 nm |
| $t_{capture}$ | 7.1 ns | 114 ns |

Example 5—Fabricate an Array of Solid-State Nanopores

In addition to improved performance, only with the integrated electronics is it possible to produce massively parallel nanopore arrays. This involves the one-chip topology shown in FIG. 27C in which nanopores are integrated directly into the CMOS die with fluidics on either side of the chip. The approach for integrating multiple pores is also shown in FIG. 27C. In this case, wells of SU-8 photoresist are used to isolate individual nanopores from each other. This is an approach similar to that of Rothberg et al. 2011. In Rothberg et al., however, the wells can still remain "connected" by the solution reservoir above the chip. In present case, since electrical isolation is necessary between the cis reservoirs, a PDMS cap is used to seal the wells for measurement after the introduction of reagents as shown in FIG. 27C. 64 solid-state nanopores are integrated onto the same 5-mm-by-5-mm die. The current integrating amplifier design, which would have to be duplicated at each pore site, is only 250 um by 150 um, but additional space has to be left for the fabrication of the pore itself. As fabrication techniques are further developed to reduce the chip area, this can be easily scaled to an array of 16-by-16 electrodes.

Example 6—Pyrosequencing Using Phosphate-Tagged Nucleotide and Nanopore Detection Pyrosequencing is sequencing by synthesis (SBS) method which relies on the detection of pyrophosphate that is released when a nucleotide is incorporated into the growing DNA strand in the polymerase reaction [Ronaghi et al. 1998]. In this approach, each of the four dNTPs is added sequentially with a cocktail of enzymes, substrates, and the usual polymerase reaction components. If the added nucleotide is complementary to the first available base on the template, the nucleotide will be incorporated and a pyrophosphate will be released. Through an enzyme cascade, the released pyrophosphate is converted to ATP, and then turned into a visible light signal by firefly luciferase. On the other hand, if the added nucleotide is not incorporated, no light will be produced and the nucleotide will simply be degraded by the enzyme apyrase. Pyrosequencing has been applied successfully to single nucleotide polymorphism (SNP) detection and DNA sequencing. A commercial sequencing platform was developed combining pyrosequencing and DNA template amplification on individual microbeads for high-throughput DNA sequencing [Margulies et al. 2005]. However, there are inherent difficulties in pyrosequencing for determining the number of incorporated nucleotides in homopolymeric regions (e.g. a string of several T's in a row) of the template. Beside this, there are other aspects of pyrosequencing that still need improvement. For example, each of the four nucleotides has to be added and detected separately. The accumulation of undegraded nucleotides and other components could also lower the accuracy of the method when sequencing a long DNA template.

This is a modified pyrosequencing approach which relies on the detection of released tag- or tag-phosphates during polymerase reaction. In this approach, phosphate-tagged nucleotides are used in polymerase catalyzed reaction on a template-primer complex. Upon incorporation of the tagged-nucleotides, the phosphate-tag moiety is released, which can be detected by passing through a nanopore. The same tag can be used on each nucleotide or a different molecular weight and length tag (such as PEGs) can be used. It has been shown that polyethylene glycols (PEGs) of different length and mass can be resolved at single-molecule sensitivity when passed through hemolysin nanopore [Robertson et al. 2009].

An α-hemolysin channel could be used to detect nucleic acids at the single molecule level [Kasianowicz et al. 1996]. The monomeric polypeptide self-assembles in a lipid bilayer to form a heptameric pore, with a 1.5 nm-diameter limiting aperture. In an aqueous ionic salt solution, the pore formed by the α-hemolysin channel conducts a strong and steady ionic current when an appropriate voltage is applied across the membrane. The limiting aperture of the nanopore allows linear single-stranded but not double-stranded nucleic acid molecules (diameter ~2.0 nm) to pass through. The polyanionic nucleic acids are driven through the pore by the applied electric field, which blocks or reduces the ionic current. This passage generates a unique electronic signature. Thus a specific event diagram, which is the plot of translocation time versus blockade current, will be obtained and used to distinguish the length and the composition of polynucleotides by single-channel recording techniques based on characteristic parameters such as translocation current, translocation duration, and their corresponding dispersion in the diagram. Four PEG tags, which have been shown to yield distinct current blockade signals in nanopores, are selected to couple with four nucleotides (A, C, G, T) at the terminal phosphate. These novel nucleotide analogs are used in a polymerase reaction and use nanopores to detect the released tags for decoding the incorporated bases as shown in FIG. 14.

There are several advantages to this approach:
1) Avoid the use of many different enzymes (saves cost and complexity).
2) Addition of single tag-attached nucleoside polyphosphate sequentially or all four nucleotides with different tags attached to each nucleotide.
3) Use of PEGs as tags which can be detected by nanopore at a single unit resolution.
4) Real time Single molecule detection sequencing as the tag passes through the nanopore.
5) Massively parallel sequencing, low cost and high throughput.

As shown in FIG. 14, DNA polymerase is immobilized to the nanopore and the template-primer along with the PEG-tagged nucleotides is added. On incorporation of the correct PEG-tagged nucleotide, the released PEG-phosphates pass through the nanopore and the electronic blockade signal is measured. Different length PEGs have different blockade signals, thus, 4 different PEGs can be used for 4 different nucleotides.

The nucleotides can be added one at a time, if the correct nucleotide is added it gives a distinct blockade signal. However, if the nucleotide is not complementary to the template nucleic acid base, it will not be incorporated and thus no signal detected. In a massive parallel way high density array of micro/nano wells to perform the biochemical process can be constructed. Each micro/nano-well holds a different DNA template and nanopore device. The released PEGs are detected at single-molecule sensitivity.

General methods for synthesis of TAG-labeled-nucleoside-5'-polyphosphate is shown in FIG. 30. Terminal-phosphate-labeled-nucleoside-5'-tri, tetra-, penta-, or hexa-phosphates can be synthesized starting from the corresponding nucleoside-5'-triphosphates (NTP). Thus, triphosphate is first activated with DCC/DMF which can be directly reacted with the TAG-nucleophile to give TAG-attached-NTP or it can be reacted with a linker nucleophile to which a TAG-NHS or appropriately activated TAG can be reacted to provide TAG-linker-attached NTP. For the synthesis of TAG-attached nucleoside tetraphosphates (N4P) or pentaphosphates (N5P), the activated triphosphate is first reacted with phosphoric acid or pyrophosphate to give tetra- and penta-phosphate, respectively, which can be reacted with linker nucleophile followed by the reaction with appropriate activated TAGs.

Synthesis of PEG-labeled nucleotides are discussed above in Examples 2 and 3. The PEG-labeled nucleotides have -3, -4, -5, or -6 charges based on the use of tri, tetra-, penta-, or hexa-phosphates. After polymerase catalyzed primer-extension reaction, the net charge on the released PEG-tags will be one less (−1) than the starting PEG-nucleotide which is enough to distinguish by the nanopore ionic blockade signal (unreacted PEG-nucleotide is also bulkier than the released PEG-phosphates, thus different ionic blockade signal). Alternatively, if alkaline phosphatase is present in the reaction mixture, the released PEG will be neutral (the free phosphate groups are hydrolyzed by alkaline phosphatase). The released PEG-tags can also be made positively charged as shown below so that they can be easily detected by nanopores. Similarly, they can also be made highly negatively charge.

Synthesis of Positively Charged TAG-Attached-Nucleoside-Polyphosphates:

The positively charged TAG-attached nucleoside-polyphosphates are synthesized as shown in FIG. 25. First, a positively charged trimethyl-(lysine)$_n$-glycine amino acid (K[(Me)$_3$]$_n$-Gly) is reacted with the PEG-NHS ester and then activated to form the PEG-K[(Me)$_3$]$_n$-Gly-NHS ester. This activated ester is reacted with the amino-terminated nucleoside-polyphosphate as shown in FIGS. 19 and 25. The net charge on the nucleoside-tetraphosphate is neutral but after polymerase incorporation, the released PEG has a +1 positive charge and if alkaline phosphatase is added to the reaction cocktail, the net charge on the released PEG is +4. Thus the released TAG can be easily separated and identified by passing through the nanopore.

Synthesis of 3'-Blocked-PEG-Attached-Nucleoside-Polyphosphates for Sequencing by Synthesis with Nanopore Detection.

The synthesis of 3'-blocked-nucleoside-polyphosphates essentially follows the same route as shown for TAG-attached nucleoside-polyphosphates, except that the starting nucleoside-5'-triphosphate is 3'-O-blocked-dNTP. As shown in FIG. 31, 3'-O-azidomethyl-dNTP (6) is first reacted with CDI or DCC/DMF followed by reaction with phosphoric acid (tetraphosphate) or pyrophosphate (pentaphosphates). This is reacted after purification with the appropriate nucleophile to provide amino-terminated phosphate which is then reacted with the appropriate PEG-NHS ester (neutral, positively charged or negatively charged) to provide required 3'-O-blockade-PEG-attached-nucleoside-polyphosphate.

Sequencing Scheme with PEG-Nucleotides and Nanopore Detection (many copies of a DNA molecule are immobilized on a bead and sequential addition of one PEG-nucleotide at a time).

As shown in FIG. 32, the DNA molecules are immobilized on a bead. Thus each bead has many copies of the same DNA molecule. The bead is added to a micro/nano-well which is attached to a nanopore. The DNA forms the complex with the DNA polymerase which is either attached to the nanopore or added to the micro/nano well along with the PEG-attached nucleotide. The nucleotides can be added one at a time, if the correct nucleotide is added it is incorporated and release a PEG-Tag which gives a distinct blockade signal when passed through a nanopore. However, if the nucleotide is not complementary to the template nucleic acid base, it will not be incorporated and thus no signal detected. In this case, the same length and molecular weight PEG can be used on all four nucleotides, or, if desired, four different PEGs can also be used. Thus, addition of nucleic acid base can be easily detected by the nanopore blockade signal at single-molecule sensitivity.

Sequencing by Synthesis with 3'-O-Blocked-PEG-Nucleotides and Nanopore Detection (many copies of a DNA molecule are immobilized on a bead and simultaneous addition of all four 3'-O-blocked-PEG-nucleotides).

The homopolymeric regions of the DNA can be corrected sequenced using this approach. Thus, if the 3'-OH group of the nucleotide is blocked by a reversible moiety, the DNA synthesis will stop after addition of only one nucleotide. The synthesis can be continued after the removal of the blocking group to generate a free 3'-OH group. As shown in FIG. 33 all four different size PEG-attached-3'-O-azidomethyl-nucleotides can be added to the reaction micro/nano-well and whenever a correct nucleotide is incorporated, the released PEG-tag is read by passing through the nanopore and ionic signal detected. Because 3'-OH group is blocked only one nucleotide is added at one time. This 3'-O-blocked group can be cleaved by TECP treatment and thus free OH group is ready for further nucleotide incorporation. By repeated nucleotide addition and cleavage, homopolymeric region can be correctly and easily sequenced.

Massively Parallel Pyrosequencing Using Nanopores:

As shown in FIG. 34, in a massive parallel way high density array of micro wells to perform the biochemical process can be constructed. Each micro/nano-well holds a different DNA template and nanopore device. The released PEGs are detected at single-molecule sensitivity.

Summary of Experiment

1) Any TAG of different size, length, molecular weight, charge attached to the terminal phosphate of the nucleotide which can be detected by nanopore after polymerase incorporation.
2) TAG attached to the tri-, tetra-, penta-, hexa-phosphates.
3) Electronic Detection
4) Group of DNA molecules attached to the bead or solid surface and single-molecule detection sensitivity (High density and high sensitivity).
5) Easily sequenced homopolymeric region by using TAG-attached-3'-O-blocked nucleotides.
6) Add one TAG-nucleotide per cycle.
7) Add all four reversibly tagged-nucleotides together for sequencing homopolymeric regions.

8) High sensitivity, accuracy and speed.
9) Massive parallel sequencing.

REFERENCES

1. Akeson, M., Branton, D., Kasianowicz, J. J., Brandin, E. and Deamer, D. W. Microsecond time-scale discrimination between polycytidylic acid and polyadenylic acid segments within single RNA molecules. *Biophys. J.* 1999, 77, 3227-3233.
2. Aksimentiev, A. et al., Microscopic Kinetics of DNA Translocation through Synthetic Nanopores. *Biophysical Journal* 2004 87, 2086-2097.
3. Astier, Y., Braha, O. & Bayley, H. Toward single molecule DNA sequencing: direct identification of ribonucleoside and deoxyribonucleoside 5'-monophosphates by using an engineered protein nanopore equipped with a molecular adapter. *J Am Chem Soc* 128, 1705-10 (2006).
4. Axelrod, D., Koppel, D. E., Schlessinger, J., Elson, E. & Webb, W. W. Mobility measurement by analysis of fluorescence photobleaching recovery kinetics. *Biophysical Journal* 16, 1055-1069 (1976).
5. Bailey, H. Sequencing single molecules of DNA. *Curr. Opinion Chem Biol.* 2006, 10, 628-637.
6. Benner, S. et al. Sequence-specific detection of individual DNA polymerase complexes in real time using a nanopore. *Nat Nanotechnol* 2, 718-24 (2007).
7. Bezrukov, S. M., and Kasianowicz, J. J. Neutral polymers in the nanopore of alamethicin and alpha-hemolysin. *Biologicheskie Membrany* 2001, 18, 453-457.
8. Bokhari, S. H. and Sauer, J. R., A Parallel Graph Decomposition Algorithm for DNA Sequencing with Nanopores. *Bioinformatics* 2005 21(7), 889-896.
9. Branton, D. Nanopore sequencing. *Nat. Biotechnol.* 26, 1146-1153 (2008).
10. Branton, D. et al. The potential and challenges of nanopore sequencing. *Nat Biotechnol* 26, 1146-53 (2008).
11. Bultmann, T., Vaz, W. L., Melo, E. C., Sisk, R. B. & Thompson, T. E. Fluid-phase connectivity and translational diffusion in a eutectic, two-component, two-phase phosphatidylcholine bilayer. *Biochemistry* 30, 5573-9 (1991).
12. Chandler, E. L., Smith, A. L., Burden, L. M., Kasianowicz and Burden, D. L. Membrane Surface Dynamics of DNA-Threaded Nanopores Revealed by Simultaneous Single-Molecule Optical and Ensemble Electrical Recording. *Langmuir* 2004, 20, 898-905.
13. Chen, P. Probing single DNA molecule transport using fabricated nanopores. *Nano Lett.* 4, 2293-2298 (2004).
14. Clarke, J., Wu, H., Jayasinghe, L., Patel, A., Reid, S. and Bayley, H. Continuous base identification for single-molecule nanopore DNA sequencing. *Nat. Biotech.* 2009, 1-6.
15. Cockroft, S. L., Chu, J., Amorin, M. & Ghadiri, M. R. A single-molecule nanopore device detects DNA polymerase activity with single-nucleotide resolution. *J Am Chem Soc* 130, 818-20 (2008).
16. Deamer, D. W. and Branton, D. Characterization of nucleic acids by nanopore analysis. *Acc. Chem. Res.* 2002, 35(10), 817-825.
17. Deamer, D. W. Nanopore Analysis of Nucleic Acids Bound to Exonucleases and Polymerases, *Annual Review of Biophysics*, Vol. 39: 79-90 (Volume publication date June 2010).
18. Derrington, I. M. et al. Nanopore DNA sequencing with MspA. *Proc Natl Acad Sci USA* 107, 16060-5 (2010).
19. Dutta, D., Pulsipher, A. & Yousaf, M. N. Selective Tethering of Ligands and Proteins to a Microfluidically Patterned Electroactive Fluid Lipid Bilayer Array. *Langmuir* 26, 9835-9841 (2010).
20. Eid, J., Fehr, A., Gray, J., Luong, K., Lyle, J., Otto, G. et al. Real-time DNA sequencing from single polymerase molecules. *Science* 2009, 323, 133-138.
21. Fologea, D. et al., Slowing DNA Translocation in a Solid State Nanopore. *Nano Letters* 2005 5(9), 1734-1737.
22. Fologea, D. et al., Detecting Single Stranded DNA with a Solid State Nanopore. *Nano Letters* 2005 5(10), 1905-1909.
23. Garaj, S. et al. Graphene as a subnanometre trans-electrode membrane. *Nature* 467, 190-3 (2010).
24. Gershow, M. & Golovchenko, J. A. Recapturing and trapping single molecules with a solid state nanopore. *Nature Nanotechnology* 2, 775-779 (2007).
25. Guo, J; Xu, N., Li, Z., Zhang, S.; Wu, J., Kim, D. H., Marma, M. S., Meng, Q., Cao, H., Li, X., Shi, S., Yu, L., Kalachikov, S., Russo, J. J., Turro, N. J., Ju, J. Four-color DNA sequencing with 3'-O-modified nucleotide reversible terminators and chemically cleavable fluorescent dideoxynucleotides. *Proc. Natl. Acad. Sci. USA* 2008, 105(27), 9145-9150
26. Guo, J., Yu, L., Turro, N. J., and Ju, J. An integrated system for DNA sequencing by synthesis using novel nucleotide analogues. *Accounts of Chemical Research* 2010, 43(4), 551-563.
27. Hall, A. R. et al. Hybrid pore formation by directed insertion of alpha-haemolysin into solid-state nanopores. *Nat Nanotechnol* 5, 874-7 (2010).
28. Harris, T. D., Buzby, P. J. et al. Single-molecule DNA sequencing of a viral genome. *Science* 2008, 320, 106-109.
29. Healy, K. Nanopore-based single-molecule DNA analysis. *Nanomedicine (Lond)* 2, 459-81 (2007).
30. Heng, J. B. et al., Stretching DNA Using the Electric Field in a Synthetic Nanopore. *Nano Letters* 2005 5(10), 1883-1888.
31. Heng, J. B. et al., The Electromechanics of DNA in a synthetic Nanopore. *Biophysical Journal* 2006, 90, 1098-1106.
32. Henrickson, S. E., Misakian, M., Robertson, B. and Kasianowicz, J. J. Driven asymmetric DNA transport in a nanometer-scale pore. *Physical Review Letters* 2000, 85, 3057-3060.
33. Hou, X. et al. A biomimetic potassium responsive nanochannel: G-quadruplex DNA conformational switching in a synthetic nanopore. *J Am Chem Soc* 131, 7800-5 (2009).
34. Huang, T. C. et al. Gene expression analysis with an integrated CMOS microarray by time-resolved fluorescence detection. *Biosens Bioelectron* 26, 2660-5 (2011).
35. Hurt, N., Wang, H., Akeson, M. & Lieberman, K. R. Specific nucleotide binding and rebinding to individual DNA polymerase complexes captured on a nanopore. *J Am Chem Soc* 131, 3772-8 (2009).
36. Jenkins, A. T. A., Neumann, T. & Offenhausser, A. Surface plasmon microscopy measurements of lipid vesicle adsorption on a micropatterned self-assembled monolayer. *Langmuir* 17, 265-267 (2001).
37. Ju, J., Kim, D. H., Bi, L., Meng, Q., Bi, X., Li, Z., Li, X., Marma, M. S., Shundi, S., Wu, J., Edwards, J. R., Romu, A., and Turro, N. J. Four-color DNA sequencing by synthesis using cleavable fluorescent nucleotide reversible terminators. *Proc. Natl. Acad. Sci. USA* 2006, 103(52), 19635-19640

38. Kasianowicz, J. J., Brandin, E., Branton, D. and Deamer, D. W. Characterization of individual polynucleotide molecules using a membrane channel. *Proc. Natl. Acad. Sci. USA* 1996, 93, 13770-13773.

39. Kasianowicz, J. J. Nanometer-scale pores: potential applications for DNA characterization and analyte detection. *Disease Markers* 2003, 18, 185-191.

40. Kasianowicz, J. J. Nanopore. Flossing with DNA. *Nature Materials* 2004, 3, 355-356.

41. Korlach, J. et al. Selective aluminum passivation for targeted immobilization of single DNA polymerase molecules in zero-mode waveguide nanostructures. *Proc Natl Acad Sci USA* 105, 1176-81 (2008).

42. Korlach, J. et al. Real-time DNA sequencing from single polymerase molecules. *Methods Enzymol* 472, 431-55 (2010).

43. Kumar, S, and Sood, A. Labeled Nucleoside Polyphosphates. US Patent 2006, U.S. Pat. No. 7,041,812

44. Kumar, S., McDougall, M., Sood, A., Nelson, J., Fuller, C., Macklin, J. and Mitsis, P. Terminal-Phosphate-Labeled Nucleotides with New Linkers. US Patent 2008, U.S. Pat. No. 7,393,640

45. Kumar, S., Sood, A., Wegener, J., Finn, P., Nampalli, S., Nelson, J., Sekher, A., Mitsis, P., Macklin, J. and Fuller, C. W. Terminal Phosphate Labeled Nucleotides: Synthesis, Applications and Linker effect on incorporation by DNA Polymerases. *Nucleosides, Nucleotides &Nucleic Acids* (2005) 24 (5-7), 401-408

46. Lee S. E., Sidorov A., Gourlain T., Mignet N., Thorpe S. J., Brazier J. A., Dickman M. J., Hornby D. P., Grasby, J. A. and Williams, D. M. Enhancing the catalytic repertoire of nucleic acids: a systematic study of linker length and rigidity. *Nucleic Acids Research* 2001, 29(7), 1565-1573.

47. Lei, N., Watson, B. O., MacLean, J. N., Yuste, R. & Shepard, K. L. A 256-by-56 CMOS Microelectrode Array for Extracellular Neural Stimulation of Acute Brain Slices. in *Solid-State Circuits Conference, 2008. ISSCC 2008. Digest of Technical Papers. IEEE International* 148-603 (2008).

48. Levine, P. M., Gong, P., Levicky, R. & Shepard, K. L. Real-time, multiplexed electrochemical DNA detection using an active complementary metal-oxide-semiconductor biosensor array with integrated sensor electronics. *Biosens Bioelectron* 24, 1995-2001 (2009).

49. Li, Z., Bai, X., Ruparel, H., Kim, S., Turro, N.J. and Ju, J. A photocleavable fluorescent nucleotide for DNA sequencing and analysis. *Proc. Natl. Acad. Sci. USA* 2003, 100, 414-419.

50. Love, J. C., Estroff, L. A., Kriebel, J. K., Nuzzo, R. G. & Whitesides, G. M. Self-assembled monolayers of thiolates on metals as a form of nanotechnology. *Chem Rev* 105, 1103-69 (2005).

51. Margulies, M. et al. Genome Sequencing in Open Microfabricated High Density Picoliter Reactors. *Nature* 437: 376-380 (2005).

52. Mathe, J. et al., Nanopore Unzipping of Individual Hairpin Molecules. *Biophysical Journal* 2004 87, 3205-3212.

53. Matysiak, S., Montesi, A., Pasquali, M., Kolomeisky, A. B. & Clementi, C. Dynamics of polymer translocation through nanopores: theory meets experiment. *Phys Rev Lett* 96, 118103 (2006).

54. McNally, B. et al. Optical recognition of converted DNA nucleotides for single-molecule DNA sequencing using nanopore arrays. *Nano Lett* 10, 2237-44 (2010).

55. Meller, A., Nivon, L., Brandin, E., Golovchenko, J. and Branton, D. Rapid nanopore discrimination between single polynucleotide molecules. *Proc. Natl. Acad. Sci. USA* 2000, 97, 1079-1084.

56. Meller, A. et al., Single Molecule Measurements of DNA Transport Through a Nanopore. *Electrophoresis* 2002 23, 2583-2591.

57. Merchant, C. A. et al. DNA translocation through graphene nanopores. *Nano Lett* 10, 2915-21 (2010).

58. Nam, J. M., Nair, P. M., Neve, R. M., Gray, J. W. & Groves, J. T. A fluid membrane-based soluble ligand-display system for live-cell assays. *Chem Bio Chem* 7, 436-440 (2006).

59. Nkodo, A. E. et al. Diffusion coefficient of DNA molecules during free solution electrophoresis. *ELECTROPHORESIS* 22, 2424-2432 (2001).

60. Oliver, A. E. & Deamer, D. W. Alpha-Helical Hydrophobic Polypeptides Form Proton-Selective Channels in Lipid Bilayers. *Biophysical Journal* 66, 1364-1379 (1994).

61. Palegrosdemange, C., Simon, E. S., Prime, K. L. & Whitesides, G. M. Formation of Self-Assembled Monolayers by Chemisorption of Derivatives of Oligo(Ethylene Glycol) of Structure Hs(Ch2)11(Och2ch2)Meta-Oh on Gold. *Journal of the American Chemical Society* 113, 12-20 (1991).

62. Perkins, T. T., Quake, S. R., Smith, D. E. and Chu, S. Relaxation of a single DNA molecule observed by optical microscopy. *Science* 1994, 264, 822-826.

63. Reiner, J. E., Kasianowicz, J. J., Nablo, B. J. & Robertson, J. W. Theory for polymer analysis using nanopore-based single-molecule mass spectrometry. *Proc Natl Acad Sci USA* 107, 12080-5 (2010).

64. Rief, M., Clausen-Schaumann, H. and Gaub, H. E. Sequence-dependent mechanics of single DNA molecules. *Nat. Struct. Biol.* 1999, 6, 346-349.

65. Robertson, J. W. F., Rodrigues, C. W., Stanford, V. M., Rubinson, K. A., Krasilnikov, O. V. and Kasianowicz, J. J. Single-molecule mass spectrometry in solution using a solitary nanopore. *Proc. Natl. Acad. Sci. USA* 2007, 104, 8207-8211.

66. Ronaghi M., Uhlen, M. & Nyren, P. A sequencing method based on real-time pyrophosphate. *Science* 281, 363-365 (1998)

67. Rosenstein, J., V. Ray, M. Drndic, and K. L. Shepard. Solid-state nanopores integrated with low-noise preamplifiers for high-bandwidth DNA analysis. in *Life Science Systems and Applications Workshop (LiSSA), 2011 IEEE/NIH* (2011).

68. Rosenstein, J., Ray, V., Drndic, M. & Shepard, K. L. Nanopore DNA sensors in CMOS with on-chip low-noise preamplifiers. in *Solid-State Sensors, Actuators and Microsystems Conference (TRANSDUCERS), 2011 16th International* 874-877 (2011).

69. Rothberg, J. M. et al. An integrated semiconductor device enabling non-optical genome sequencing. *Nature* 475, 348-352 (2011).

70. Sauer-Budge, A. F. et al., Unzipping Kinetics of Double Stranded DNA in a Nanopore. *Physical Review Letters* 2003 90(23), 238101-1-238101-4.

71. Schneider, G. F. et al. DNA translocation through graphene nanopores. *Nano Lett* 10, 3163-7 (2010).

72. Seo, T. S., Bai, X., Ruparel, H., Li, Z., Turro, N.J. and Ju, J. Photocleavable fluorescent nucleotides for DNA sequencing on a chip constructed by site-specific coupling chemistry. *Proc. Natl. Acad. Sci. USA* 2004, 101, 5488-5493.

73. Shapovalov, G. and Lester, H. A. Getting transitions in bacterial ion channels measured at 3 microseconds resolution. *J. Gen. Physiol.* 2004, 124, 151-161.
74. Shen, K., Tsai, J., Shi, P. & Kam, L. C. Self-aligned supported lipid bilayers for patterning the cell-substrate interface. *J Am Chem Soc* 131, 13204-5 (2009).
75. Shi, H. & Ratner, B. D. Template recognition of protein-imprinted polymer surfaces. *Journal of Biomedical Materials Research* 49, 1-11 (2000).
76. Shimada, K., Kato, H., Saito, T., Matsuyama, S. & Kinugasa, S. Precise measurement of the self-diffusion coefficient for poly(ethylene glycol) in aqueous solution using uniform oligomers. *Journal of Chemical Physics* 122(2005).
77. Smith, S. B., Cui, Y. and Bustamante, C. Overstretching B-DNA: the elastic response of individual double-stranded and single-stranded DNA molecules. *Science* 1996, 271, 795-799.
78. Sood, A., Kumar, S., Wegener, J., Nampalli, S., Nelson, J., Macklin, J. and Fuller, C. W. Terminal Phosphate Labeled Nucleotides with improved substrate properties for Nucleic Acid Assays. *J. Am. Chem. Soc.* 2005, 127(8), 2394-2395.
79. Srinivasan, M. P., Ratto, T. V., Stroeve, P. & Longo, M. L. Patterned supported bilayers on self-assembled monolayers: Confinement of adjacent mobile bilayers. *Langmuir* 17, 7951-7954 (2001).
80. Storm, A. J. et al. Fast DNA translocation through a solid-state nanopore. *Nano Lett* 5, 1193-1197 (2005).
81. Timp, W. et al. Nanopore Sequencing: Electrical Measurements of the Code of Life. *IEEE Trans Nanotechnol* 9, 281-294 (2010).
82. Wang, H. et al., DNA heterogeneity and Phosphorylation unveiled by Single-Molecule Electrophoresis. *PNAS* 2004 101(37), 13472-13477.
83. Wang, Y., Zheng, D., Tan, Q., Wang, M. X. & Gu, L. Q. Nanopore-based detection of circulating microRNAs in lung cancer patients. *Nat Nanotechnol* 6, 668-74 (2011).
84. Wanunu, M. & Meller, A. Chemically modified solid-state nanopores. *Nano Lett* 7, 1580-5 (2007).
85. Wanunu, M., Sutin, J., McNally, B., Chow, A. & Meller, A. DNA translocation governed by interactions with solid-state nanopores. *Biophys J* 95, 4716-25 (2008).
86. Wanunu, M. et al. Rapid electronic detection of probe-specific microRNAs using thin nanopore sensors. *Nat Nanotechnol* 5, 807-14 (2010).
87. White, R. J. et al. Ionic conductivity of the aqueous layer separating a lipid bilayer membrane and a glass support. *Langmuir* 22, 10777-83 (2006).
88. White, R. J. et al. Single ion-channel recordings using glass nanopore membranes. *J Am Chem Soc* 129, 11766-75 (2007).
89. Wiehelman, K. Investigation of the bicinchoninic acid protein assay: identification of the groups responsible for color formation. *Analytical Biochemistry* 175(1988).
90. Yang, T. L., Baryshnikova, O. K., Mao, H. B., Holden, M. A. & Cremer, P. S. Investigations of bivalent antibody binding on fluid-supported phospholipid membranes: The effect of hapten density. *Journal of the American Chemical Society* 125, 4779-4784 (2003).
91. Yin, P. Tethered Bilayer Membrane Sensors with Small Transmembrane Peptide Ion Channels—Recent Developments, Future Research and Potential Applications. in *Advances in Planar Lipid Bilayers and Liposomes*, Vol. Volume 2 (ed. Ottova-Leitmannova, A.) 49-76 (Academic Press, 2005).
92. Vercoutere, W., Winters-Hilt, S., Olsen, H., Deamer, D., Haussler, D. and Akeson, M. Rapid discrimination among individual DNA hairpin molecules at single-nucleotide resolution using an ion channel. *Nat. Biotech* 2001, 19, 248-252.
93. Vercoutere, W. A. et al., Discrimination Among Individual Watson-Crick Base Pairs at the Terminin of Single DNA Hairpin Molecules. *Nucleic Acids Research* 2003 31 (4), 1311-1318.

What is claimed:

1. A method for determining the nucleotide sequence of a single-stranded DNA comprising:

contacting the single-stranded DNA, wherein the single-stranded DNA is in an electrolyte solution in contact with a nanopore in a membrane and wherein the single-stranded DNA has a primer hybridized to a portion thereof, with a DNA polymerase and at least four deoxyribonucleotide polyphosphate (dNPP) analogues under conditions permitting the DNA polymerase to catalyze incorporation of one of the dNPP analogues into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the polymerase is attached to said nanopore within L/3 of the entrance to said nanopore, wherein $$L = \frac{|I|}{2\pi\sigma} \frac{\mu}{D'}$$

wherein I=ionic current, σ=electrolyte conductivity, D=diffusion constant, and u=mobility of an analyte molecule, wherein each of the four dNPP analogues has the structure:

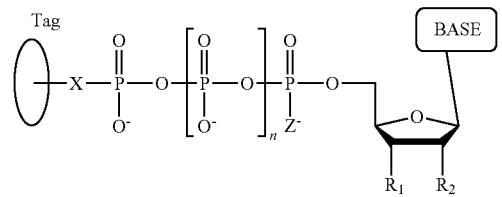

wherein the base is adenine, guanine, cytosine, thymine or uracil, or a derivative of each thereof, wherein $R_1$ is OH, wherein $R_2$ is H, wherein X is O, NH, S or $CH_2$, wherein n is 1, 2, 3, or 4, wherein Z is O, S, or $BH_3$, and with the proviso that (i) the type of base on each dNPP analogue is different from the type of base on each of the other three dNPP analogues, and (ii) either the value of n of each dNPP analogue is different from the value of n of each of the other three dNPP analogues, or the value of n of each of the four dNPP analogues is the same and the type of tag on each dNPP analogue is different from the type of tag on each of the other three dNPP analogues, wherein incorporation of the dNPP analogue results in release of a polyphosphate having the tag attached thereto; and (a) determining which dNPP analogue has been incorporated into the primer to form a DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, as appropriate, thereby identifying the nucleotide residue in the single-stranded DNA complementary to the incorporated dNPP analogue; and (b) iteratively performing steps (a) and (b) for each nucleotide residue of the single-stranded DNA being sequenced, wherein in each iteration of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

2. A method for determining the nucleotide sequence of a single-stranded DNA comprising:

contacting the single-stranded DNA, wherein the single-stranded DNA is in an electrolyte solution in contact with a nanopore in a membrane and wherein the single-stranded DNA has a primer hybridized to a portion thereof, a DNA polymerase and a deoxyribonucleotide polyphosphate (dNPP) analogue under conditions permitting the DNA polymerase to catalyze incorporation of the dNPP analogue into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the polymerase is attached to said nanopore within L/3 of the entrance to said nanopore, wherein $$L = \frac{|I|}{2\pi\sigma} \frac{\mu}{D'}$$

wherein I=ionic current, σ=electrolyte conductivity, D=diffusion constant, and u=mobility of an analyte molecule, wherein the dNPP analogue has the structure:

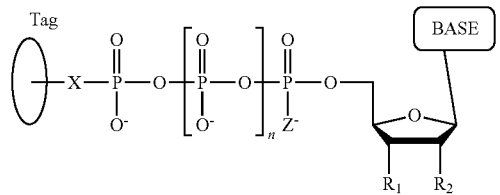

wherein the base is adenine, guanine, cytosine, uracil or thymine, or a derivative of each thereof, wherein $R_1$ is —OH, —O—$CH_2N_3$ or —O-2-nitrobenzyl, wherein $R_2$ is H, wherein X is O, NH, S or $CH_2$, wherein n is 1, 2, 3, or 4, wherein Z is O, S, or $BH_3$, and wherein if the dNPP analogue is not incorporated, iteratively repeating the contacting with a different dNPP analogue until a dNPP analogue is incorporated, with the proviso that (1) the type of base on each dNPP analogue is different from the type of base on each of the other dNPP analogues, and (2) either the value of n of each dNPP analogue is different from the value of n of each of the other three dNPP analogues, or the value of n of each of the four dNPP analogues is the same and the type of tag on each dNPP analogue is different from the type of tag on each of the other three dNPP analogues, wherein incorporation of a dNPP analogue results in release of a polyphosphate having the tag attached thereto;

a. determining which dNPP analogue has been incorporated into the primer to form a DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, as appropriate, thereby identifying the nucleotide residue in the single-stranded DNA complementary to the incorporated dNPP analogue;

b. iteratively performing steps (a) and (b) for each nucleotide residue of the single-stranded DNA being sequenced, wherein in each iteration of step (a) the dNPP analogue is incorporated into the DNA extension product resulting from the previous iteration of step (a) if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

3. The method of claim 1, wherein the base is selected from the group consisting of adenine, guanine, cytosine, thymine, 7-deazaguanine, 7-deazaadenine or 5-methylcytosine.

4. The method of claim 1, further comprising a washing step after each iteration of step (b) to remove unincorporated dNPP analogues from contact with the single-stranded DNA.

5. The method of claim 1, wherein the single-stranded DNA, electrolyte solution and nanopore in the membrane are located within a single container.

6. The method of claim 1, wherein the dNPP analogues have the following structures:

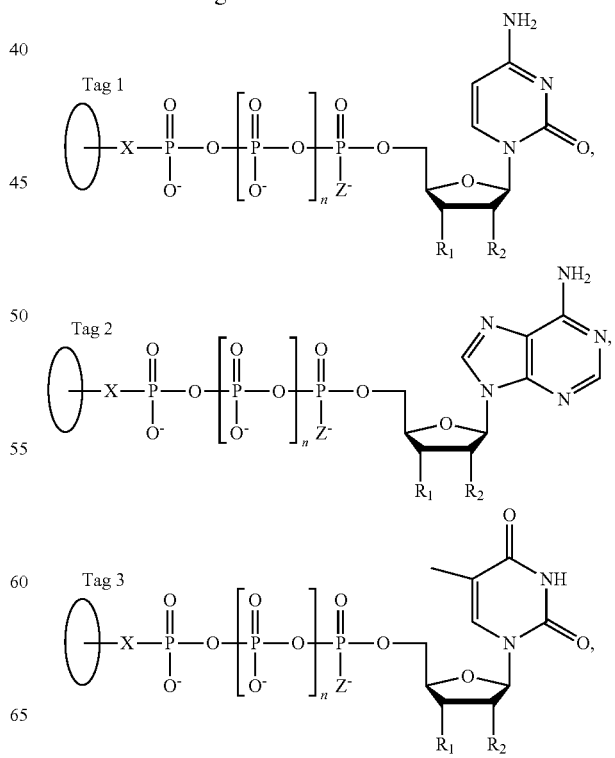

85
-continued

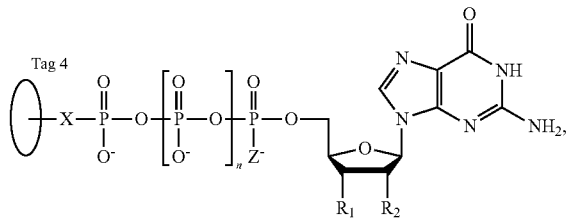

wherein $R_1$ is OH, wherein $R_2$ is H or OH, wherein Z is O, S, or $BH_3$, and wherein the base is adenine, guanine, cytosine, thymine, uracil, a 7-deazapurine or a 5-methylpyrimidine.

7. The method of claim 1, wherein the tag is a mononucleotide, a dinucleotide, a trinucleotide, a tetranucleotide, a pentanucleotide or a hexanucleotide and wherein the base of the mononucleotide, the dinucleotide, the trinucleotide, the tetranucleotide, the pentanucleotide or the hexanucleotide is the same type of base as the base of the dNPP analogue.

8. The method of claim 1, wherein the dNPP analogue is chosen from the following:

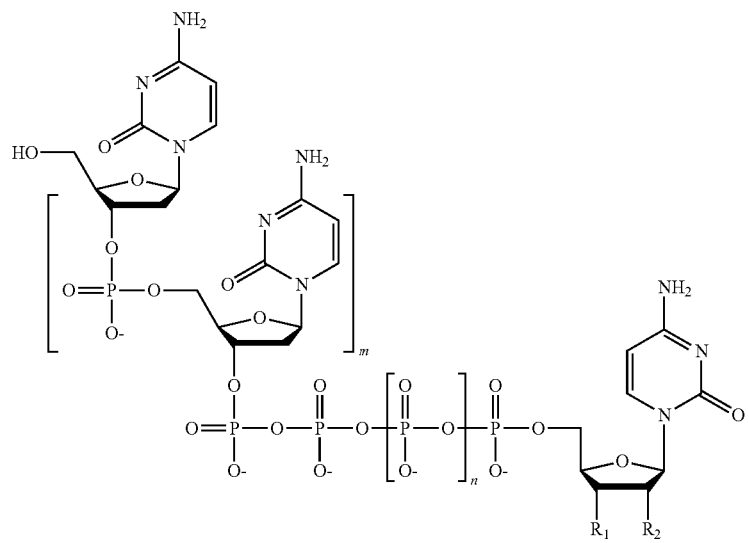

$(dCp)_m$-$(PO_4)_n$-dC

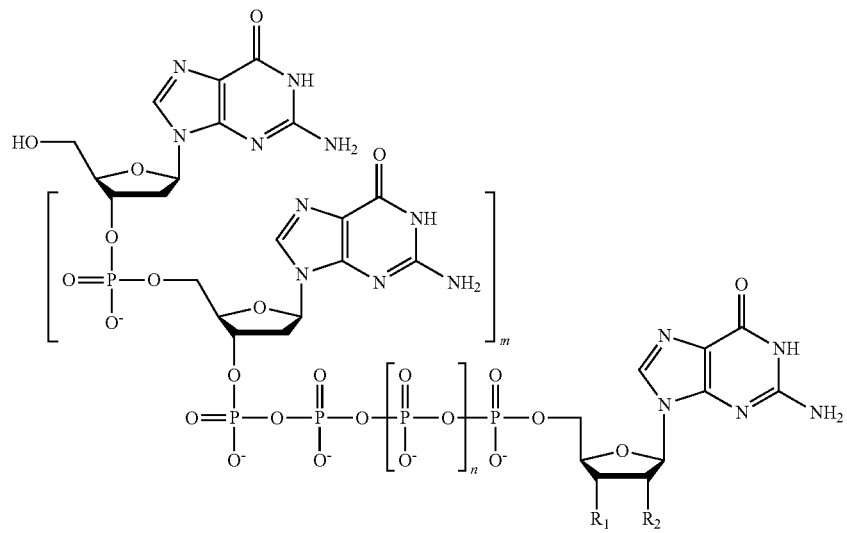

$(dGp)_m$-$(PO_4)_n$-dG

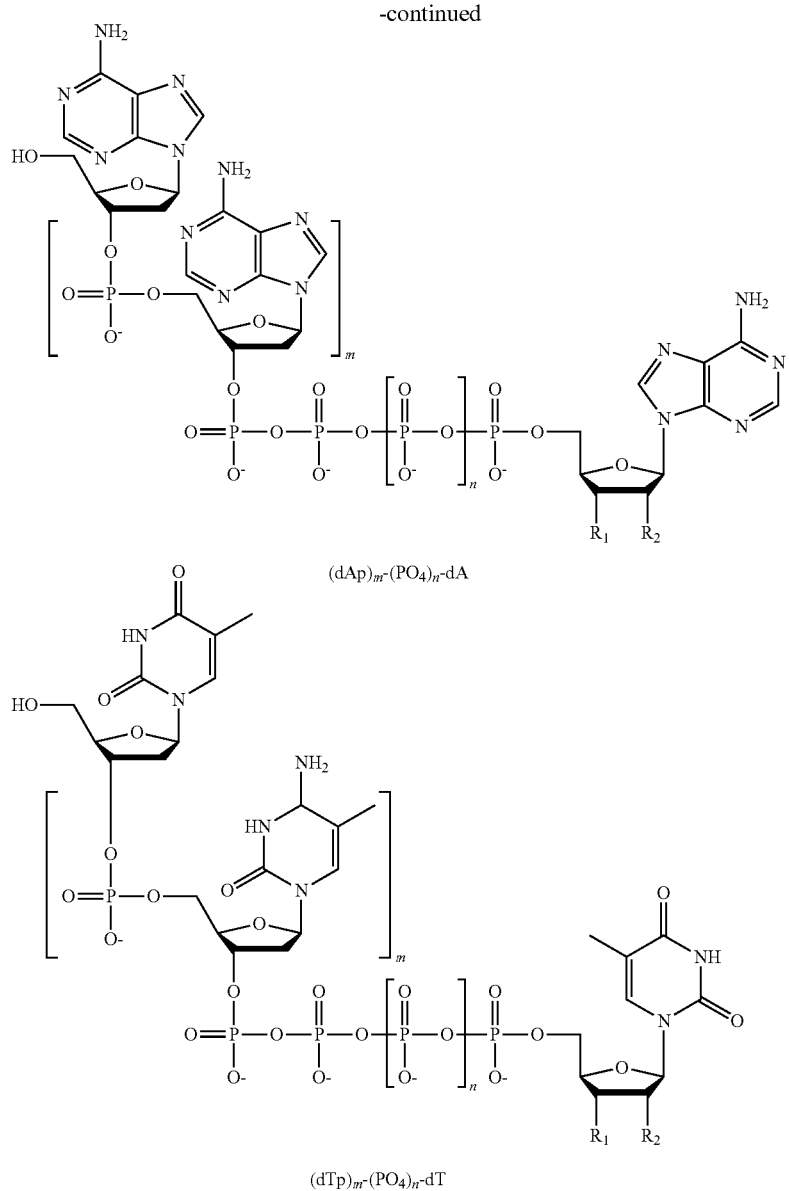

(dAp)$_m$-(PO$_4$)$_n$-dA (dTp)$_m$-(PO$_4$)$_n$-dT wherein in each structure n is, independently, 1, 2, 3 or 4, and m is, independently, an integer from 0 to 100, and wherein when m is 0 the terminal phosphate of the dNPP is bonded directly to the 3' O atom of the nucleoside shown on the left hand side of the structure, and wherein the value of n is different for each type of base.

9. The method of claim 1, wherein the electronic change is a change in current amplitude.

10. The method of claim 1, wherein the electronic change is a change in conductance of the nanopore.

11. The method of claim 1, wherein the nanopore is biological.

12. The method of claim 1, wherein the nanopore is proteinaceous.

13. The method of claim 1, wherein the nanopore comprises alpha hemolysin.

14. The method of claim 1, wherein the nanopore is graphene.

15. The method of claim 1, wherein the nanopore is a solid-state nanopore or the nanopore is in a solid-state membrane.

16. The method of claim 2, wherein R$_1$ is —O—-CH$_2$N$_3$ or —O-2-nitrobenzyl, further comprising treating the incorporated dNPP analogue so as to remove the —CH$_2$N$_3$ or O-2-nitrobenzyl and result in an OH group attached to the 3' position thereby permitting incorporation of a further dNPP analogue.

17. The method of claim 2, wherein the base is selected from the group consisting of adenine, guanine, cytosine, thymine, 7-deazaguanine, 7-deazaadenine or 5-methylcytosine.

18. The method of claim 2, further comprising a washing step after each iteration of step (b) to remove unincorporated dNPP analogues from contact with the single-stranded DNA.

19. The method of claim 1, wherein L is less than 0.7 nm.

20. The method of claim 2, wherein L is less than 0.7 nm.

* * * * *